US012758648B2

(12) United States Patent
Harris et al.

(10) Patent No.: US 12,758,648 B2
(45) Date of Patent: *Oct. 13, 2026

(54) POLYOXAZOLINE-LIPID CONJUGATES AND LIPID NANOPARTICLES AND PHARMACEUTICAL COMPOSITIONS INCLUDING SAME

(71) Applicant: Serina Therapeutics (AL), Inc., Huntsville, AL (US)

(72) Inventors: J Milton Harris, Huntsville, AL (US); Michael Bentley, Huntsville, AL (US); Tacey Viegas, Madison, AL (US); Randall Moreadith, Huntsville, AL (US); Robert J Sharpe, Meridianville, AL (US); Kunsang Yoon, Madison, AL (US); Zhihao Fang, Madison, AL (US); Rebecca Weimer, Huntsville, AL (US)

(73) Assignee: Serina Therapeutics (AL), Inc., Huntsville, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/387,528

(22) Filed: Nov. 7, 2023

(65) Prior Publication Data

US 2024/0108750 A1 Apr. 4, 2024

Related U.S. Application Data

(62) Division of application No. 17/665,190, filed on Feb. 4, 2022, now Pat. No. 12,233,132.

(60) Provisional application No. 63/147,470, filed on Feb. 9, 2021.

(51) Int. Cl.
*A61K 47/69* (2017.01)
*A61K 39/00* (2006.01)

(52) U.S. Cl.
CPC .......... *A61K 47/6935* (2017.08); *A61K 39/00* (2013.01)

(58) Field of Classification Search
CPC ................ A61K 47/6935; A61K 39/00; A61K 48/0041; A61K 2039/53; C12N 15/88; A61P 37/00
See application file for complete search history.

(56) References Cited

U.S. PATENT DOCUMENTS

| | | | | |
|---|---|---|---|---|
| 4,235,871 | A | 11/1980 | Papahadjopoulos et al. | |
| 7,943,141 | B2 | 5/2011 | Harris et al. | |
| 8,088,884 | B2 | 1/2012 | Harris et al. | |
| 8,101,706 | B2 | 1/2012 | Yoon et al. | |
| 8,110,651 | B2 | 2/2012 | Yoon et al. | |
| 8,383,093 | B1 | 2/2013 | Moreadith et al. | |
| 8,883,211 | B2 | 11/2014 | Bentley et al. | |
| 9,284,411 | B2 | 3/2016 | Bentley et al. | |
| 2004/0166151 | A1 | 8/2004 | Jorgensen et al. | |
| 2011/0313017 | A1* | 12/2011 | Heyes .................. | A61K 9/1272 435/375 |
| 2018/0065920 | A1* | 3/2018 | Manoharan .......... | A61K 31/713 |
| 2020/0230058 | A1 | 7/2020 | Geall et al. | |

FOREIGN PATENT DOCUMENTS

| | | | |
|---|---|---|---|
| WO | WO 2008/106186 | 9/2008 | |
| WO | WO 2009/043027 | 4/2009 | |
| WO | WO 2020264505 | 12/2020 | |
| WO | WO-2020264505 A1 * | 12/2020 | ............. A61K 31/05 |

OTHER PUBLICATIONS

Jones, R. G.et al (2016). Source-based nomenclature for single-strand homopolymers and copolymers (IUPAC Recommendations 2016). Pure and Applied Chemistry, 88(10-11), 1073-1100. (Year: 2016).*
Patani GA, LaVoie EJ. Bioisosterism: A Rational Approach in Drug Design. Chem Rev. Dec. 19, 1996;96(8):3147-3176. (Year: 1996).*
Szoka, Francis Jr., et al., Proc. Natl. Acad. Sci. USA (PNAS), "Procedure for Preparation of Liposomes with Large Internal Aqueous Space and High Capture by Reverse-Phase Evaporation", vol. 75, No. 9, pp. 4194-4198, Sep. 1978.
Zhu et al., "Preparation of Large Monodisperse Vesicles", PLoS One, 2009, 4(4):e5009, Epub Apr. 6, 2009.
International Search Report dated Apr. 26, 2022 of corresponding International Patent Application No. PCT/US22/15314.
Non-Final Office Action dated Jan. 3, 2024 of corresponding U.S. Appl. No. 17/665,190.
U.S. Appl. No. 13/549,312, filed Jul. 13, 2012 entitled "Facile Synthesis of Gamma Folate Esters and Polymer Conjugates Thereof".
Gulyuz, Sevgi, et al., "Synthesis, biocompatability and gene encapsulation of poly (2-Ethyl 2-Oxazoline)-dioleoyl phosphatidylethanolamine (PEtOx-DOPE) and post-modifications with peptides and fluorescent dye coumarin", International Journal of Polymeric Materials and Polymeric Biomaterials, vol. 70, No. 14, Jul. 7, 2020, pp. 981-993.
Simon, L. et al., "Recent advances and prospects in nano drug delivery systems using lipopolyoxazolines", International Journal of Pharmaceutics, Elsevier, Amsterdam, NL, vol. 585, Jun. 9, 2020.
Extended European Search Report dated Oct. 23, 2025 of corresponding European Patent Application No. 22753169.6.

* cited by examiner

*Primary Examiner* — James H Alstrum-Acevedo
*Assistant Examiner* — Pierre Paul Eleniste
(74) *Attorney, Agent, or Firm* — Bradley Arant Boult Cummings LLP

(57) ABSTRACT

POZ-lipid conjugates and lipid nanoparticles (LNPs) including POZ-lipid conjugates used to facilitate delivery of an encapsulated payload. LNPs including POZ-lipid conjugates and a nucleic acid payload such as, but not limited to, mRNA or modified mRNA are disclosed. Such LNPs have no immunogenicity or reduced immunogenicity as compared to a corresponding LNP containing a PEG-lipid.

23 Claims, 1 Drawing Sheet

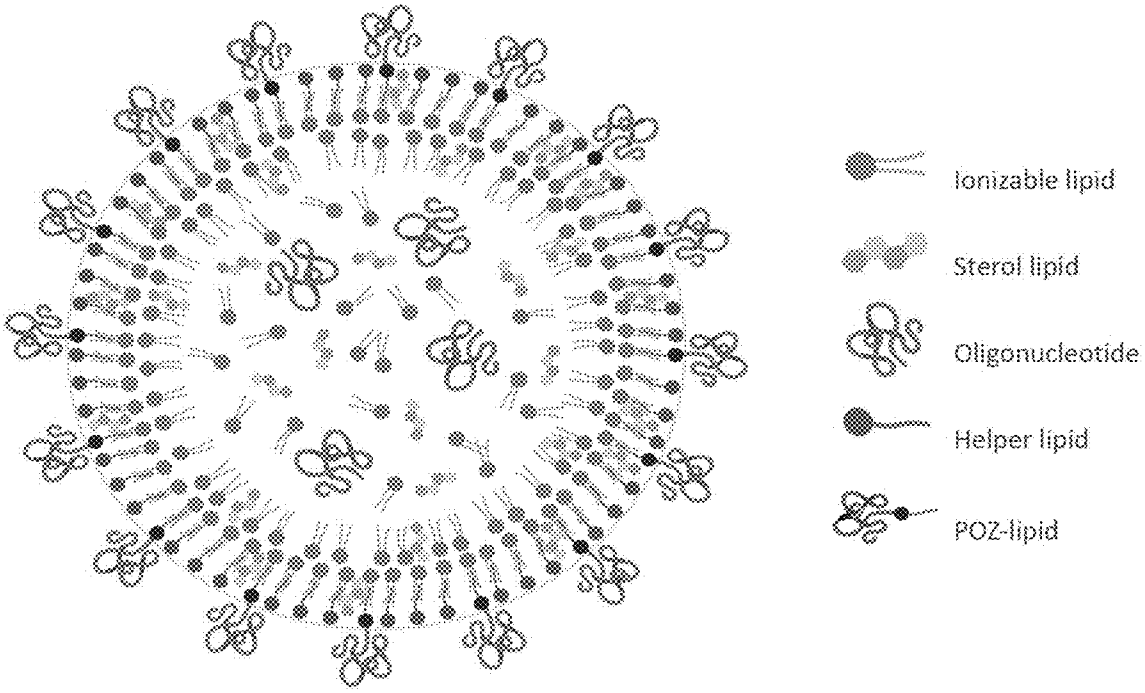
Ionizable lipid
Sterol lipid
Oligonucleotide
Helper lipid
POZ-lipid

POLYOXAZOLINE-LIPID CONJUGATES AND LIPID NANOPARTICLES AND PHARMACEUTICAL COMPOSITIONS INCLUDING SAME

FIELD OF THE DISCLOSURE

The present disclosure relates to polyoxazoline-lipid conjugates, methods of synthesis, and use of these conjugates in lipid nanoparticles and pharmaceutical compositions. Lipid nanoparticles incorporating oligonucleotides such as mRNA, DNA, and siRNA for delivery into living cells is also contemplated.

BACKGROUND

Nucleic-acid (particularly mRNA)-based vaccines offer some advantages over other vaccine technologies. For example, nucleic acid-based vaccines can be rapidly produced with reduced development time and costs by using a common manufacturing platform and purification methods regardless of the oligonucleotide payload. In addition, mRNA-based vaccines, when taken up by cells that are capable of translating the encoded protein, may be capable of presenting polypeptide(s) as an antigen. These cells include antigen-presenting cells such as macrophages and dendritic cells.

However, current nucleic acid-based vaccines suffer from several shortcomings. For example, mRNA is rapidly degraded by nucleases in the body and is not readily taken up by most cell types if it is simply complexed to a polyamine such as protamine. Moreover, a key factor hampering both DNA and mRNA vaccine development is the lack of a potent, well-tolerated, non-immunogenic delivery system that provides for repeated administration(s) without serious adverse events.

Efforts to address these shortcomings have resulted in encapsulation of mRNA payloads (as well as other oligonucleotide payloads) into lipid nanoparticles (LNPs), which protects mRNA from enzymatic degradation and enhances cell uptake and expression by up to 1000-fold compared to mRNA complexed to a polyamine. Such LNPs are typically composed of an ionizable lipid (which complexes with the oligonucleotide), cholesterol (to provide flexibility), a lipid that includes a polyethylene glycol (PEG) moiety (to stabilize the lipid nanoparticles and prevent fusion with other nanoparticles), and a helper lipid (to provide structural integrity) such as distearoylphosphatidylcholine (DSPC). For example, U.S. Patent Publication No. 2020/0230058 discloses a liposome within which RNA encoding an immunogen of interest is encapsulated, where the liposome includes at least one PEG-lipid and where the PEG is present on the liposome's exterior and has an average molecular mass between 1 kDa and 3 kDa.

Early work with small interfering RNA (siRNA) has identified the ionizable lipid as one of the major components that is essential for potency. Ionizable lipids are critically important for endosomal escape once the LNP is trafficking through the endosomal compartments in the cell.

LNPs are generally considered to be biocompatible nanocarriers with an acceptable safety profile and capacity to carry oligonucleotide payloads. Yet, as briefly noted above, issues have been noted regarding immunogenicity of certain LNPs when administered to animals and humans. In particular, the commonly used PEG-lipids in LNPs may compromise vaccine safety due to the impact of anti-PEG immune responses. In fact, it is increasingly recognized that treating patients with PEGylated components, including PEG-lipids, can lead to the formation of antibodies that specifically recognize and bind to PEG (i.e., anti-PEG antibodies). Also, anti-PEG antibodies are found in patients who have never been treated with PEGylated drugs but have been exposed to products containing PEG (e.g., cosmetics and food).

Consequently, treating patients who have pre-formed anti-PEG antibodies with LNPs containing PEG-lipids may result in accelerated blood clearance of LNPs containing PEG-lipids, reduced/compromised efficacy, hypersensitivity reactions, and, in some cases, severe allergic reactions to PEG. This immunogenicity of PEG may cause serious adverse events when the subject receives repeated vaccinations over time with LNPs containing PEG-lipids, or if the subject has been previously exposed to products containing PEG. Indeed, in the initial wave of global vaccinations against SARS-CoV-2 ("COVID-19") with the mRNA vaccines from Pfizer/BioNTech and Moderna, caregivers reported an unusually high incidence rate of life-threatening side effects including anaphylaxis. The vast majority of anaphylaxis occurred in women (approximately 90%), which have been shown to be due to antibodies to PEG. While the exact mechanism(s) mediating anaphylaxis are not yet known, it is likely that the life-threatening immune response is due to basophil degranulation in patients who have been previously sensitized to PEG by exposure to PEG-containing cosmetics, food, or medications.

As such, there remains a need to address the shortcomings of current LNP technology and for improved ways of delivering nucleic acid vaccines. In particular, it would be advantageous to identify LNP formulations with markedly reduced or lacking immunogenicity. It would also be advantageous to identify LNP formulations with acceptable reactogenicity profiles after initial administration of the LNP and after subsequent administration(s) of the LNP. In addition, while the role of intracellular stability of the polymer-lipid in LNP formulations has still to be fully explored, and the details of cellular uptake and subsequent release of the oligonucleotide into the cell are still poorly understood, it is generally considered necessary for the polymer-lipid in the LNP to be shed from the LNP in order for the payload to be released into the cell (although this point is controversial). For this reason and others, it is essential that the field of LNP technology have available a reduced or non-immunogenic polymer lipid to provide a range of in vivo stabilities. The POZ-lipid conjugate of the present disclosure provides a reduced or non-immunogenic alternative to the PEG-lipid used in current LNP formulations and, thus, also provides an improved, non-immunogenic LNP for use in vaccine delivery systems. In addition, LNPs made in accordance with the present disclosure possess multiple properties that are potentially beneficial to the art, including but not limited to, particle size, polydispersity, freeze/thaw stability, oligonucleotide encapsulation efficiency, maintenance of oligonucleotide integrity, endosomal escape, transfection efficiency, and others.

SUMMARY OF THE INVENTION

The present disclosure relates to novel polymer lipids including polyoxazoline (POZ) attached to a lipid with variable degrees of stability between the polymer and the lipid in a biological system. In this aspect, the polyoxazoline-lipid (POZ-lipid) conjugate have controllable degradability via the linkage between the POZ and lipid. The POZ-lipid conjugate can be incorporated into a lipid nanoparticle and, in so doing, confer unique properties to the lipid nanoparticle.

In one embodiment, the lipid nanoparticle compositions of the present disclosure may include a POZ-lipid as described herein. In another embodiment, compositions of the present disclosure include a POZ-lipid as described herein, a cationic or ionizable lipid, and optional additional lipids. In yet another embodiment, the compositions of the present disclosure include a POZ-lipid as described herein as well as additional lipids such as phospholipids, structural lipids, and cholesterol, an oligonucleotide payload, and combinations thereof. The lipid nanoparticle compositions that capsulate the oligonucleotide payload may provide for expression of the payload in suitable cell types that take up the lipid nanoparticle, thus providing a therapeutic response to the payload. In one embodiment, the oligonucleotide payloads include, but are not limited to, mRNA vaccines against an infectious disease such as SARS-CoV-2, rabies, influenza, and others.

In another embodiment, the lipid nanoparticle compositions may also be used in various therapeutic approaches including, but not limited to cancer immunotherapy, gene therapy, enzyme replacement, and combinations thereof.

The present disclosure also relates to a compound of Formula I

R—POZ-L-Lipid    I wherein R includes an initiating group,

POZ includes a polyoxazoline polymer,

L includes a linking group with controllable degradability in physiological media, and Lipid includes a non-charged lipid comprising at least one hydrophobic moiety.

In one embodiment, the POZ in Formula I is $$—\{[N(COX)CH_2CH_2]_o—[N(COR_2)CH_2CH_2]_n\}_a—$$

where X includes a functional group including an alkyne group, a triazole with attached carboxylic acid, or a combination thereof, o ranges from 0 to 10, n ranges from 1 to 1000, and $R_2$ includes a hydrogen, a substituted or unsubstituted alkyl, alkyne-substituted alkyl, or an substituted or unsubstituted aralkyl group, and a is ran, which indicates a random copolymer, or block, which indicates a block copolymer.

In another embodiment, the POZ has a polydispersity index of about 1.01 to about 1.20. In still another embodiment, the POZ has a molecular weight between 500 Daltons and 5,000 Daltons. In yet another embodiment, R includes a hydrogen, a substituted or unsubstituted alkyl, an alkyne-substituted alkyl, a triazole with attached carboxylic acid, or a substituted or unsubstituted aralkyl group. L may include ethers, esters, carboxylate esters, carbonate esters, carbamates (including, but not limited to, ethyl carbamate (urethane)), amines, amides, disulfides, and combinations thereof. In another embodiment, Lipid may include two hydrophobic moieties. For example, Lipid may include a phospholipid, a glycerolipid, a dialkylamine, or a combination thereof. In one embodiment, Lipid includes 1,2-dimyristoyl-sn-glycerol, 1,2-dilauroyl-sn-glycerol, or a combination thereof.

In this aspect of the present disclosure, Formula I may be one of the following:

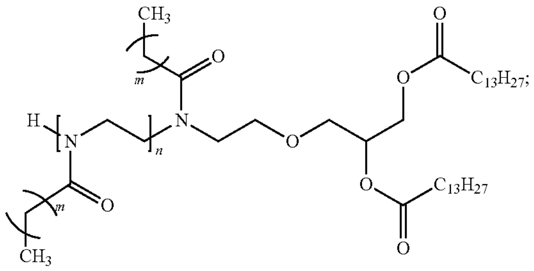

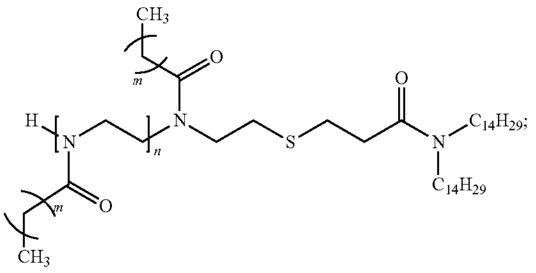

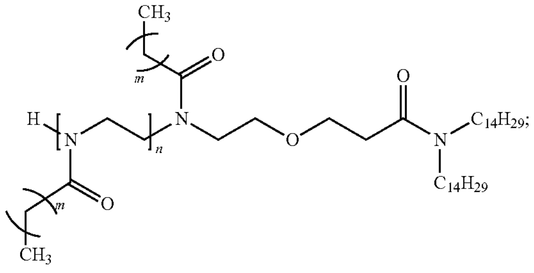

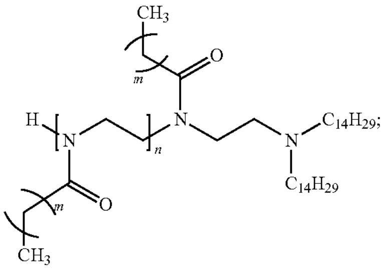

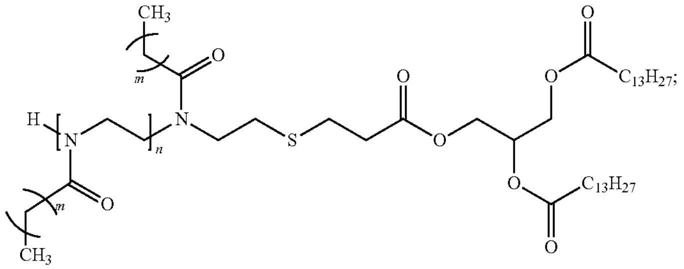

-continued

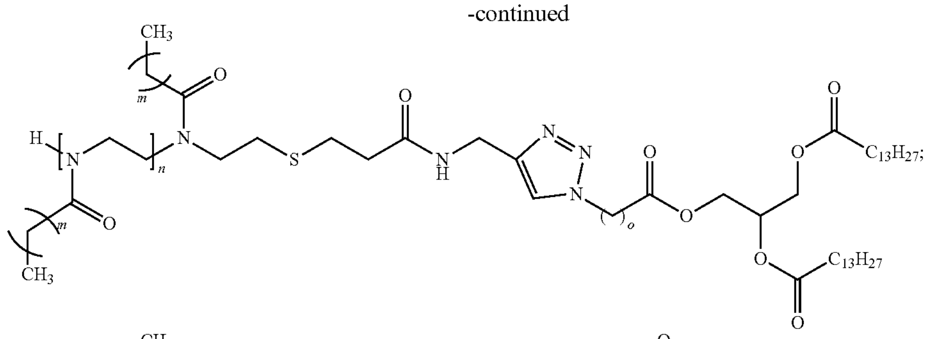

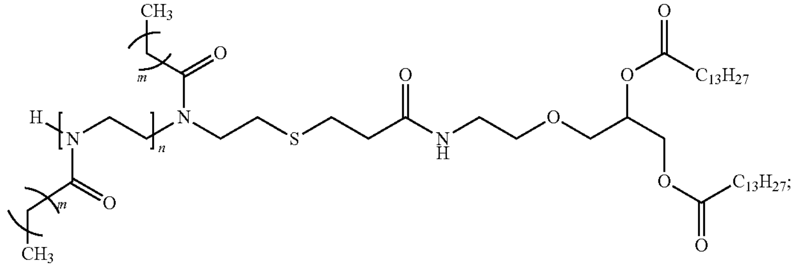

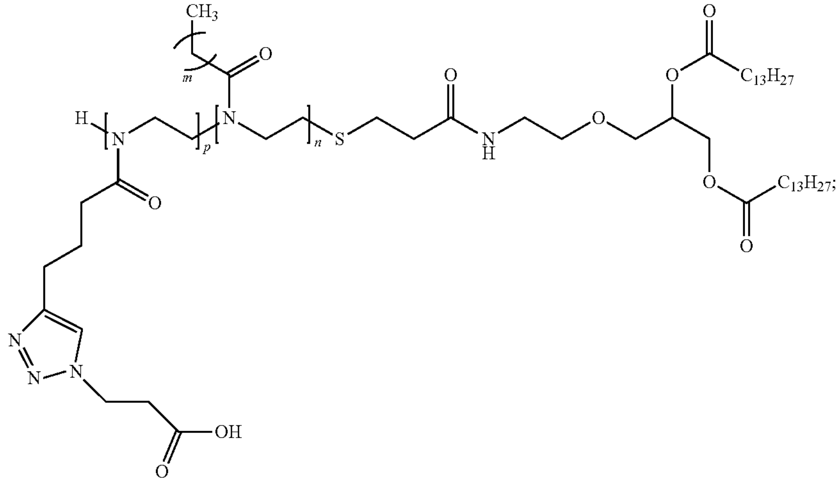

and

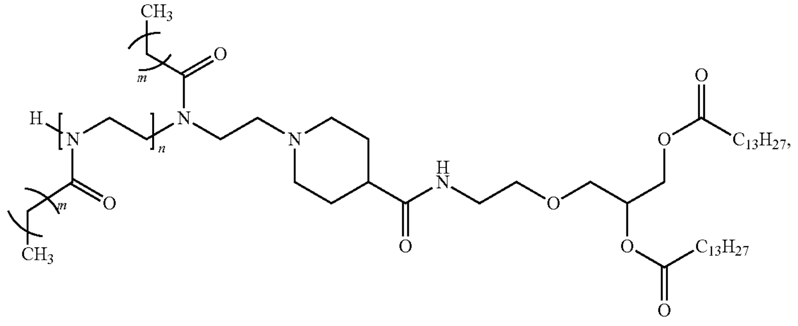

wherein m is 1-2, n ranges from 1 to 1000, o ranges from 1 to 5, and p ranges from 1 to 10.

The present disclosure also relates to a compound of Formula II $$\text{Lipid-L}_1\text{-(POZ)}_n^a\text{-T} \qquad \text{II}$$

wherein

Lipid include a non-charged lipid comprising at least one hydrophobic moiety, $L_1$ includes a linking group with controllable degradability in physiological media, POZ includes a polyoxazoline polymer of the structure $[N(COR_2)CH_2CH_2]$, wherein $R_2$ is independently selected for each repeating unit of the polyoxazoline polymer from an unsubstituted or substituted alkyl, alkenyl, alkyne-substituted alkyl, aralkyl, heterocyclylalkyl, or active functional group, n ranges from 1 to 1,000, a is ran, which indicates a random copolymer, or block, which indicates a block copolymer, and T comprises a group at the terminating terminus.

In this aspect, $L_1$ may include ethers, esters, carboxylate esters, carbonate esters, carbamates (including, but not limited to, ethyl carbamate (urethane)), amines, amides, disulfides, and combinations thereof. In one embodiment, the $L_1$ is a triazole. In another embodiment, T includes Z—B-Q, wherein Z includes S, O, or N, B is an optional linking group, and Q is a terminating nucleophile or portion thereof.

In this aspect, Lipid may include two hydrophobic moieties. For example, Lipid may include a phospholipid, a glycerolipid, a dialkylamine, or a combination thereof. In one embodiment, Lipid includes 1,2-dimyristoyl-sn-glycerol, 1,2-dilauroyl-sn-glycerol, or a combination thereof.

In one embodiment, Formula II is one of the following:

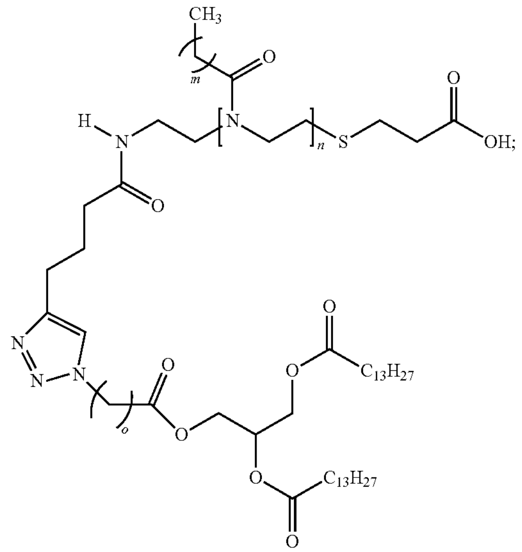

;

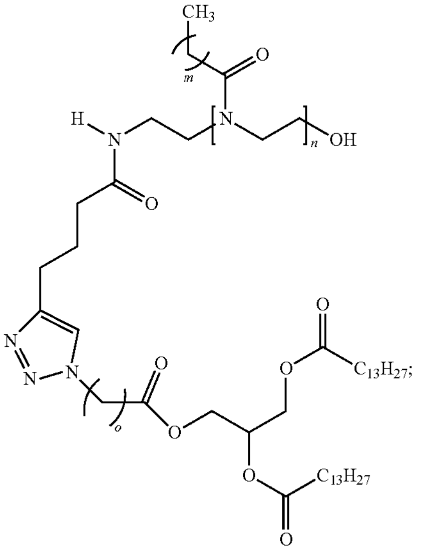

;

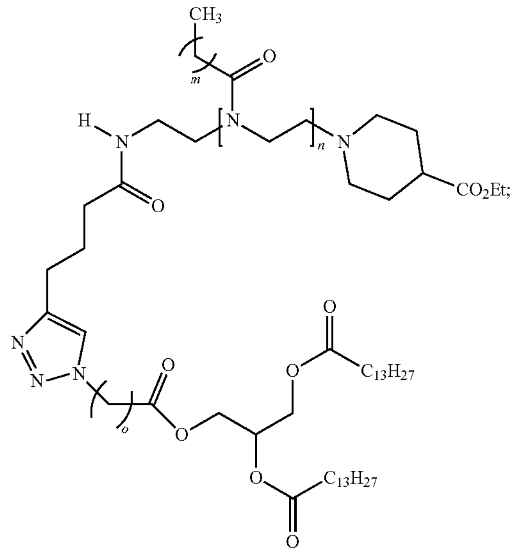

and

-continued

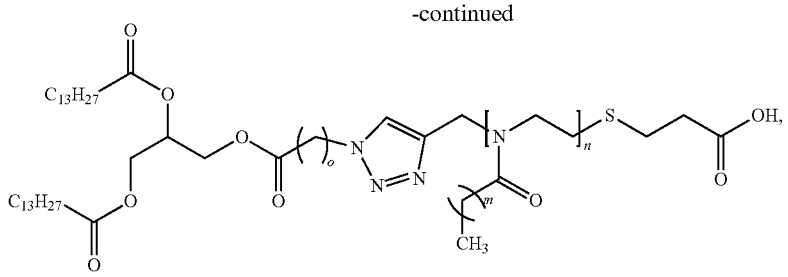

wherein m is 1-2, n ranges from 1 to 1000, and o ranges from 1 to 5.

The present disclosure also relates to a compound of Formula III $$R—(POZ)_n^a\text{-}Z\text{-}L_2\text{-Lipid} \qquad \text{III}$$

wherein R includes an initiating group;

POZ includes a polyoxazoline polymer of the structure $[N(COR_2)CH_2CH_2]$, wherein $R_2$ is independently selected for each repeating unit of the polyoxazoline polymer from an unsubstituted or substituted alkyl, alkenyl, alkyne-substituted alkyl, aralkyl, heterocycylalkyl group, or an active functional group, n ranges from 1 to 1,000, a is ran, which indicates a random copolymer, or block, which indicates a block copolymer, Z includes S, O, or N, $L_2$ includes a linking group with controllable degradability in physiological media, and Lipid includes a non-charged lipid comprising at least one hydrophobic group.

In this aspect, $L_2$ may include ethers, esters, carboxylate esters, carbonate esters, carbamates (including, but not limited to, ethyl carbamate (urethane)), amines, amides, disulfides, and combinations thereof. In one embodiment, Lipid includes two hydrophobic moieties. For example, Lipid may include a phospholipid, a glycerolipid, a dialkylamine, or a combination thereof. In another embodiment, Lipid includes 1,2-dimyristoyl-sn-glycerol, 1,2-dilauroyl-sn-glycerol, or a combination thereof.

In one embodiment, R includes a hydrogen, or a substituted or unsubstituted alkyl, and wherein n ranges from 15 to 35.

The present disclosure also relates to a compound of Formula IV

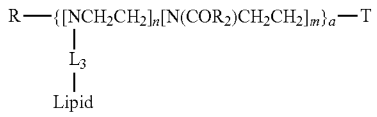

IV wherein

R includes an initiating group, $L_3$ includes a linking group with controllable degradability in physiological media, Lipid comprises a non-charged lipid comprising at least one hydrophobic moiety, n ranges from 1 to 5, $R_2$ is independently selected for each repeating unit from an unsubstituted or substituted alkyl, alkenyl, alkyne-substituted alkyl, aralkyl, heterocyclylalkyl, or active functional group, m ranges from 1 to 100.

a is ran, which indicates a random copolymer, or block, which indicates a block copolymer, and T includes a group at the terminating terminus.

In this aspect, $L_3$ may include ethers, esters, carboxylate esters, carbonate esters, carbamates, amines, amides, disulfides, and combinations thereof. In one embodiment, $L_3$ includes a triazole. In another embodiment, T includes Z—B-Q, wherein Z includes S, O, or N, B is an optional linking group, and Q is a terminating nucleophile or portion thereof.

Lipid may include two hydrophobic moieties. For example, Lipid may include a phospholipid, a glycerolipid, a dialkylamine, or a combination thereof. In one embodiment, Lipid may include 1,2-dimyristoyl-sn-glycerol, 1,2-dilauroyl-sn-glycerol, or a combination thereof.

In one embodiment, any of the above compounds of Formula I-IV have a rate of hydrolysis that is determined at least in part by L, $L_1$, $L_2$, or $L_3$ (as applicable). In another embodiment, any of the above compounds of Formula I-IV have a hydrolysis half-life in 50 percent human plasma of about 10 minutes or less. In yet another embodiment, any of the above compounds of Formula I-IV have a hydrolysis half-life in 50 percent human plasma of about 120 hours or more.

A composition may be formed including any of the above compounds of Formula I-IV. In one embodiment, such compositions may further include a cationic or ionizable lipid. In another embodiment, the present disclosure relates to a method for treating a disorder or a disease in an animal, including the step of administering to the animal an effective amount of such compositions. In yet another embodiment, the present disclosure relates to a method for raising a protective immune response in an animal, including the step of administering to the animal an effective amount of such compositions. In either regard, the step of administenring may include delivering such compositions to the animal via subcutaneous, intravenous, intramuscular, intradermal or aerosol routes.

BRIEF DESCRIPTION OF THE DRAWINGS

Further features and advantages of the invention can be ascertained from the following detailed description that is provided in connection with the drawings described below:

FIG. 1 shows a lipid nanoparticle in accordance with an embodiment of the present disclosure.

DETAILED DESCRIPTION

The present disclosure provides a range of novel POZ-lipid conjugates and lipid nanoparticles (LNPs) including a POZ-lipid conjugate of the disclosure. The LNPs may be used to facilitate the intracellular delivery of biologically active and therapeutic molecules. In one embodiment, the LNPs may be used to deliver an encapsulated payload, e.g., a nucleic acid payload including, but not limited to, mRNA or modified mRNA. Because LNPs including a POZ-lipid conjugate of the present disclosure have no immunogenicity or reduced immunogenicity as compared to a corresponding LNP containing a PEG-lipid, such LNPs provide a safer method of delivering nucleic acid vaccines. Furthermore, while not being bound to particular theory, it is anticipated that novel POZ-lipids, as a component of a LNP, may also confer unique properties when compared to PEG-lipids, and that the resulting LNPs may display unique uptake, distribution and efficacy when administered as a therapeutic. Moreover, the POZ-lipids of the present disclosure have varying degrees of stability, which may advantageously provide additional flexibility in "designing" LNPs that include POZ-lipids. The disclosure also relates to pharmaceutical compositions that include such LNPs and that are useful to deliver therapeutically effective amounts of biologically active molecules into the cells of patients.

Polyoxazolines (POZ) are biocompatible polymers and retain good solubility in many hydrophilic and hydrophobic solvents. POZ are also resistant to oxidative degradation and do not undergo bioaccumulation. POZ has conferred stealth capability and good permeation through mucosal tissues when grafted to silica particles, gold particles, ZnO nanocrystals, and magnetic particles.

LNPs are amphiphilic spherical vesicles formed by one or more lipid layers enveloping an aqueous core with size ranging from about 20 nm to a few microns. LNPs of the prior art generally comprise a cationic or ionizable lipid combined with: (i) a helper lipid that supports the bilayer structure and facilitates the endocytosis; (ii) a sterol lipid (i.e., cholesterol) to stabilize the lipid bilayer of the LNP; and (iii) a PEG-lipid to provide the LNP with a hydrating layer to improve colloidal stability, prevent fusion of nascent particles, reduce protein adsorption and non-specific uptake, and prevent reticuloendothelial clearance. However, as mentioned above, the PEG-lipid in these LNPs may compromise patient safety due to the potential of anti-PEG immune responses. Using the POZ-lipids of the present disclosure, which have not been used in LNPs, particularly LNPs for the delivery of nucleic acids, provide a solution to the immunogenicity problem with PEGylated LNPs and also provide LNPs with unique uptake, distribution, and efficacy (as compared to PEGylated LNPs) when administered as a therapeutic.

Definitions

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

The articles "a" and "an" are used herein to refer to one or to more than one (i.e., to at least one) of the grammatical object of the article. By way of example, "an element" means one element or more than one element.

The terms "about" and "approximately" shall generally mean an acceptable degree of error or variation for the quantity measured given the nature or precision of the measurements. Numerical quantities given in this description are approximate unless stated otherwise, meaning that the term "about" or "approximately" can be inferred when not expressly stated.

As used herein, the term "active" or "activated" when used in conjunction with a particular functional group refers to a functional group that reacts readily with an electrophile or a nucleophile on another molecule. This is in contrast to those groups that require catalysts or impractical reaction conditions in order to react (i.e., a "non-reactive" or "inert" group).

As used herein, the term "physiologically degradable" or "physiologically releasable" refers to a linkage containing a cleavable moiety. The terms degradable and releasable do not imply any particular mechanism by which the linker is cleaved.

As used herein, the term "link", "linked" "linkage" or "linker" when used with respect to a POZ polymer, POZ conjugate, an agent, or compound described herein, or components thereof, refers to bonds that normally are formed as the result of a chemical reaction and typically are covalent linkages.

As used herein, the term "lipid nanoparticle" or "LNP" is used to encompass any of the many types of nanoparticles, including liposomes, that are formed by a lipid layer or layers surrounding a core containing a molecule to be released into the body. Liposomes generally have one or more contiguous lipid bilayers encapsulating an aqueous core. Other forms of liposome-like nanocarriers may have a lipid monolayer, or a non-contiguous bilayer, and may or may not have an aqueous core.

As used herein, the term "hydrophilic", for example with reference to a hydrophilic group, refers to a compound or molecule, or a portion thereof, where the interaction with water is thermodynamically more favorable than interaction with oil or other hydrophobic solvents. A hydrophilic compound is able to dissolve in, or be dispersed in, water.

As used herein, the term "hydrophobic", for example with reference to a hydrophobic portion, refers to a compound or molecule, or a portion thereof, where the interaction with water is thermodynamically less favorable than interaction with oil or other hydrophobic solvents. A hydrophobic compound is able to dissolve in, or be dispersed in, oil or other hydrophobic solvents.

As used herein, the term "inert" or "non-reactive" when used in conjunction with a particular functional group refers to a functional group that does not react readily with an electrophile or a nucleophile on another molecule and require catalysts or impractical reaction conditions in order to react.

As used herein, the term "pendent group" refers to a part of the POZ polymer that is attached to the POZ polymer.

As used herein, the term "pendent moiety" refers to a substituent that is linked to the POZ polymer portion via a linking group; a pendent moiety is exemplified by $R_2$ of formula IV as described herein.

As used herein, the term "pharmaceutically acceptable" refers to a compound that is compatible with the other ingredients of a composition and not deleterious to the subject receiving the compound or composition. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

As used herein, the term "pharmaceutically acceptable form" is meant to include known forms of a compound or POZ conjugate that may be administered to a subject, including, but not limited to, solvates, hydrates, prodrugs, isomorphs, polymorphs, pseudomorphs, neutral forms and salt forms of a compound. In certain embodiments, the pharmaceutically acceptable form excludes prodrugs, isomorphs and/or pseudomorphs. In certain embodiments, the pharmaceutically acceptable form is limited to pharmaceutically acceptable salts, neutral forms, solvates and hydrates. In certain embodiments, the pharmaceutically acceptable form is limited to pharmaceutically acceptable salts and neutral forms. In certain embodiments, the pharmaceutically acceptable form is limited to pharmaceutically acceptable salts.

As used herein, the term “alkyl”, whether used alone or as part of a substituent group, is a term of art and refers to saturated aliphatic groups that optionally contain one or more heteroatoms (such as O, S or N) which may be optionally substituted, including straight-chain alkyl groups, branched-chain alkyl groups, cycloalkyl groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer. In certain embodiments, the term “alkyl” refers to a $C_1$-$C_{10}$ straight-chain alkyl group or a $C_1$-$C_3$ straight-chain alkyl group. In certain embodiments, the term “alkyl” refers to a $C_3$-$C_{12}$ branched-chain alkyl group. In certain embodiments, the term “alkyl” refers to a $C_3$-$C_8$ branched-chain alkyl group. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl. In certain embodiments, the term “alkyl” refers to a $C_1$-$C_{10}$ straight-chain alkyl group that contains one or more heteroatoms in place of a carbon atom (such as O, S or N), wherein the heteroatom may be optionally substituted. In certain embodiments, the term “alkyl” refers to a $C_1$-$C_{10}$ straight-chain alkyl group that is substituted with up to 5 groups selected from the group consisting of OH, $NH_2$ and =O.

As used herein, the term “alkenyl”, whether used alone or as part of a substituent group, is a term of art and refers to unsaturated aliphatic groups that optionally contain one or more heteroatoms (such as O, S or N) which may be optionally substituted, including, a straight or branched chain hydrocarbon radical containing from 2 to 30 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

As used herein, the term “alkynyl”, whether used alone or as part of a substituent group, is a term of art and refers to unsaturated aliphatic groups that optionally contain one or more heteroatoms (such as 0, S or N) which may be optionally substituted, including, straight or branched chain hydrocarbon radical containing from 2 to 30 carbon atoms and containing at least one carbon-carbon triple bond. Representative examples of alkynyl include, but are not limited, to acetylenyl, 1-propynyl, 2-propynyl, 3-butynyl, 2-pentynyl, 4-pentynyl, and 1-butynyl.

As used herein, the term “substituted alkyl”, “substituted alkenyl”, and “substituted alkynyl” refers to alkyl, alkenyl and alkynyl groups as defined above in which one or more bonds to a carbon(s) or hydrogen(s) are replaced by a bond to non-hydrogen or non-carbon atoms such as, but not limited to, a halogen atom in halides such as F, Cl, Br, and I; and oxygen atom in groups such as carbonyl, carboxyl, hydroxyl groups, alkoxy groups, aryloxy groups, heterocyclyloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, enamines imines, oximes, hydrazones, heterocyclylamine, (alkyl)(heterocyclyl)-amine, (aryl)(heterocyclyl)amine, diheterocyclylamine, triazoles, and nitriles; a silicon atom in groups such as in trialkylsilyl groups, dialkylarylsilyl groups, alkyldiarylsilyl groups, and triarylsilyl groups; and other heteroatoms in various other groups. In a specific embodiment, a “polar alkyl”, “polar alkenyl”, and “polar alkynyl”, refers to alkyl, alkenyl, and alkynyl groups substituted with an atom that results in a polar covalent bond. In another specific embodiment, a “polar alkyl”, “polar alkenyl”, and “polar alkynyl” refers to C1 to C5 alkyl, alkenyl, and alkynyl, groups substituted with an atom that results in a polar covalent bond. In a specific embodiment, a “polar alkyl”, “polar alkenyl”, and “polar alkynyl”, refers to alkyl, alkenyl, alkynyl groups, such as C1 to C5 alkyl, alkenyl, and alkynyl groups, substituted with an —OH group and/or a —C(O)—OH group.

As used herein, the term “halo” or “halogen” whether used alone or as part of a substituent group, is a term of art and refers to —F, —Cl, —Br, or —I.

As used herein, the term “alkoxy”, whether used alone or as part of a substituent group, is a term of art and refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term “aralkyl” or “arylalkyl”, whether used alone or as part of a substituent group, is a term of art and refers to an alkyl group substituted with an aryl group, wherein the moiety is appended to the parent molecule through the alkyl group. An arylalkyl group may be optionally substituted. A “substituted aralkyl” has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom.

As used herein, the term “heteroaralkyl” or “heteroarylalkyl”, whether used alone or as part of a substituent group, is a term of art and refers to an alkyl group substituted with a heteroaryl group, wherein the moiety is appended to the parent molecular moiety through the alkyl group. A heteroarylalkyl may be optionally substituted. The term “substituted heteroarylalkyl” has the same meaning with respect to unsubstituted heteroarylalkyl groups that substituted aryl groups had with respect to unsubstituted aryl groups.

As used herein, the term “heterocyclylalkyl”, whether used alone or as part of a substituent group, is a term of art and refers to unsubstituted or substituted alkyl, alkenyl or alkynyl groups in which a hydrogen or carbon bond of the unsubstituted or substituted alkyl, alkenyl or alkynyl group is replaced with a bond to a heterocyclyl group. A heterocyclylalkyl may be optionally substituted. The term “substituted heterocyclylalkyl” has the same meaning with respect to unsubstituted heterocyclylalkyl groups that substituted aryl groups had with respect to unsubstituted aryl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

As used herein, the term "aryl", whether used alone or as part of a substituent group, is a term of art and refers to includes monocyclic, bicyclic and polycyclic aromatic hydrocarbon groups, for example, benzene, naphthalene, anthracene, and pyrene. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, the term "aryl" refers to a phenyl group. The aryl group may be optionally substituted.

As used herein, the term "cycloalkyl", whether used alone or as part of a substituent group, is a term of art and refers to a saturated carbocyclic group containing from three to six ring carbon atoms, wherein such ring may optionally be substituted with a substituted or unsubstituted alkyl group or a substituent as described for a substituted alkyl group. Exemplary cycloalkyl groups include, but are not limited to, cyclopropyl, cyclobutyl, cyclopentyl, cyclohexyl, 2-methylcyclobutyl and 4-ethylcyclohexyl.

As used herein, the term "heteroaryl", whether used alone or as part of a substituent group, is a term of art and refers to a monocyclic, bicyclic, and polycyclic aromatic group having 3 to 30 total atoms including one or more heteroatoms such as nitrogen, oxygen, or sulfur in the ring structure. Exemplary heteroaryl groups include azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

As used herein, the term "heterocyclyl", whether used alone or as part of a substituent group, is a term of art and refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 15 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocyclyl group may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like.

As used herein, the terms "treatment", "treat", and "treating" refers a course of action (such as administering a conjugate as described herein or pharmaceutical composition comprising a conjugate as described herein) so as to prevent, eliminate, or reduce a symptom, aspect, or characteristics of a disease or condition. Such treating need not be absolute to be useful. In one embodiment, treatment includes a course of action that is initiated concurrently with or after the onset of a symptom, aspect, or characteristics of a disease or condition. In another embodiment, treatment includes a course of action that is initiated before the onset of a symptom, aspect, or characteristics of a disease or condition.

As used herein, the term "in need of treatment" refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

As used herein, the terms "individual", "subject", or "patient" refers to any animal, including mammals, such as mice, rats, other rodents, rabbits, dogs, cats, swine, cattle, sheep, horses, or primates, and humans. The terms may specify male or female or both, or exclude male or female. In a preferred embodiment, the terms "individual", "subject", or "patient" refers to a human.

As used herein, the term "therapeutically effective amount" refers to an amount of a conjugate, either alone or as a part of a pharmaceutical composition, that is capable of having any detectable, positive effect on any symptom, aspect, or characteristics of a disease or condition. Such effect need not be absolute to be beneficial.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

It will be understood that when a group is specified as a part of a compound, the substitution of the group may be adjusted to accommodate the particular bonds. For example, when an alkyl group is joined to two other groups, the alkyl group is considered an alkylene group.

The term "substituted" is also contemplated to include all permissible substituents of organic compounds. In a broad aspect, the permissible substituents include acyclic and cyclic, branched and unbranched substituents, carbocyclic and heterocyclyl, aromatic and nonaromatic substituents of organic compounds. Illustrative substituents include, for example, those described herein above. For purposes of this disclosure, the heteroatoms, such as oxygen or nitrogen, may have hydrogen substituents and/or any permissible substituents of organic compounds described herein which satisfy the valences of the heteroatoms. Exemplary substitutions include, but are not limited to, hydroxy, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. This invention is not intended to be limited in any manner by the permissible substituents of organic compounds.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of conjugate. As another example, the salt may comprise less than one inorganic or organic acid molecule per molecule of base, such as two molecules of conjugate per inorganic or organic acid molecule.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, iso osmotic, cryo-preservatives, lubricating, flavoring, and coloring agents may be used. Other examples of suitable pharmaceutical carriers are described in *Remington's Science and Practice of Pharmacy* ($23^{rd}$ edition, ISBN 9780128200070) and *Handbook of Pharmaceutical Excipients* ($8^{th}$ edition, 978-0-85-711271-2), each herein incorporated by reference in their entirety.

As used herein, the term "target molecule" refers to any molecule having a therapeutic or diagnostic application or a targeting function, or a vehicle with which a compound is administered or formulated for administration, wherein the target molecule is capable of forming a linkage with an active functional group on a POZ polymer or a POZ derivative of the present disclosure, including, but not limited to, a therapeutic agent (such as but not limited to a drug), a diagnostic agent, a targeting agent, an organic small molecule, an oligonucleotide, a polypeptide, an antibody, an antibody fragment, a protein, a carbohydrate such as heparin or hyaluronic acid, or a lipid such as a glycerolipid, glycolipid, or phospholipid.

As used herein, "lipid" or "lipid portion" means (i) an organic compound that includes an ester of fatty acid or a derivative thereof and is characterized by being insoluble in water, but soluble in many organic solvents, and includes, but is not limited to, simple lipids such as fats, oils, and waxes, compound lipids such as phospholipids, glycolipids, cationic lipids, non-cationic lipids, neutral lipids, and anionic lipids, and derived lipids such as steroids, as well as (ii) an organic compound that does not include an ester of fatty acid, but mimics such an organic compound through its amphipathic character, i.e., it possesses both hydrophobic and hydrophilic portions, and, thus, is able to aggregate in a specific manner to form layers, vesicles and LNPs in aqueous environments.

As used herein, "small interfering RNA (siRNA)" mean a class of double-stranded RNA molecules, 16-40 nucleotides in length, that are involved in the RNA interference (RNAi) pathway, where it interferes with the expression of a specific gene. In addition to their role in the RNAi pathway, siRNAs also act in RNAi-related pathways.

As used herein, "RNA" means a molecule comprising at least one ribonucleotide residue, including siRNA, antisense RNA, single stranded RNA, microRNA, mRNA, noncoding RNA, and multivalent RNA. "Ribonucleotide" means a nucleotide with a hydroxyl group at the 2' position of a β-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution, and/or alteration of one or more nucleotides.

POZ-Lipid Conjugates

The POZ-lipid conjugates of the present disclosure include a lipid portion linked to a polyoxazoline polymer. The components of the POZ-lipid conjugate are discussed in more detail below.

POZ Portion

A variety of POZ polymers may be used in the POZ-lipid conjugates of the present disclosure and are discussed in more detail below. Generally though, the POZ polymer may contain a single type or class of functional groups or may contain more than one type or class of functional groups. The POZ may be a linear POZ polymer, a branched POZ polymer, a pendent POZ polymer or a multi-armed POZ polymer. Representative POZ polymers are described in U.S. Pat. Nos. 7,943,141, 8,088,884, 8,110,651, 8,101,706, 8,883,211, 9,284,411, and U.S. patent application Ser. Nos. 13/003,306, 13/549,312, 13/524,994, each of which is incorporated by reference in its entirety for such teachings. The polyoxazoline polymer may be a homopolymer; likewise, the polyoxazoline polymer may be a random or block copolymer containing one or more units of a first polyoxazoline polymer separated by one or more units of a second polyoxazoline polymer. Likewise, the POZ may be a poly (methyloxazoline) (PMOZ), which is quite hydrophilic, or poly(ethyloxazoline) (PEOZ), which is less hydrophilic.

In one embodiment, the POZ polymer is prepared by living cation polymerization. Other methods known in the art may also be used to prepare the POZ polymer. As discussed in more detail below, the POZ can be conjugated directly to the lipid or may be linked to the lipid via a linker moiety. Any linker moiety suitable for coupling the POZ to a lipid can be used including, but not limited to, non-ester-containing linker moieties and ester-containing linker moieties. And, as discussed in more detail below, the POZ polymer may be conjugated to the lipid portion via an appropriate chemical group on the initiator or the terminal end of the polymer or via an appropriate chemical group at a pendant position on the polymer.

In the present disclosure, whenever a polyoxazoline derivative or polyoxazoline polymer is mentioned, the polyoxazoline polymer may be one characterized with low polydispersity (PD) values and/or increased purity, as such polymers are useful in pharmaceutical applications. In a particular embodiment, the methods of the present disclosure provide for polyoxazoline derivatives with low PD values at increased molecular weight (MW) values. In one embodiment, for example, the POZ portion has a molecular weight of about 500 to about 10000 Daltons. In another embodiment, the POZ portion has a molecular weight of about 500 to about 5,000 Daltons. In still another embodiment, the POZ portion has a molecular weight of about 1,000 Daltons about 2,500 Daltons. In yet another embodiment, the POZ portion has a molecular weight of about 2,000 Daltons to about 5,000 Daltons. In still another embodiment, the POZ portion has a molecular weight of about 5,000 Daltons to about 10,000 Daltons. In such embodiments, at least one polyoxazoline polymer chain has a polydispersity value of less than or equal to 1.2, less than or equal to 1.1, or less than or equal to 1.05. Methods of synthesizing polyoxazoline polymers and derivatives thereof with low PD values are discussed in International Application Nos. PCT/US2008/002626 and PCT/US2008/078159, which are incorporated by reference in their entireties for such teaching.

Lipid Portion

In one embodiment, the lipid portion of the POZ-lipid conjugate includes at least one hydrophobic moiety. In another embodiment, the lipid portion includes two hydrophobic moieties. In this aspect, the hydrophobic moieties may be acyl chains, alkyl chains, or combinations thereof. The acyl and alkyl chains may vary in length. In addition, the acyl and alkyl chains may be saturated or contain one or more areas of unsaturation (such as one or more double bonds).

Regardless of the number of hydrophobic moieties, the lipid portion also includes a chemical group capable of forming a linkage with a chemical group on the POZ polymer. In this aspect, the chemical group may be an amine group, hydroxyl group, aldehyde group, carboxylic acid group, and combinations thereof with other chemical groups not excluded. In one embodiment, the lipid portion may contain a reactive amino group that can be used to form a linkage with the POZ polymer.

In some embodiments, the chemical group on the lipid may be located at the hydrophilic head group position. And, as mentioned above, the POZ polymer may be conjugated to the lipid via an appropriate chemical group on the initiator or the terminal end of the polymer or via an appropriate chemical group at a pendant position on the polymer.

As will be discussed in greater detail below, the nature of the linkage depends on the chemical group present on the POZ polymer and the chemical group present on the lipid portion. In some embodiments, the linkage is degradable in the presence of certain enzymes. In other embodiments, the linkage is stable in the presence of these same enzymes.

In one embodiment, the lipid portion of the POZ-lipid conjugate is a non-charged lipid. For example, any non-charged lipid capable of forming a layer, vesicle and/or LNP composition, either alone or in combination with other lipid components, is suitable for use in forming a POZ-lipid conjugate of the present disclosure. In another embodiment, the lipid portion may be synthetic or naturally occurring.

The lipid portion of the POZ-lipid conjugate may be selected to impart desired characteristics to the LNPs described herein. For example, the degree of unsaturation of the lipid may be selected to provide desired properties to the LNPs described herein. For example, increasing the degree of unsaturation of the lipid portion may impart fluidity to the LNP composition. In addition, a cis configuration around the area of unsaturation may also impart increased fluidity to the LNP composition. Likewise, a saturated lipid portion may impart rigidity to the LNP composition. The fluidity and/or rigidity may be selected to control, at least in part, the stability of the LNP composition and/or the rate of release of a POZ-lipid conjugate from the LNP composition.

In one embodiment, the lipid portion of the POZ-lipid conjugate is a phospholipid. For example, the lipid portion of the POZ-lipid conjugate may be phosphatidyl glycerol (PG), phosphatidyl choline (PC), phosphatidyl ethanolamine (PE), phosphatidic acid (PA), phosphatidyl inositol (PI), phosphatidylserine (PS), or combinations thereof.

In another embodiment, the lipid portion of the POZ-lipid conjugate is a glycerolipid. For example, the lipid portion may be αβ-diacylglycerol.

In a further embodiment, the lipid portion of the POZ-lipid conjugate is a dialkylamine. For example, the lipid portion may be dimyristylamine In a certain aspect, at least one of the two acyl or alkyl chains of the lipid portion in the POZ-lipid conjugate is saturated. In another aspect, each the two acyl or alkyl chains of the lipid in the POZ-lipid conjugate is saturated. In yet another aspect, one of the two acyl or alkyl chains of the lipid in the POZ-lipid conjugate is saturated and the other acyl or alkyl chain is unsaturated. In still another aspect, each the two acyl or alkyl chains of the lipid in the POZ-lipid conjugate is unsaturated. When one or more acyl or alkyl chains of the lipid in the POZ-lipid conjugate are unsaturated, the acyl or alkyl chain may contain from 1 to 6, from 1 to 4, from 1 to 3, or from 1 to 2 areas of unsaturation. The double bond(s), when present, may be in the cis or trans configuration, or a mixture of cis and trans configuration.

In one aspect, at least one of the two acyl or alkyl chains of the lipid in the POZ-lipid conjugate is from 1 to 5 carbons in length, from 6 to 10 carbons in length, from 11 to 16 carbons in length, or from 17-21 carbons in length. In another aspect, each of the two acyl or alkyl chains of the lipid in the POZ-lipid conjugate is from 1 to 5 carbons in length, from 6 to 10 carbons in length, from 11 to 16 carbons in length, or from 17-21 carbons in length. Such acyl or alkyl chains, regardless of the length, include both even and odd chain lengths and may be saturated or unsaturated as described above.

In one particular aspect, at least one of the two acyl or alkyl chains of the lipid portion in the POZ-lipid conjugate is from 6 to 10 carbons in length. In another aspect, each of the two acyl or alkyl chains of the lipid in the POZ-lipid conjugate is from 6 to 10 carbons in length. Such acyl or alkyl chains, regardless of the length, includes both even and odd chain lengths and may be saturated or unsaturated as described above.

In another aspect, at least one of the two acyl or alkyl chains of the lipid portion in the POZ-lipid conjugate is from 11 to 16 carbons in length. In another aspect, each of the two acyl or alkyl chains of the lipid in the POZ-lipid conjugate is from 11 to 16 carbons in length. Such acyl or alkyl chains, regardless of the length, includes both even and odd chain lengths and may be saturated or unsaturated as described above.

In yet another aspect, at least one of the two acyl or alkyl chains of the lipid in the POZ-lipid conjugate is from 17 to 21 carbons in length. In still another aspect, each of the two acyl or alkyl chains of the lipid in the POZ-lipid conjugate is from 17 to 21 carbons in length. Such acyl or alkyl chains, regardless of the length, includes both even and odd chain lengths and may be saturated or unsaturated as described above.

In one aspect, each of the two acyl or alkyl chains of the lipid in the POZ-lipid conjugate is 5, 6, 7, 8, 9, 10, 11, 12, 13, 14, 15, 16, 17, 18, 19, 20, or 21 carbons in length, which acyl or alkyl chains are saturated or unsaturated. In another aspect, each of the two alkyl or acyl chains of the lipid in the POZ-lipid conjugate is an acyl chain of 11, 12, 13, 14, 15, or 16 carbons in length, which acyl chains are saturated or unsaturated. In a further aspect, each of the two acyl or alkyl chains of the lipid in the POZ-lipid conjugate is an acyl chain of 12, 13, 14, or 15 carbons in length, which acyl chains are saturated or unsaturated. In still a further aspect, each of the two acyl or alkyl chains of the lipid in the POZ-lipid conjugate is an acyl chain of 13 or 14 carbons in length, which are acyl chains are saturated or unsaturated. In still another aspect, each of the two alkyl or acyl chains of the lipid in the POZ-lipid conjugate is an alkyl chain of 11, 12, 13, 14, 15, or 16 carbons in length, which alkyl chains are saturated or unsaturated. In a further aspect, each of the two acyl or alkyl chains of the lipid in the POZ-lipid conjugate is an alkyl chain of 12, 13, 14, or 15 carbons in length, which alkyl chains are saturated or unsaturated. In still a further aspect, each of the two acyl or alkyl chains of the lipid in the POZ-lipid conjugate is an alkyl chain of 13 or 14 carbons in length, which are alkyl chains are saturated or unsaturated.

In still another aspect, each acyl or alkyl chain of the lipid portion in the POZ-lipid conjugate has the same length and is unsaturated. For example, the acyl or alkyl chains may be 6, 7, 8, 9, 10, 11, 12, 13, 14, 15, 16, 17, 18, 19, 20, or 21 carbons in length, 11, 12, 13, 14, 15, or 16 carbons in length, 12, 13, 14, or 15 carbons in length, or 13 or 14 carbons in length and unsaturated.

In another aspect, the lipid portion in the POZ-lipid conjugate is 1,2-dimyristoyl-sn-glycerol or 1,2-dilauroyl-sn-glycerol. In still another aspect, the lipid portion in the POZ-lipid conjugate is di(tetradecyl)acetamide or di(dodecyl)acetamide. In yet another aspect, the lipid portion in the POZ-lipid conjugate is N,N-di(tetradecyl)acetamide or N,N-di(dodecyl)acetamide. In still another aspect, the lipid portion may be 1, 2-distearoyl-sn-glycero-3-phosphoethanolamine-poly (ethylene glycol) (DSPE).

POZ-Lipid Conjugate

In general, the covalent attachment of POZ to a lipid is accomplished by reaction of an active chemical group on the POZ polymer with a complementary chemical group on the lipid. The chemical groups on the POZ polymer and/or the lipid may be activated prior to the reaction (such as, but not limited to, removal of any protecting groups). A hydroxyl, amine or carboxyl group may be activated for coupling by monofunctional activating agents, such as N-hydroxysuccinimide, ethylchloroformate, DCCD, Woodward's Reagent K, cyanuric acid and trifluoromethanesulfonyl chloride, among others. A number of bifunctional crosslinking reagents containing groups with different reactivities, such as some diisocyanates, may also be used.

Specific lipids for inclusion in the POZ-lipid conjugates are described above and herein.

In one embodiment, the POZ-Lipid conjugates of the present disclosure may be represented by the general formula I where the lipid is attached to the polymer chain at the terminating terminus:

$$R—POZ_n\text{-}L\text{-}Lipid \qquad I$$

or a pharmaceutically acceptable form thereof, such as, but not limited to, a pharmaceutically acceptable salt, wherein, R is an initiating group;

POZ is a polyoxazoline polymer;

n is 1 to 1,000 and represents the number of monomer units comprising the polyoxazoline polymer;

L is a linking group optionally containing a cleavable moiety in which the rate of cleavage is controlled and represents a direct linkage through a reactive group on the lipid and a reactive group on the polymer, wherein the direct linkage may form a cleavable moiety in which the rate of cleavage can be controlled from highly labile to stable; and Lipid represents a lipid moiety as described herein.

In one embodiment of Structure I, the POZ polymer contains at least one reactive group capable of forming a linkage with a Lipid or a linking group. The linkage (whether a direct linkage or a linkage utilizing a linking group) between the polymer and lipid may be formed between any reactive group on the polymer backbone, including a reactive group at the terminal position or a pendent position (at the terminus), and a reactive group on the lipid. In one aspect, the linkage between the linking group and the polymer may be formed at the terminal end of the polymer. In another aspect, the linkage between the linking group and the polymer may be formed at a pendent position on the polymer. Furthermore, the linkage (whether a direct linkage or a linkage utilizing a linking group) may include components of the reactive group that was originally present on the polymer or the lipid. The linkage (whether a direct linkage or a linkage utilizing a linking group) may be physiologically degradable. In this aspect, the linkage may contain a cleavable moiety. Suitable linking groups include, but are not limited to ethers, esters, amines, amides, and combinations thereof.

In one aspect of this embodiment, L is a stable linkage. In another aspect of this embodiment, L is a physiologically degradable and includes a cleavable moiety. For example, in one embodiment, L may be selected from esters, carboxylate esters (—C(O)—O—), carbonate esters (—O—C(O)—O—), carbamates (—O—C(O)—NH—) and amides (—C (O)—NH—). In yet another aspect of this embodiment, L is a linkage that does not contain a cleavable moiety.

Exemplary R groups include, but are not limited to, hydrogen, alkyl and substituted alkyl. In one embodiment, the initiating group is an alkyl group, such as a C1 to C4 alkyl group. In a specific embodiment of the foregoing, the initiating group is a methyl group. In another embodiment, the initiating group is H. In some aspects, the initiating group may be selected to lack an active functional group. In other aspects, the initiating group may be selected to include an active functional group. Additional suitable initiating groups are disclosed in U.S. Pat. Nos. 7,943,141, 8,088,884, 8,110,651, 8,101,706, 8,883,211, and 9,284,411, and U.S. patent application Ser. Nos. 13/003,306, 13/549,312 and 13/524,994, each of which is incorporated by reference in its entirety for such teachings.

In some embodiments, R is H or $CH_3$.

In one aspect, the POZ polymer in Structure I may be a polymer represented by $[N(COR_2)CH_2CH_2]_n$, wherein $R_2$ is independently selected for each repeating unit of the POZ polymer from an unsubstituted or substituted alkyl, alkenyl, aralkyl and heterocycylalkyl group, and R is H or $CH_3$, and the degree of polymerization "n" may range from 15 to 35, 20 to 30, or 25.

In another aspect, the POZ polymer in Structure I may be a polymer represented by $[N(COR_2)CH_2CH_2]_n$, wherein $R_2$ is independently selected for each repeating unit of the POZ polymer from an unsubstituted and substituted alkyl, and R is H or $CH_3$, and n may range from 15 to 35, 20 to 30, or 25.

In yet another aspect, the POZ polymer in Structure I is a polymer represented by $[N(COR_2)CH_2CH_2]_n$, wherein $R_2$ is independently selected for each repeating unit of the POZ polymer from $—CH_3$ and $—CH_2—CH_3$, and optionally, R is H or $CH_3$, and n may range from 15 to 35, to 30, or 25.

When the POZ polymer is a polymer represented by $[N(COR_2)CH_2CH_2]_n$, the POZ polymer of the conjugate is soluble in aqueous environments. The nature of the pendent groups ($R_2$) can change solubility to some extent. For example, when $R_2$ is methyl (as in PMOZ) the polymer is highly water soluble, and when $R_2$ is ethyl (as in PEOZ) the polymer remains water soluble, but to a lesser extent than PMOZ. The solubility of the POZ polymer permits the POZ polymer to extend beyond the liposomal surface and into the extra-liposomal environment. In such a manner the POZ polymer can effectively shield the liposomal surface.

Specific embodiments of the foregoing Structure I include, but are not limited to, L being an amidase-cleavable amide as shown below in I(a)(1) and I(a)(2):

I(a)(1)

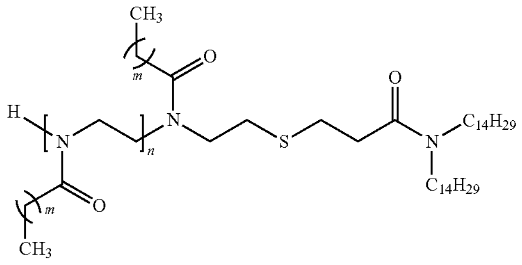

I(a)(2)

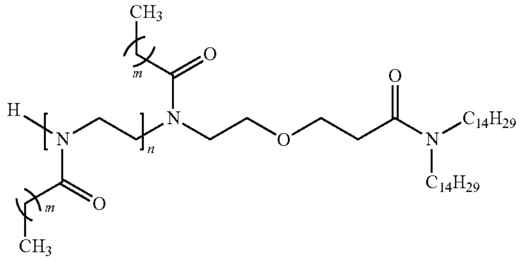

In an alternate embodiment of Structure I, the same lipid group can be incorporated as a stable amine (rather than an amide) as shown below in I(b):

I(b)

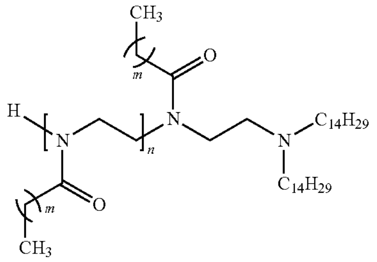

In yet another embodiment of structure I a similar lipid can be coupled via a relatively labile ester linkage as shown below in I(c) and I(d):

I(c)

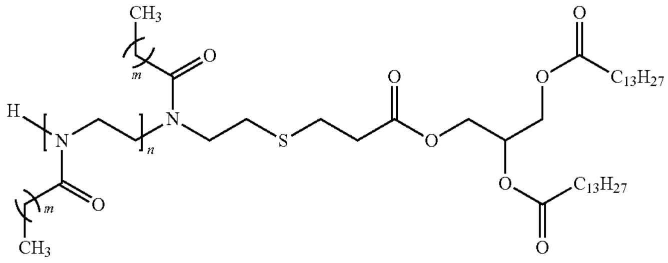

-continued

I(d)

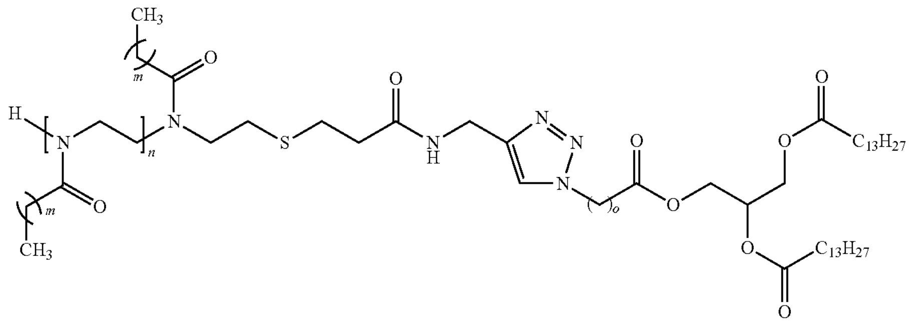

In yet another embodiment of Structure I, a lipid can be coupled via a relatively stable ether linkage as shown below in I(e) and I(f):

I(e)

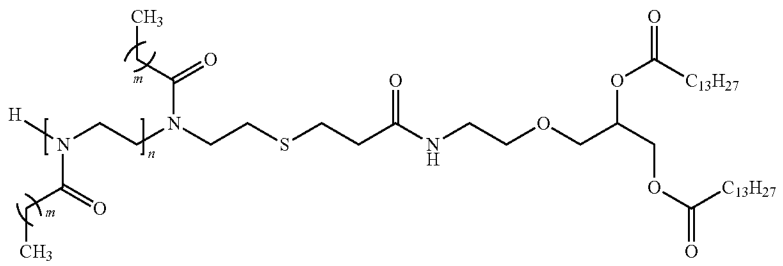

I(f)

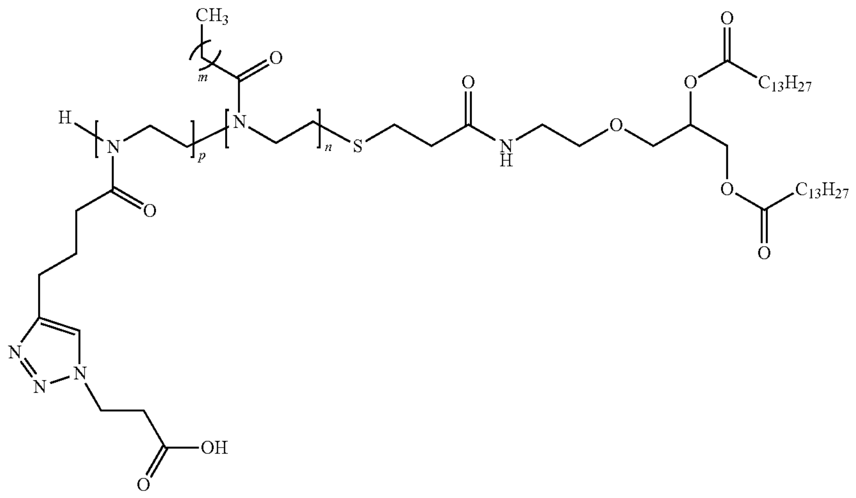

In one embodiment, m is 1 or 2, n ranges from 1 to 1000, o ranges from 1 to 5, and p ranges from 1 to 10 for the Structures I(a)-I(f) (as applicable).

As demonstrated below in the Examples section, the above embodiments of Structure I (I(a)-I(f)) hydrolyze at different rates in plasma, thus illustrating one of the key elements of the novel POZ-lipid conjugates of the present disclosure.

Other specific embodiments of the foregoing Structure I include, but are not limited to, those shown below in I(g) and I(h):

I(g)

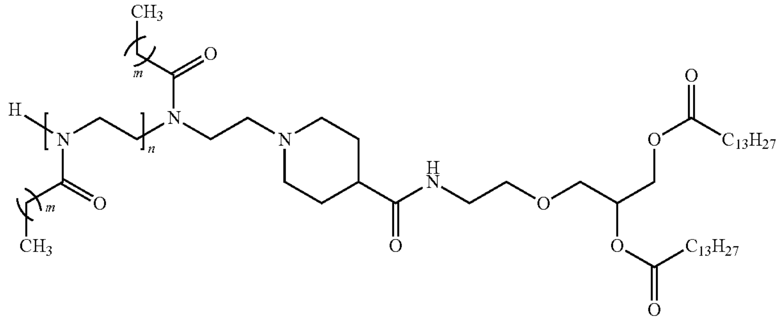

I(h)

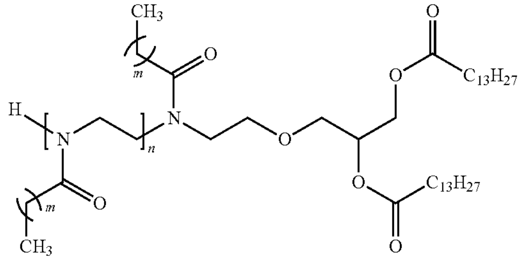

In one embodiment, m is 1 or 2, n ranges from 1 to 1000 for the Structures I(g)-I(h).

In another embodiment of the invention, the POZ-Lipid conjugates of the present disclosure may be represented by the general formula II in which the lipid is attached to the polymer chain at the initiator terminus, rather than the terminating terminus as in formula I:

$$\text{Lipid-}L_1\text{-}(POZ)_n^{a}\text{-}T \qquad \text{II}$$

or a pharmaceutically acceptable form thereof, such as, but not limited to, a pharmaceutically acceptable salt, wherein:

POZ is a polyoxazoline polymer of the structure $[N(COR_2)CH_2CH_2]$;

$L_1$ is a linking group optionally containing a cleavable moiety in which the rate of cleavage can be controlled or represents a direct linkage through a reactive group on the lipid and a reactive group on the polymer, wherein the direct linkage may form a cleavable moiety in which the rate of cleavage can be controlled;

$R_2$ is independently selected for each repeating unit of the polyoxazoline polymer from an unsubstituted or substituted alkyl, alkenyl, alkyne-substituted alkyl, aralkyl, heterocyclylalkyl, or active functional group;

T is a group at the terminating terminus;

a is ran, which indicates a random copolymer, or block, which indicates a block copolymer; and n is an integer from 1 to 1,000.

The nature of the pendent groups ($R_2$) can change solubility to some extent. The solubility of the POZ polymer permits the POZ polymer to extend beyond the liposomal surface and into the extra-liposomal environment. In such a manner, the POZ polymer can effectively shield the liposomal surface and prevent aggregation during LNP formation. In addition, without being bound by any particular theory, it is believed that the POZ-lipid conjugate must be “shed” from the LNP surface after administration in order to efficiently deliver the nucleic acid payload. In certain aspects, addition of highly hydrophilic groups to the POZ-lipid conjugate at the $R_2$ position allows for additional shielding during LNP formation and/or administration and/or enhanced shedding of the POZ-lipid conjugate from the LNP to facilitate delivery of the payload. In one embodiment, $R_2$ includes at least one hydrophilic group. In another embodiment, $R_2$ includes a plurality of hydrophilic groups.

$L_1$ (whether a direct linkage or a linking group) may include components of the reactive group that was originally present on the polymer or the lipid. Suitable linking groups are described herein. $L_1$ may optionally contain a cleavable moiety, such as, but not limited to, esters, carboxylate esters (—C(O)—O—), carbonate esters (—O—C(O)—O—), carbamates (—O—C(O)—NH—) and amides (—C(O)—NH—).

Exemplary active functional groups include, but are not limited to, alkyne, alkene, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). In certain aspects, the active functional group is a hydrophilic group. In certain embodiments, the active functional group is used to add a hydrophilic group to the POZ-lipid conjugate, such as, for example, through click chemistry using an alkyne or an azide active functional group.

In one aspect of this embodiment, $L_1$ is a stable linkage. In another aspect of this embodiment, $L_1$ is physiologically degradable and includes a cleavable moiety. In an alternate aspect of this embodiment, $L_1$ is a linkage that does not contain a cleavable moiety. Suitable $L_1$ linkages are described herein.

In one aspect of this embodiment, $L_1$ is a triazole linking group as discussed in more detail below.

In another aspect of this embodiment, T is a terminating nucleophile. For example, T may be Z—B-Q, wherein Z is S, O, or N; B is an optional linking group; and Q is a terminating nucleophile or a terminating portion of a nucleophile.

B groups may include, but are not limited to, alkylene groups. In a particular embodiment, B is $—(CH_2)_y—$ where y is an integer selected from 1 to 16.

In a particular aspect, Z is S. POZ-lipid conjugates containing a sulfur group as described herein may be prepared by terminating the POZ cation with a mercaptide reagent, such as, but not limited to, a mercapto-ester (for example, $—S—CH_2CH_2—CO_2CH_3$) or mercapto-protected amine (for example, $—S—CH_2CH_2—$NH-tBoc). Such POZ conjugates provide for effective, large-scale purification by ion-exchange chromatography (to remove secondary amines), as well as allowing for control of polydispersity values (with polydispersity values of 1.10 or less) and for the creating of conjugates with higher molecular weight POZ polymers. In another aspect, Z is N. In a further aspect, Z is O.

In certain aspects, Q is inert (i.e., does not contain a functional group). When Q is an inert group, any inert group may be used, including, but not limited to $—C_6H_5$, alkyl, and aryl mercaptide groups. In an alternate aspect, Q is or contains an active functional group. When Q is or contains an active functional group, suitable functional groups include, but are not limited to, alkyne, alkene, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). when Q is or contains an active functional groups, Q may be the same as $R_2$ or Q may be different from $R_2$ (i.e., Q and $R_2$ may be chemically orthogonal to one another).

In one particular aspect of this embodiment, $R_2$ is independently selected for each repeating unit of the polyoxazoline polymer from an unsubstituted or substituted alkyl, and optionally R is H or $CH_3$, and n is 15 to 35, 20 to 30, 22 to 28, or 25. In another aspect of this embodiment, $R_2$ is independently selected for each repeating unit of the polyoxazoline polymer from $CH_3$ and $CH_2—CH_3$, and optionally R is H or $CH_3$, and n is 15 to 35, 20 to 30, 22 to 28, or 25. In any of the foregoing aspects, T is Z—B-Q, wherein Z is S, B is $—(CH_2)_y—$, and Q is an inert group, such as, but not limited to, to $—C_6H_5$, alkyl, and an aryl mercaptide group. Alternatively, in any of the foregoing aspects, T is Z—B-Q, wherein Z is S, B is $—(CH_2)_y—$, and Q is or contains a functional group, such as, but not limited to, alkyne, alkene, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS).

A specific embodiment of the foregoing Structure II includes, but is not limited to, the following structure 11(a) in which the lipid is attached at the initiator terminus while the terminating nucleophile is sulfur:

II(a)

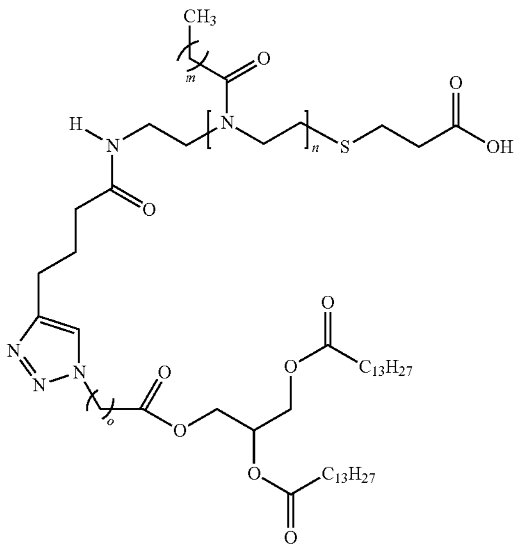

In an alternate embodiment of Structure II as shown below in II(b), the lipid is attached to the initiator terminus while the terminating nucleophile is —OH:

II(b)

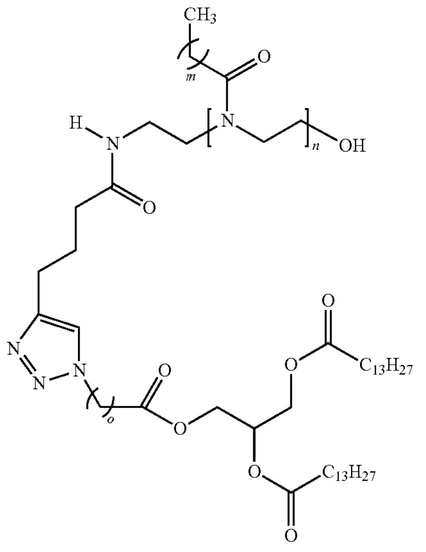

In an alternate embodiment of Structure II shown below in II(c), the lipid is attached to the initiator terminus while the terminating nucleophile is nitrogen, and the lipid is attached via a 2-propionate ester:

II(c)
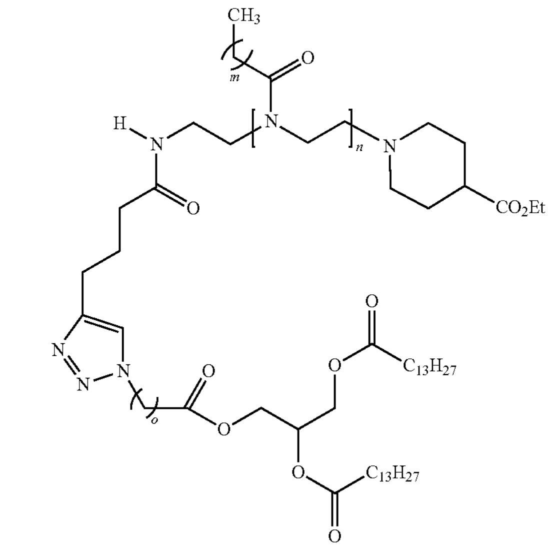
Compounds II(a)-II(c) are made by a "click" reaction of an azide to a pendent alkyne group as shown below:
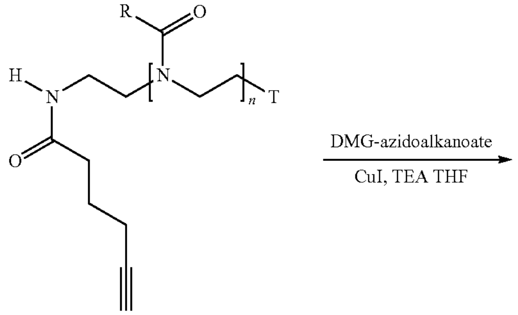
-continued
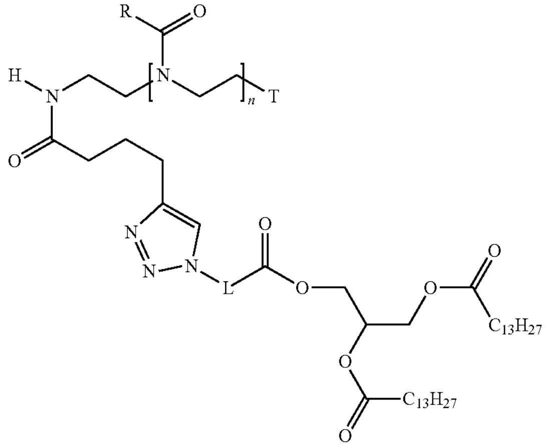
R = Me or Et
T =
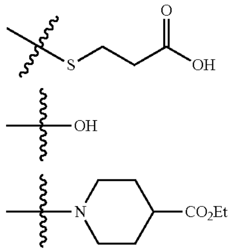
L = $-CH_2-$
$-CH_2(CH_3)-$
$-CH_2CH_2-$
In yet another alternate embodiment of Structure II shown below in II(d), the lipid is attached to the initiator terminus while the terminating nucleophile is sulfur, and the lipid is attached by an acetate ester:
II(d)
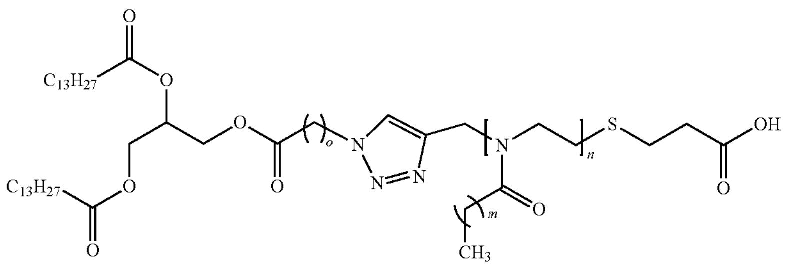

II(d) is made by a "click" reaction of an azide to an alkyne-initiating group as shown below:

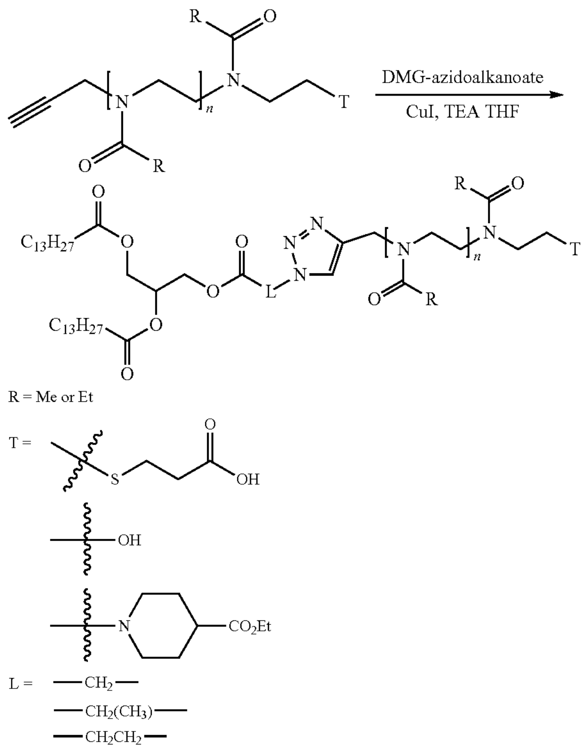

In one embodiment, m is 1-2, n ranges from 1 to 1000, and o ranges from 1 to 5 (as applicable) for Structures II(a)-II(d).

In another embodiment, the POZ-Lipid conjugates of the present disclosure may be represented by the general formula III:

$$R\text{—}(POZ)_n^a\text{—}Z\text{-}L_2\text{-Lipid} \qquad \text{III}$$

or a pharmaceutically acceptable form thereof, such as, but not limited to, a pharmaceutically acceptable salt, wherein:

POZ is a polyoxazoline polymer of the structure $[N(COR_2)CH_2CH_2]$;

$L_2$ is a linking group optionally containing a cleavable moiety in which the rate of cleavage can be controlled or represents a direct linkage through a reactive group on the lipid and a reactive group on the polymer, wherein the direct linkage may form a cleavable moiety in which the rate of cleavage can be controlled;

R is an initiating group;

$R_2$ is independently selected for each repeating unit of the polyoxazoline polymer from an unsubstituted or substituted alkyl, alkenyl, alkyne-substituted alkyl, aralkyl, heterocycylalkyl group, or an active functional group;

Z is S, O, or N;

a is ran, which indicates a random copolymer, or block, which indicates a block copolymer; and n is an integer from 1 to 1,000.

As with Structure II, the nature of the pendent groups ($R_2$) can change solubility to some extent. The solubility of the polyoxazoline polymer permits the polyoxazoline polymer to extend beyond the liposomal surface and into the extra-liposomal environment. In such a manner the polyoxazoline polymer can effectively shield the liposomal surface. In addition, the POZ-lipid conjugate must be "shed" from the LNP surface after administration in order to efficiently deliver the nucleic acid payload. In certain aspects, addition of highly hydrophilic groups to the POZ-lipid conjugate at the $R_2$ position allows for additional shielding during LNP formation and/or administration and/or enhanced shedding of the POZ-lipid conjugate from the LNP to facilitate delivery of the payload.

$L_2$ (whether a direct linkage or a linking group) may include components of the reactive group that was originally present on the polymer or the lipid. Suitable linking groups are described herein. $L_2$ may optionally contain a cleavable moiety, such as, but not limited to, esters, carboxylate esters (—C(O)—O—), carbonate esters (—O—C(O)—O—), carbamates (—O—C(O)—NH—) and amides (—C(O)—NH—).

R groups include, but are not limited to, hydrogen, alkyl and substituted alkyl. In one embodiment, the initiating group is an alkyl group, such as a C1 to C4 alkyl group. In a specific embodiment of the foregoing, the initiating group is a methyl group. In another embodiment, the initiating group is H. The initiating group may be selected to lack an active functional group. Alternatively, the initiating group may be selected to include an active functional group. Additional exemplary initiating groups are disclosed in U.S. Pat. Nos. 7,943,141, 8,088,884, 8,110,651, 8,101,706, 8,883,211, and 9,284,411, and U.S. patent application Ser. Nos. 13/003,306, 13/549,312 and 13/524,994, each of which is incorporated by reference in its entirety for such teachings.

Active functional groups include, but are not limited to, alkyne, alkene, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). In certain aspects, the active functional group is a hydrophilic group. In certain embodiments, the active functional group is used to add a hydrophilic group to the POZ-lipid conjugate, such as, for example, through click chemistry using an alkyne or an azide active functional group.

In one aspect of this embodiment, $L_2$ is a stable linkage. In another aspect of this embodiment, $L_2$ is physiologically degradable and includes a cleavable moiety. In an alternate aspect of this embodiment, $L_2$ is a linkage that does not contain a cleavable moiety. Suitable $L_2$ linkages are described herein.

In a particular aspect, Z is S. POZ conjugates containing a sulfur group as described herein may be prepared by terminating the POZ cation with a mercaptide reagent, such as, but not limited to, a mercapto-ester (for example, —S—$CH_2CH_2$—$CO_2CH_3$) or mercapto-protected amine (for example, —S—$CH_2CH_2$—NH-tBoc). Such POZ conjugates provide for effective, large-scale purification by ion-exchange chromatography (to remove secondary amines), as well as allowing for control of polydispersity values (with polydispersity values of 1.10 or less) and for the creating of conjugates with higher molecular weight POZ polymers. In another aspect, Z is N. In a further aspect, Z is O.

In an aspect of this embodiment, $R_2$ is independently selected for each repeating unit of the polyoxazoline polymer from an unsubstituted or substituted alkyl, and optionally R is H or $CH_3$, and n is n is 15 to 35, 20 to 30, or 25.

In another aspect of this embodiment, $R_2$ is independently selected for each repeating unit of the polyoxazoline polymer from $CH_3$ and $CH_2$—$CH_3$, and optionally R is H or $CH_3$, and n is 15 to 35, 20 to 30, or 25.

In another embodiment, the POZ-Lipid conjugates of the present disclosure may be represented by the general formula IV:

IV

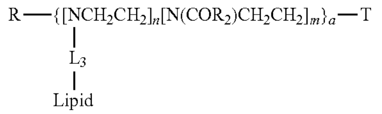

or a pharmaceutically acceptable form thereof, such as, but not limited to, a pharmaceutically acceptable salt, wherein:

R is an initiating group;

$R_2$ is independently selected for each repeating unit of the polyoxazoline polymer from an unsubstituted or substituted alkyl, alkenyl, alkyne-substituted alkyl, aralkyl, heterocycylalkyl group, or an active functional group;

$L_3$ is a linking group optionally containing a cleavable moiety in which the rate of cleavage can be controlled or represents a direct linkage through a reactive group on the lipid and a reactive group on the polymer, wherein the direct linkage may form a cleavable moiety in which the rate of cleavage can be controlled;

Lipid is a lipid;

T is a group at the terminating terminus;

a is ran, which indicates a random copolymer, or block, which indicates a block copolymer;

m is an integer from 1 to 100; and n is an integer from 1 to 5.

In one aspect, n is 1 and this monomer unit is the initial unit adjacent to R.

The nature of the pendent groups ($R_2$) can change solubility to some extent. The solubility of the polyoxazoline polymer permits the polyoxazoline polymer to extend beyond the liposomal surface and into the extra-liposomal environment. In such a manner the polyoxazoline polymer can effectively shield the liposomal surface. In addition, the POZ-lipid conjugate must be "shed" from the LNP surface after administration in order to efficiently deliver the nucleic acid payload. In certain aspects, addition of highly hydrophilic groups to the POZ-lipid conjugate at the $R_2$ position allows for additional shielding during LNP formation and/or administration and/or enhanced shedding of the POZ-lipid conjugate from the LNP to facilitate delivery of the payload.

$L_3$ (whether a direct linkage or a linking group) may include components of the reactive group that was originally present on the polymer or the lipid. Suitable linking groups are described herein. $L_3$ may optionally contain a cleavable moiety, such as, but not limited to, esters, carboxylate esters (—C(O)—O—), carbonate esters (—O—C(O)—O—), carbamates (—O—C(O)—NH—) and amides (—C(O)—NH—).

R groups include, but are not limited to, hydrogen, alkyl and substituted alkyl. In one embodiment, the initiating group is an alkyl group, such as a C1 to C4 alkyl group. In a specific embodiment of the foregoing, the initiating group is a methyl group. In another embodiment, the initiating group is H. The initiating group may be selected to lack an active functional group. Alternatively, the initiating group may be selected to include an active functional group. Additional exemplary initiating groups are disclosed in U.S. Pat. Nos. 7,943,141, 8,088,884, 8,110,651, 8,101,706, 8,883,211, and 9,284,411, and U.S. patent application Ser. Nos. 13/003,306, 13/549,312 and 13/524,994, each of which is incorporated by reference in its entirety for such teachings.

Active functional groups include, but are not limited to, alkyne, alkene, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). In certain aspects, the active functional group is a hydrophilic group. In certain embodiments, the active functional group is used to add a hydrophilic group to the POZ-lipid conjugate, such as, for example, through click chemistry using an alkyne or an azide active functional group.

In one aspect of this embodiment, $L_3$ is a stable linkage. In another aspect of this embodiment, $L_3$ is physiologically degradable and includes a cleavable moiety. In an alternate aspect of this embodiment, $L_3$ is a linkage that does not contain a cleavable moiety. Suitable $L_3$ linkages are described herein.

In one aspect of this embodiment, T is a terminating nucleophile. In one aspect of this embodiment, T is Z—B-Q, wherein Z is S, O, or N; B is an optional linking group; and Q is a terminating nucleophile or a terminating portion of a nucleophile.

B groups include, but are not limited to, alkylene groups. In a particular embodiment, B is —$(CH_2)_y$— where y is an integer selected from 1 to 16.

In a particular aspect, Z is S. POZ conjugates containing a sulfur group as described herein may be prepared by terminating the POZ cation with a mercaptide reagent, such as, but not limited to, a mercapto-ester (for example, —S—$CH_2CH_2$—$CO_2CH_3$) or mercapto-protected amine (for example, —S—$CH_2CH_2$—NH-tBoc). Such POZ conjugates provide for effective, large-scale purification by ion-exchange chromatography (to remove secondary amines), as well as allowing for control of polydispersity values (with polydispersity values of 1.10 or less) and for the creating of conjugates with higher molecular weight POZ polymers. In another aspect, Z is N. In a further aspect, Z is O.

In certain aspects, Q is inert (i.e., does not contain a functional group). When Q is an inert group, any inert group may be used, including, but not limited to —$C_6H_5$, alkyl, and aryl mercaptide groups. In other aspects, Q is or contains an active functional group. When Q is or contains an active functional group, exemplary groups include, but are not limited to, alkyne, alkene, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). When Q is or contains an active functional group, Q may be the same as $R_2$ or Q may be different from $R_2$ (i.e., Q and $R_2$ are chemically orthogonal to one another).

In an aspect of this embodiment, $R_2$ is independently selected for each repeating unit of the polyoxazoline polymer from an unsubstituted or substituted alkyl, and optionally R is H or $CH_3$, m is 15 to 35, 20 to 30, or 25, and n is 1. In another aspect of this embodiment, $R_2$ is independently selected for each repeating unit of the polyoxazoline polymer from $CH_3$ and $CH_2$—$CH_3$, and optionally R is H or $CH_3$, m is 15 to 35, 20 to 30, or 25, and n is 1. In any of these aspects, T is Z—B-Q, wherein Z is S, B is —$(CH_2)_y$—, and Q is an inert groups, such as, but not limited to, to —$C_6H_5$, alkyl, and aryl mercaptide groups. In any of these aspects, T is Z—B-Q, wherein Z is S, B is —$(CH_2)_y$—, and Q is or contains a functional group, such as, but not limited to, alkyne, alkene, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS).

In a specific embodiment of general formula IV, the POZ-lipid conjugates of the present disclosure include the following:

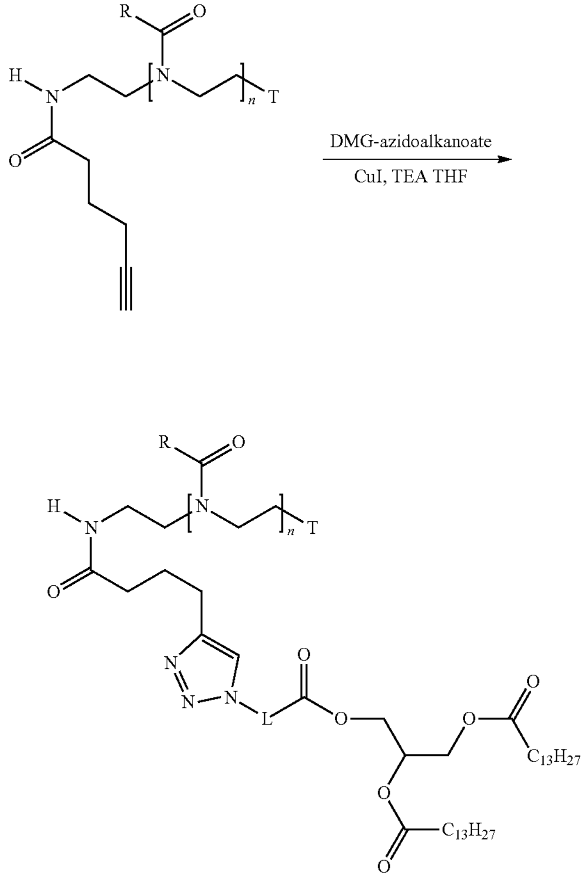

R = Me or Et

T =

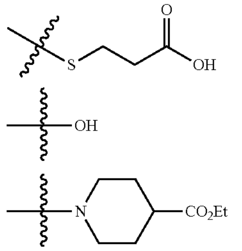

L = —$CH_2$—

—$CH_2(CH_3)$—

—$CH_2CH_2$—

A similar group of compounds is made by coupling an azide to an initiating alkyne group as shown below:

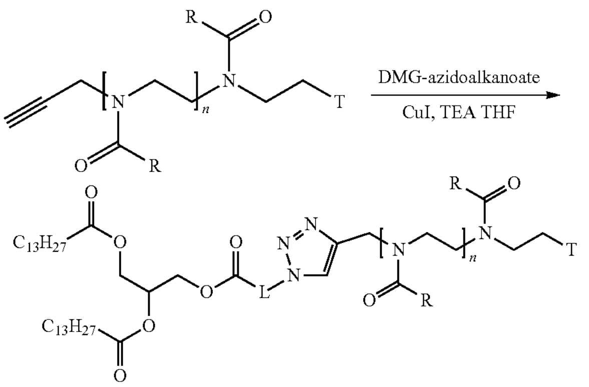

R = Me or Et

T =

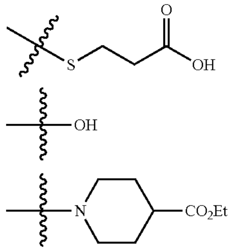

L = —$CH_2$—

—$CH_2(CH_3)$—

—$CH_2CH_2$—

These compounds include a triazole ring. There is evidence that this triazole ring is a privileged scaffold capable of transporting ligands attached to it through the 26S protease, an enzyme responsible for cleavage of polypeptides intracellularly. These so-called proteolysis targeted chimeras (PROTACS) are a promising class of drugs that have been shown to "knockdown" the levels of proteins that bind to one end of the PROTAC and are shuttled through the 26S protease for cleavage. Without being bound to any particular theory, it is contemplated that POZ polymers that incorporate a triazole ring may shuttle POZ polymers through the 26S protease, thus preventing immune presentation of the POZ polymer that does not undergo proteolytic cleavage. Notably, hydrolysis of the degradable ester linkages to release the lipid will leave pendent acid groups attached to the polymer. The inventors have found that soluble POZ with these remaining pendent groups attached via a triazole ring are non-immunogenic, despite being taken up by dendritic cells in the subcutaneous compartment. In addition, labelling studies of a $C^{14}$ labelled 20 kD POZ polymer with rotigotine attached showed that the polymer conjugate was taken up via the lymphatics that drain the subcutaneous injection site. The labelled conjugate eventually appears in the spleen where it is almost selectively taken up by the red pulp (the macrophage compartment). Without being bound by any particular theory, it is contemplated that a POZ-lipid LNP of the present disclosure may also be selectively taken up by dendritic cells. In this same vein, without being bound by any particular theory, it is contemplated that a POZ-lipid LNP of the present disclosure may be selectively taken up by macrophages. If so, then the oligonucleotide payload in the LNP may be expressed preferentially in the dendritic cell/macrophage compartments, which could have implications for immune presentation. It is worthwhile to note that, in one aspect, additional triazole-pendent acids may be directly attached as R groups in the above structures. Without being bound by any particular theory, these groups may further contribute to the reduction of immunogenicity of POZ-lipids contained in LNPs.

Additional POZ-lipid conjugates are represented below in formulas V to VII, wherein the POZ polymer is linked to the lipid by L, $L_1$, $L_2$, or $L_3$:

V

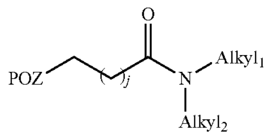

VI

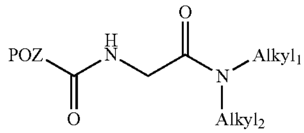

VII

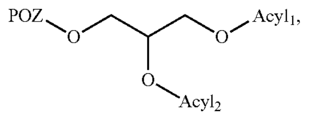

wherein $Alkyl_1$ and $Alkyl_2$ are each independently a saturated or unsaturated alkyl chain of 5, 6, 7, 8, 9, 10, 11, 12, 13, 14, 15, 16, 17, 18, 19, 20, or 21 carbons in length, 11, 12, 13, 14, 15, 16 carbons in length, 12, 13, 14, 15 carbons in length, or 13 or 14 carbons in length; preferably $Alkyl_1$ and $Alkyl_2$ have an equal number of carbon atoms and are each unsaturated;

$Acyl_1$ and $Acyl_2$ are each independently a saturated or unsaturated acyl chain of 5, 6, 7, 8, 9, 10, 11, 12, 13, 14, 15, 16, 17, 18, 19, 20, or 21 carbons in length, 11, 12, 13, 14, 15, 16 carbons in length, 12, 13, 14, 15 carbons in length, or 13 or 14 carbons in length; preferably $Acyl_1$ and $Acyl_2$ have an equal number of carbon atoms and are each unsaturated; and j is an integer from 1 to 8.

Cleavable Linking Group

As discussed above, in some of the embodiments described above, the lipid may be linked to the POZ polymer via a cleavable linkage. In one aspect, a linking group is provided between the POZ polymer and the lipid containing a cleavable moiety. In other words, the linking group contains a linkage that is physiologically degradable in that it can be cleaved in specific environments. For example, the linkage may be cleaved in vivo in a subject after administration of a POZ-lipid conjugate or LNP composition containing a POZ-lipid conjugate of the present disclosure to the subject.

In one embodiment, the cleavable moiety is cleaved by a chemical reaction. In aspect of this embodiment, the cleavage is by reduction of an easily reduced group, such as, but not limited to, a disulfide. In another embodiment, the cleavable moiety is cleaved by a substance that is naturally present or induced to be present in the subject. In an aspect of this embodiment, such a substance is an enzyme or polypeptide. Therefore, in one embodiment, the cleavable moiety is cleaved by an enzymatic reaction. In yet another embodiment, the cleavable moiety is cleaved by a combination of the foregoing. The linking group may contain portions of the POZ polymer and/or portions of the lipid as such portions have reacted to form the linking group as discussed below.

In this aspect, suitable cleavable moieties include, but are not limited to, esters, carboxylate esters (—C(O)—O—), carbonate esters (—O—C(O)—O—), carbamates (—O—C(O)—NH—) and amides (—C(O)—NH—, including an amide group in a peptide); other releasable moieties are discussed herein. In a particular embodiment, the cleavable moiety is an ester. In another particular embodiment, the cleavable moiety is a carbonate ester or a carboxylate ester. In addition, the linking group may be a naturally occurring amino acid, a non-naturally occurring amino acid or a polymer containing one or more naturally occurring and/or non-naturally occurring amino acids. The linking group may include certain groups from the polymer chain and/or the lipid.

In certain aspects of the POZ-lipid conjugates of formulas I to IV, L, $L_1$, $L_2$, and $L_3$ are physiologically degradable linkages that contain a cleavable moiety independently selected for each occurrence from esters, carboxylate esters (—C(O)—O—), carbonate esters (—O—C(O)—O—), carbamates (—O—C(O)—NH—), amides (—C(O)—NH—), and combinations thereof.

In other certain aspects of the POZ-lipid conjugates of formulas I to IV, L, $L_1$, $L_2$, and $L_3$ are independently selected for each occurrence from $—(CH_2)_f$-(cleavable moiety)-$(CH_2)_g—$, wherein f and g are each an integer independently selected from 0-10, 1-9, 1-8, 1-7, 1-6, or 1-5. In one aspect, f and g are each an integer independently selected from 1-4. In another aspect, any of L, $L_1$, $L_2$, and $L_3$ may be a di-substituted triazole as described herein.

In certain aspects of the POZ-lipid conjugates of formulas I to IV, L, $L_1$, $L_2$, and $L_3$ are independently selected for each occurrence from $—(CH_2)_f—C(O)—(CH_2)_g—$, $—(CH_2)_f—C(O)—(CH_2)_h—NHC(O)—(CH_2)_g—$, $—(CH_2)_f—NH(CO)—(CH_2)_h—C(O)—(CH_2)_g—$, $—(CH_2)_f—NHC(O)—(CH_2)_g—$, $—(CH_2)_f—C(O)NH—(CH_2)_g—$, $—(CH_2)_f—NHOC(O)—(CH_2)_g—$, $—(CH_2)_f—OC(O)NH—(CH_2)_g—$, $—(CH_2)_f—OC(O)ONH—(CH_2)_g—$, $—(CH_2)_f—NHOC(O)O—(CH_2)_g—$, $O—(CH_2)_h$, $(CH_2)_h—O$ or $(CH_2)_h$ wherein f, g and h are each an integer independently selected from 0-10, 0-9, 0-8, 0-7, 0-6, or 0-5. In one aspect of this particular embodiment, f, g, and h each may be 0-4.

In another aspect, of the POZ-lipid conjugates of formulas I to IV, L, $L_1$, $L_2$, and $L_3$ are independently selected for each occurrence from a di-substituted triazole that contains a cleavable moiety in one of the $R_3$ or $R_4$ groups. The cleavable moiety is preferably present in the $R_4$ group. In a specific aspect, the di-substituted triazole has the structure:

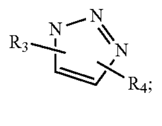

or

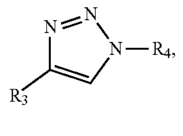

where:

$R_3$ is a linker linking the triazole moiety to the polymer chain. $R_3$ may be defined in part by the functional group on the polymer chain; in other words, $R_3$ may contain a part of the functional group on the polymer chain. In one aspect, $R_3$ is $—C(O)—R_5—$, where $R_5$ is absent or is a substituted or unsubstituted alkyl from 1 to 10 carbons in length.

$R_4$ is a linker linking the triazole moiety to the lipid. $R_4$ may be defined in part by the functional group on the agent; in other words, $R_4$ may contain a part of the functional group on the lipid. In one aspect, $R_4$ is —$R_6$—$R_7$—$R_8$—, where $R_6$ is a substituted or unsubstituted alkyl, substituted or unsubstituted aralkyl, $R_7$ is a group containing the cleavable moiety or a portion of cleavable moiety, and $R_8$ is absent or O, S, $CR_c$, or $NR_c$, where $R_c$ is H or substituted or unsubstituted alkyl. In certain aspects, $R_7$ and $R_8$ may combine to form the cleavable moiety. In one embodiment, $R_7$ is —$R_a$—(O)—$R_b$—, —$R_a$—O—C(O)—$R_b$—, —$R_a$—C(O)—NH-cyclic-O—C(O)—$R_b$— (where cyclic represents substituted or unsubstituted aryl, heterocycloalkyl, heterocycle or cycloalkyl), —$R_a$—C(O)—NH—($C_6H_4$)—O—C(O)—$R_b$—, —$R_a$—C(O)—$R_b$—, —$R_a$—C(O)—O—$R_b$—, —$R_a$—O—C(O)—O—$R_b$—, —$R_a$—O—C(O)—$NR_{15}$—$R_b$— (where $R_{15}$ is a is H or a substituted or unsubstituted C1-C5 alkyl), —$R_a$—CH(OH)—O—$R_b$—, —$R_a$—S—S—$R_b$—, —$R_a$—O—P(O)($OR_{11}$)—O—$R_b$— (where $R_{11}$ is H or a substituted or unsubstituted C1-C5 alkyl), or —$R_a$—C(O)—$NR_{15}$—$R_b$— (where $R_{15}$ is a is H or a substituted or unsubstituted C1-C5 alkyl), where $R_a$ and $R_b$ are each independently absent or substituted or unsubstituted alkyl. In another embodiment, $R_a$ and $R_b$ are each independently absent or a C2-C16 substituted or unsubstituted alkyl. In one embodiment of the foregoing, $R_6$ is a straight chain substituted or unsubstituted C1-C8 alkyl or a branched substituted or unsubstituted C1-C8 alkyl, $R_7$ is —$R_a$—C(O)—O—$R_b$— and $R_8$ is absent. In another embodiment of the foregoing, $R_6$ is a straight chain substituted or unsubstituted C1-C4 alkyl or a branched substituted or unsubstituted C1-C4 alkyl, $R_7$ is —$R_a$—C(O)—O—$R_b$— and $R_8$ is absent. In one embodiment of the foregoing, $R_6$ is, —$CH_2$—, —$CH_2$—$CH_2$—, or —$CH_2(CH_3)$— and $R_7$ is —C(O)—O— and $R_8$ is absent.

In a particular embodiment, $R_3$ is —C(O)—$(CH_2)_3$ and $R_4$ is —$CH_2$—C(O)—O—, —$CH_2$—$CH_2$—C(O)—O— or —$CH_2(CH_3)$—C(O)—O—.

In a particular embodiment, $R_3$ is —C(O)—$(CH_2)_3$ and $R_4$ is —$CH_2$—$CH_2$—O—C(O), —$CH_2$—$CH_2$—$CH_2$—O—C(O), —$CH_2$—$CH_2$—CO—NH—($C_6H_4$)—O—C(O)—.

In certain aspects of the POZ-lipid conjugates of formulas I to IV, L, $L_1$, $L_2$, and $L_3$ are independently selected for each occurrence from one or more of the cleavable moieties described above. In a particular aspect, when more than one L, $L_1$, $L_2$, or $L_3$ linkage are present in a POZ-Lipid conjugate, L, $L_1$, $L_2$, and $L_3$ are each the same. In another particular aspect, when more than one L, $L_1$, $L_2$, or $L_3$ linkage are present in a POZ-Lipid conjugate, at least one L, $L_1$, $L_2$, and $L_3$ is different from the remaining linkages.

Examples 37 and 38 below demonstrate that a number of the POZ-lipids made in accordance with the present disclosure degrade when exposed to plasma enzymes as well as amidases. In particular, ester linkages linking POZ to lipids can be controlled to slow down or speed up cleavage to release lipid from POZ-lipid in plasma. Some of the other POZ-lipids, in particular those with amide linkages, appear not to degrade in plasma, but do degrade when exposed to amidases that are present in certain tissues. Other POZ-lipids, for example those with amine linkages, appear to be stable to both plasma and amidases.

Thus, the present disclosure includes POZ-lipids that are stable in plasma (e.g., amines, amides), POZ-lipids that that can be tuned or controlled to degrade at a desired rate in plasma (e.g., esters), and POZ-lipids that are stable in plasma, but degrade in specific environments. Indeed, substantially precise control of breakdown rate can be provided by carefully selecting the linkage between the POZ and the lipid. In this aspect, the POZ-lipids of the present disclosure may have controllable degradability in physiological media. For example, in one embodiment, the controllable degradability of the linking group results in a POZ-lipid that is stable in physiological media. In this aspect, the rate of hydrolysis of the POZ-lipid, i.e., the time it takes to degrade the POZ-lipid (which is usually measured in terms of its half-life), is an indicator of the stability/degradability of the linkage between the POZ and the lipid. In one aspect, the linking group between the POZ polymer and the lipid enables a POZ-lipid with a hydrolysis half-life in 50 percent human plasma of at least about 120 hours.

In another embodiment, the controllable degradability of the linking group results in a POZ-lipid that degrades over time in physiological media. In certain aspects, the linking group between the POZ polymer and the lipid enables a POZ-lipid with a hydrolysis half-life in 50 percent human plasma of about 10 minutes or less. For example, the linking group between the POZ polymer and the lipid may be selected such that the POZ-lipid has a hydrolysis half-life in 50 percent human plasma of about 3 minutes to about 7 minutes. In other aspects, the linking group between the POZ polymer and the lipid is selected such that the POZ-lipid has a hydrolysis half-life in 50 percent human plasma of about greater than about 10 minutes. For example, the linking group between the POZ polymer and the lipid may be selected such that the POZ-lipid has a hydrolysis half-life in 50 percent human plasma of about 11 minutes to about 8 hours. In one embodiment, the POZ-lipid has a hydrolysis half-life in 50 percent human plasma of about 2 hours to about 5 hours.

Compositions Including POZ-Lipids

Since lipids are amphipathic, i.e., they contain both hydrophobic and hydrophilic portions, these molecules are able to aggregate in a specific manner to form layers, vesicles and LNPs in aqueous environments. For example, phospholipids are a type of lipids that have such amphipathic character, i.e., the head group of a phospholipid is hydrophilic and the tail groups are hydrophobic. The hydrophilic head group contains the negatively charged phosphate group and may contain other polar groups. The hydrophobic tail groups generally comprise long fatty acid hydrocarbon chains. When placed in an aqueous environment, phospholipids form a variety of structures depending on the specific properties of the phospholipid.

Accordingly, POZ-lipids of the present disclosure are particularly well suited to form LNP compositions. And, LNP compositions of the present disclosure incorporating a POZ-lipid conjugate as described herein provide a number of advantages over similar LNP compositions that do not incorporate a POZ-lipid polymer of the disclosure. For example, the LNP compositions of the disclosure are substantially non-immunogenic. In one aspect, POZ-lipid conjugates of the disclosure, when incorporated into LNP compositions as described herein, do not generate a significant immune response, including, but not limited to, the generation of IgM and/or IgG antibodies specific to POZ. In another aspect, POZ-lipid conjugates of the disclosure, when incorporated into LNP compositions as described herein, generate a reduced immune response, including, but not limited to, the generation of IgM and/or IgG antibodies specific to the polymer portion, as compared to a corresponding LNP composition incorporating a PEG-lipid conjugate. In another aspect, after a second administration of a LNP composition including a POZ-lipid conjugate of the disclosure, the LNP composition is present in the blood or a tissue of the subject at a concentration of at least 75%, such as 80%, 85%, 90%, 95%, or greater, as compared to the first administration. In another aspect, a LNP composition including a POZ-lipid conjugate of the present disclosure is not subject to accelerated blood clearance.

Any of the POZ-lipid conjugates of the present disclosure may be used in preparing a LNP composition in accordance with the present disclosure. In one embodiment, a LNP composition may be formed with a POZ-lipid conjugate of the present disclosure and at least one of a cationic or ionizable lipid. For example, a composition may be formed with a POZ-lipid conjugate of the present disclosure and a cationic lipid. In another embodiment, a composition may be formed with POZ-lipid conjugate of the present disclosure and an ionizable lipid. In still another embodiment, a composition in accordance with the present disclosure includes a POZ-lipid conjugate of the present disclosure, a cationic or ionizable lipid and other lipid components (lacking a polyoxazoline component) that are capable of forming vesicles and/or liposomes (underivatized lipids). Examples of suitable underivatized lipids include, but are not limited to, helper lipids and lipids to stabilize the composition.

In one aspect, a LNP formed according to the present disclosure includes a POZ-lipid conjugate of the present disclosure, a cationic or ionizable lipid, and (i) a helper lipid to provide structural support and facilitate endocytosis, and/or (ii) a sterol lipid for stability.

LNPs formed in accordance with the present disclosure may also include a payload. In this aspect, the payload may be an oligonucleotide, protein, or a combination thereof. For example, in a specific embodiment shown in FIG. 1, LNPs of the present disclosure may include (i) an ionizable lipid; (ii) a helper lipid; (iii) a sterol lipid; (iii) a POZ-lipid of the present disclosure; and (iv) an oligonucleotide. In another specific embodiment (not shown), LNPs of the present disclosure may include a cationic lipid, a helper lipid, a sterol lipid, a POZ-lipid of the present disclosure, and an oligonucleotide. In yet another specific embodiment (not shown), LNPs of the present disclosure may include a cationic or ionizable lipid, a helper lipid, a sterol lipid, a POZ-lipid of the present disclosure, and a protein.

In one embodiment, the oligonucleotide comprises DNA, siRNA, self-replicating mRNA, mRNA comprised of modified nucleosides, and mRNA comprised of naturally occurring nucleosides. In one aspect, the oligonucleotide is DNA. In another aspect, the oligonucleotide is siRNA. In still another aspect, the oligonucleotide is self-replicating mRNA, mRNA comprised of modified nucleosides, or mRNA comprised of naturally occurring nucleosides.

In one embodiment, when incorporated in a LNP composition, the POZ-lipid conjugate is present at a mole ratio of about 0.25% to about 5% mole percent in the lipid layer of the LNP composition, at a mole ratio of about 0.5% to about 3% mole percent in the lipid layer of the LNP composition, at a mole ratio of about 0.75% to about 2% mole percent in the lipid layer of the LNP composition, or at a mole ratio of about 0.8% to about 1.5% mole percent in the lipid layer of the LNP composition.

A non-limiting example of a cationic lipid suitable for use in accordance with the present invention is 1,2-dioleoyl-3-trimethylammonium propane (DOTAP). Suitable ionizable lipids include, but are not limited to, MC3 98, Lipid 319, C12-200, 5A2-SC8, 3060i10, Moderna Lipid 5, Moderna Lipid H, SM-102, Acuitas A9 [59], Arcturus Lipid 2,2 (8,8) 4C CH3, Genevant CL1. In one embodiment, the cationic or ionizable lipids have a pKa, as measured by the TNS dye-binding assay, in the range of 6-7.

Helper lipids refer to amphipathic lipids that have hydrophobic and polar head group moieties, and which can form spontaneously into bilayer vesicles in water, as exemplified by phospholipids, or are stably incorporated into lipid bilayers, with the hydrophobic moiety in contact with the interior, hydrophobic region of the bilayer membrane, and the polar head group moiety oriented toward the exterior, polar surface of the membrane. Such helper lipids typically include one or two hydrophobic acyl hydrocarbon chains or a steroid group and may contain a chemically reactive group, such as an amine, acid, ester, aldehyde or alcohol, at the polar head group. Non-limiting examples include phospholipids, such as phosphatidyl choline (PC), phosphatidyl ethanolamine (PE), phosphatidic acid (PA), phosphatidyl inositol (PI), and sphingomyelin (SM), where the two hydrocarbon chains are typically between about 14-22 carbon atoms in length, and have varying degrees of unsaturation. Other suitable helper lipids include, but are limited to, glycolipids, such as cerebrosides and gangliosides. In one aspect, the helper lipid is at least one of 1,2-dioleoyl-sn-glycero-3-phosphoethanolamine (DOPE), 1,2-distearoyl-sn-glycero-3-phosphocholine (DSPC), and POPE (1-palmitoyl-2-oleoylsn-glycero-3-phosphoethanolamine).

A suitable sterol lipid for use in accordance with the present disclosure is cholesterol. In one particular embodiment, a LNP in accordance with the present disclosure includes a cationic or ionizable lipid combined with: (i) DSPC; (ii) cholesterol; (iii) a POZ-lipid of the present disclosure; and (iv) an oligonucleotide.

It is important to note that changes or additions (even very minor) to the LNP compositions of the present disclosure may impact not only the structure of the LNP, but also the delivery of the encapsulated payload. For example, when a sterol lipid such as cholesterol is included in a LNP composition along with an ionizable lipid and a POZ-lipid of the present disclosure, the resulting LNP has a single bilayer. If phytosterol is added, the structure of the LNP becomes more complex and, thus, may deliver the payload differently. In this vein, compositions of the present disclosure including the POZ-lipid conjugates may be unilamellar or non-unilamellar.

The particle size of LNPs made in accordance with the present disclosure can vary. In one embodiment, LNPs formed in accordance with the present disclosure are amphiphilic spherical vesicles formed by one or more lipid bilayers enveloping an aqueous core with size ranging from about 10 nm to about 10 microns. In another embodiment, a LNP formed in accordance with the present disclosure has a particle size of about 25 nm to about 8 microns. In yet another embodiment, a LNP formed in accordance with the present disclosure has a particle size of about nm to about 5 microns. In this aspect, the particle size of the LNP may be between about 20 nm to about 3 microns. In another embodiment, the LNP may be between about 10 nm and about 1000 nm, between about 25 nm and about 500 nm, between about 35 nm and about 250 nm, between about 40 nm and about 150 nm, or between about 45 nm and about 100 nm. Methods of size fractionation are disclosed herein. However, in certain aspects, size fractionation is not required.

The LNP composition of the present disclosure may be prepared by a variety of methods. In one embodiment, the liposomes are prepared by the reverse-phase evaporation method (Szoka et al. PNAS 1978 vol. 75, 4194-4198;

Smirnov et al., Byulleten' Eksperimental'noi Biologii i Meditsiny, 1984, Vol. 98, pp. 249-252; U.S. Pat. No. 4,235,871). In this method, an organic solution of liposome-forming lipids, which may include the polyoxazoline-lipid conjugate, either with or without a linked target molecule, is mixed with a smaller volume of an aqueous medium, and the mixture is dispersed to form a water-in-oil emulsion, preferably using pyrogen-free components. The target molecule to be delivered is added either to the lipid solution, in the case of a lipophilic target molecule, or to the aqueous medium, in the case of a water-soluble target molecule. The lipid solvent is removed by evaporation and the resulting gel is converted to liposomes. The reverse phase evaporation vesicles (REVs) have typical average sizes between about 0.2-0.4 microns and are predominantly oligolamellar, that is, contain one or a few lipid bilayer shells. The REVs may be readily sized, as discussed below, by extrusion to give oligolamellar vesicles having a selected size preferably between about 0.05 to 0.2 microns.

In addition, multilamellar vesicles (MLVs) can be created. In this method, a mixture of liposome-forming lipids, which may include the polyoxazoline-lipid conjugate, either with or without a linked target molecule, as described herein are dissolved in a suitable solvent is evaporated in a vessel to form a thin film. The thin film is then covered by an aqueous medium. The lipid film hydrates to form MLVs. MLVs generally exhibit sizes between about 0.1 to 10 microns. MLVs may be sized down to a desired size range by extrusion and other method described herein.

One effective sizing method for REVs and MLVs involves extruding an aqueous suspension of the liposomes through a polycarbonate membrane having a selected uniform pore size, typically 0.05, 0.08, 0.1, 0.2, or 0.4 microns (Szoka et al. PNAS 1978 vol. 75, 4194-4198).

The pore size of the membrane corresponds roughly to the largest sizes of liposomes produced by extrusion through that membrane, particularly where the preparation is extruded two or more times through the same membrane. Process for sizing MHLVs of larger sizes is provided by Zhu et al. (PLoS One. 2009; 4(4):e5009. Epub 2009 Apr. 6).

When small particle sizes are desired, the REV or MLV preparations can be treated to produce small unilamellar vesicles (SUVs) that are characterized by sizes in the 0.04-0.08 micron range. Such particles may be useful in targeting tumor tissue or lung tissue where the particles may be absorbed through capillary walls (particles larger than 0.1 microns may not be absorbed).

Furthermore, the POZ-lipid conjugate may be introduced into the LNP composition after the liposomes are formed using the techniques described above. In this approach, the preformed liposomes are incubated in the presence of a POZ-lipid conjugate; the POZ-lipid conjugate is incorporated into the liposome by diffusion. The concentration of the POZ-lipid conjugate free in solution or taken up by the liposome may be monitored and the process terminated when a desired concentration of the POZ-lipid conjugate in the LNP composition is reached. The incubation solution may contain surfactants or other agents to facilitate diffusion of the POZ-lipid conjugates into the LNP composition.

The LNP composition may be treated to remove extraneous components prior to use. For example, if surfactants are used as discussed above, the excess surfactants may be removed prior to use. In addition, where a payload, such as an oligonucleotide discussed above, is entrapped in the LNP composition, excess or non-entrapped payload may be removed prior to use. Separation techniques to accomplish this task are known in the art and the particular method selected may depend on the nature of the component to be removed. Suitable methods include, but are not limited to, centrifugation, dialysis and molecular-sieve chromatography. The composition can be sterilized by filtration through a conventional 0.22 micron depth filter.

LNPs can be prepared by the traditional method that involves the hydration of a lipid film containing POZ-lipid conjugate, an ionizable lipid, helper lipids, and cholesterol. This process involves the dissolution of these materials in organic solvent such as chloroform or dichloromethane and then evaporating the solvent to produce a thin film. The film is then hydrated with an aqueous buffer containing the drug or nucleic acid to passively encapsulate the payload. LNPs of heterogeneous particles with a low encapsulation are normally formed, which requires size reduction by extrusion or sonication.

Another suitable technique uses rapid mixing with a microfluidizer. Lipid stock solutions are prepared by dissolving the lipids in an organic solvent, such as ethanol. Aqueous stock solutions contain the nucleic acid dissolved in a buffer solution of known pH, ionic strength and buffer capacity. The two stock solutions are passed through a micromixer at a predetermined rate to allow for the cationic lipid to interact with the negatively charged nucleic acid, resulting in higher encapsulation efficiencies (i.e., >90 percent) and homogeneous size distribution. The aqueous-to-organic solvent ratios during the mixing process is important. The organic solvent is removed by dialysis, tangential flow filtration or centrifugation or other technique. LNPs of defined sizes are produced by controlling the microfluidic operating parameters, resulting in LNPs of low polydispersity and uniform particle size. The average particle diameter (<100 nm), polydispersity (<0.40 and, more particularly, <0.20), and zeta potential of the LNPs are three methods used to characterize the preparation.

The ratio of POZ-lipid to ionic lipid to cholesterol can be varied in order to allow for optimal size, high payload release and transfection, and improved stability of the hydrated formulation. In one embodiment, the mol percent of POZ-lipid in the LNP is about 0.5 to 60 percent. In another embodiment, the mol percent of POZ-lipid is about 1 to about 40 percent. In still another embodiment, the POZ-lipid is present in an amount of about less than 10 percent of the total amount of lipids in the LNP. In this aspect, the POZ-lipid may be present in an amount of about 0.5 to about 5 percent, about 1 to about 4 percent, or about 1.5 to about 3.5 percent. In this aspect, the remainder of the LNP composition may be about 35 to about 50 percent sterol lipid, about 30 percent to about 70 percent cationic lipid, and about 5 percent to about 15 percent helper lipid.

In one embodiment, the LNP composition includes a lipid bilayer encapsulating an aqueous core where the lipid bilayer includes at least one POZ-lipid conjugate, wherein the average molecular weight of the POZ is between about 0.5 and 5 kDa and the aqueous core includes an oligonucleotide. In another embodiment, the LNP composition includes a lipid bilayer encapsulating an aqueous core where the lipid bilayer includes at least one POZ-lipid conjugate, wherein the average molecular weight of the POZ is between about 2 and 5 kDa and the aqueous core includes an oligonucleotide.

The oligonucleotide can be encapsulated into the LNP with a high efficiency. In one embodiment, the oligonucleotide is encapsulated into the LNP with an efficiency of at least 90 percent. In another embodiment, the oligonucleotide is encapsulated into the LNP with an efficiency of about 90 to about 99 percent. In still another embodiment, the oligonucleotide is encapsulated into the LNP with an efficiency of about 90 to about 95 percent. In yet another embodiment, the oligonucleotide is encapsulated into the LNP with an efficiency of greater than about 95 percent.

Administration

The LNPs of the present disclosure may be delivered to a cell. After in vivo administration of the LNPs, the oligonucleotide is released. In this aspect, the LNPs of the present disclosure may be included a pharmaceutical composition capable of eliciting a treatment for a disorder or disease. For example, pharmaceutical compositions including LNPs made in accordance with the present disclosure may be used to prevent or treat infectious diseases including, but not limited to, SARS-CoV-2, rabies, influenza, and others. In addition, pharmaceutical compositions including LNPs made in accordance with the present disclosure may be used as therapeutics for cancer and genetic diseases. Such pharmaceutical compositions may also include a pharmaceutically acceptable carrier in addition to the LNPs.

In one embodiment, a pharmaceutical composition including an effective amount of LNP of the present disclosure can be delivered to an animal. In this aspect, delivery of an effective amount of a LNP of the present disclosure may occur via subcutaneous, intravenous, intramuscular, intradermal or aerosol routes. In one embodiment, the animal is a human.

EXAMPLES

The following non-limiting examples are merely illustrative of the preferred embodiments of the present invention, and are not to be construed as limiting the invention, the scope of which is defined by the appended claims.

Materials 1,2-Dimyristoyl-rac-glycerol (DMG) was purchased from Bachem. PEOZ-propargyl amide 2K, 3-azidopropionyl chloride, 3-(2-aminoethoxy)propane-1,2-diol were synthesized by Serina Therapeutics, Inc. Solketal (1,2-isopropylidineglycerol), myristic acid, copper (I) iodide, triethylamine (TEA), and anhydrous pyridine were purchased from Sigma-Aldrich. Anhydrous sodium sulfate, anhydrous magnesium sulfate, tetrahydrofuran (THF), dichloromethane (DCM), acetonitrile (ACN), and diethyl ether were purchased from EMD Millipore. Sodium chloride (NaCl) was purchased from Fluka. Ambersep M4195 (or Dowex M4195) was purchased from Supelco. SNAP Ultra 25 g column and Isolera System for column purification were purchased from Biotage.

Example 1. Synthesis of PMOZ-dimyristylamide (Compound 15a of 2.2 kD)

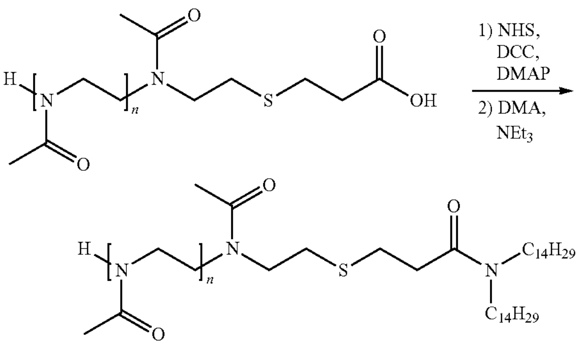

15a

An oven-dried 250-mL round bottomed flask was charged with PMOZ—COOH (12.00 grams, 5.45 mmol, 1.00 equiv) followed by DCM (50 mL), N-hydroxysuccinimide (1.25 grams, 10.9 mmol, 2.00 equiv), and lastly DMAP (0.033 grams, 0.28 mmol, 0.05 equiv) under an atmosphere of Argon. DCC (2.25 g, 10.9 mmol, 2.00 equiv) was added in one portion, and the resulting solution was allowed to stir for at least 12 hours at room temperature. Following this time period, the reaction mixture was filtered through a coarse sintered glass frit, followed by rinsing the frit with additional DCM. The resulting solution was then slowly transferred to a beaker containing a stirred solution of $Et_2O$ (2000 mL). The precipitate was collecting via vacuum filtration, and the solids were dried under vacuum. The solids were then taken up into DCM (50 mL) in a dry 250 mL round bottomed flask equipped with a stir bar under an atmosphere of Argon. The reaction mixture was then charged with dimyristylamine (4.46 g, 10.9 mmol, 2.00 equiv) followed by $NEt_3$ (1.52 mL, 10.9 mmol, 2.00 equiv), and the reaction mixture was allowed to stir for at least 12 hours at room temperature. After this time period had passed, the reaction mixture was precipitated into a beaker containing a stirred solution of 2000 mL diethyl ether. The solids were collected via vacuum filtration and dried under vacuum. The solids were then dissolved in 200 mL deionized water and passed through an amberlite column containing 200 grams Amberlite IR-67 and 200 grams Amberlite IR-120H. The filtrate was collected until the water solution showed a negative PAA test. The resulting solution was then passed through a 1000 mL DEAE column, eluting with deionized water until the PAA test showed a negative result. The resulting water solution was concentrated to dryness on a rotary evaporator. The residue was taken up into dichloromethane (100 mL), dried with sodium sulfate and precipitated into a beaker containing a stirred solution of 2000 mL $Et_2O$. The solids were collected via vacuum filtration and dried under vacuum to afford 10.9 grams of the title compound. 1H NMR analysis showed the standard backbone signals for PMOZ (500 MHz, DMSO) δ 7.92 (m, NH Terminus signal); 3.34 ($CH_2CH_2$ backbone); 3.21 (N—$CH_2$); 2.75-2.72 (S—$CH_2$); 1.98 (—$CH_3$); 1.80 ($CH_2$—$CO_2R$). Additional signals were present for the lipid moiety at δ 1.49-1.41 (N—$(CH_2)_2$); 1.24 ($CH_2$); 0.85 ($CH_3$)

Example 2. PEOZ (2.2 kD)-dimyristylamide—Compound 2b of 2.2 kD

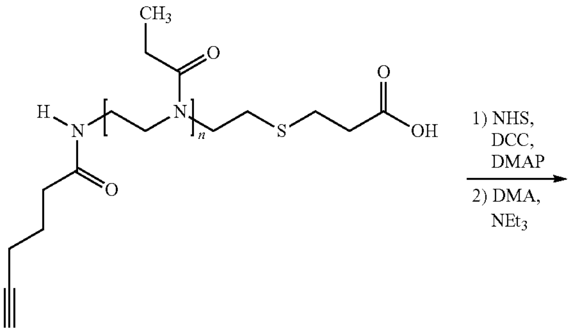

-continued

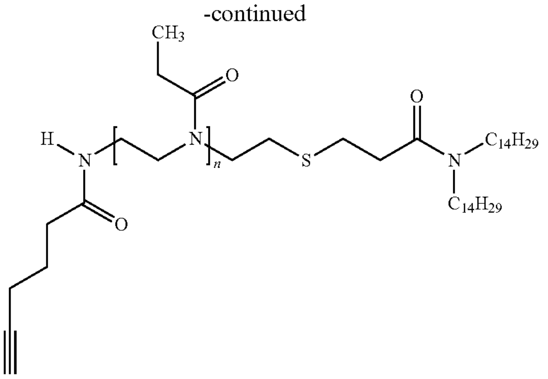

Compound 2B was prepared via the same procedure used to prepare compound 15B. In this iteration, 1.3 grams of material was isolated.

$^1$H NMR. HNMR analysis showed the standard backbone signals for PEOZ (500 MHz, CDCl3) δ 3.64 (CH2CH2 backbone); 3.27 (N—CH2); 2.72 (S—CH2); 2.32-2.19 (C(O)—CH2); 1.12 (CH3). Additional signals were present for the lipid moiety at δ 1.49-1.54 (N—(CH2)2); 1.27 (CH2); 0.87 (CH3). Signals for the pendant group were present at δ 1.65 ppm (CH2). The number of pendant groups was previously calculated from the polymer starting material to be 1.21.

Example 3—Synthesis of PMOZ-dimyristylamide, Compound 16a, 1.3 pendants, 2.2 kD

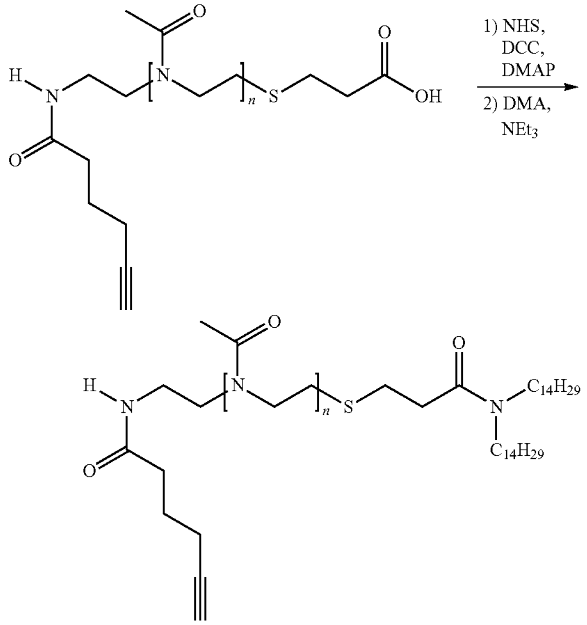

16a

This compound was prepared in an analogous manner to that described above for PMOZ 2.2 kD dymyristylamide. 7.7 g was isolated.

$^1$H NMR analysis showed the standard backbone signals for PMOZ (500 MHz, DMSO) δ 7.90 (m, NH Terminus signal); 3.33 ($CH_2CH_2$ backbone); 3.21 (N—$CH_2$); 2.75-2.72 (S—$CH_2$); 1.98 (—$CH_3$); 1.80 ($CH_2$—$CO_2R$). Additional signals were present for the lipid moiety at δ 1.49-1.41 (N—$(CH_2)_2$); 1.24 ($CH_2$); 0.85 ($CH_3$). Signals for the pendant group were present at δ 1.65 ppm ($CH_2$). The number of pendant groups was calculated via comparison of the integrations of the polymer backbone to the signal for the pendant group. In this case, the number of pendant groups was determined to be 1.35.

Example 4. Synthesis of PEOZ-dimyristylamide, Compound 16b, 1.5 pendants, 2.2 kD

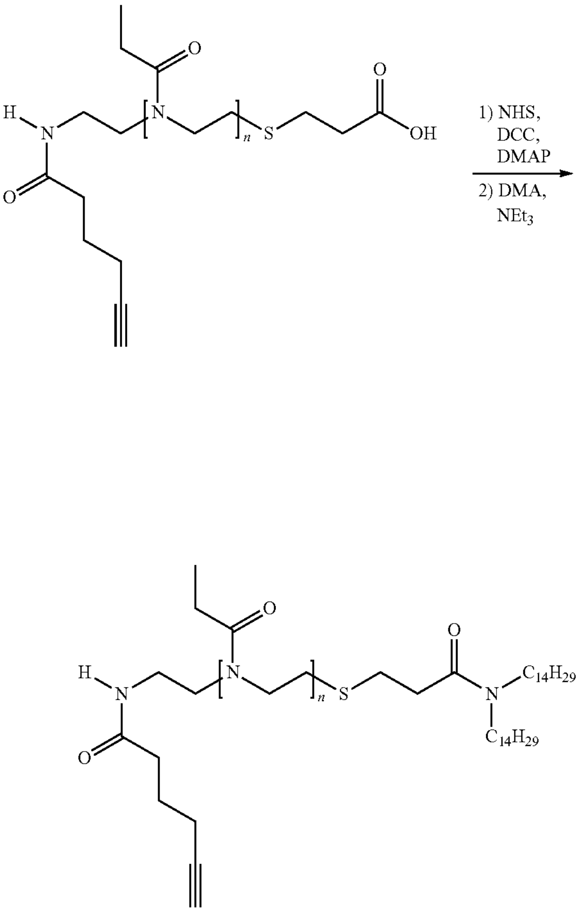

16b

This compound was prepared in an analogous manner to that described above for PEOZ 2.2 kD dymyristylamide. 7.0 g was isolated.

$^1$H NMR analysis showed the standard backbone signals for PEOZ (500 MHz, $CDCl_3$) δ 3.64 ($CH_2CH_2$ backbone); 3.27 (N—$CH_2$); 2.72 (S—$CH_2$); 2.32-2.19 (C(O)—$CH_2$); 1.12 ($CH_3$). Additional signals were present for the lipid moiety at δ 1.49-1.54 (N—$(CH_2)_2$); 1.27 ($CH_2$); 0.87 ($CH_3$). Signals for the pendant group were present at δ 1.65 ppm ($CH_2$). The number of pendant groups was calculated via comparison of the integrations of the polymer backbone to the signal for the pendant group. In this case, the number of pendant groups was determined to be 1.50.

Example 5. Synthesis of PEOZ-dimyristoyl Glycerol ether, Compound 17b, 5 kD

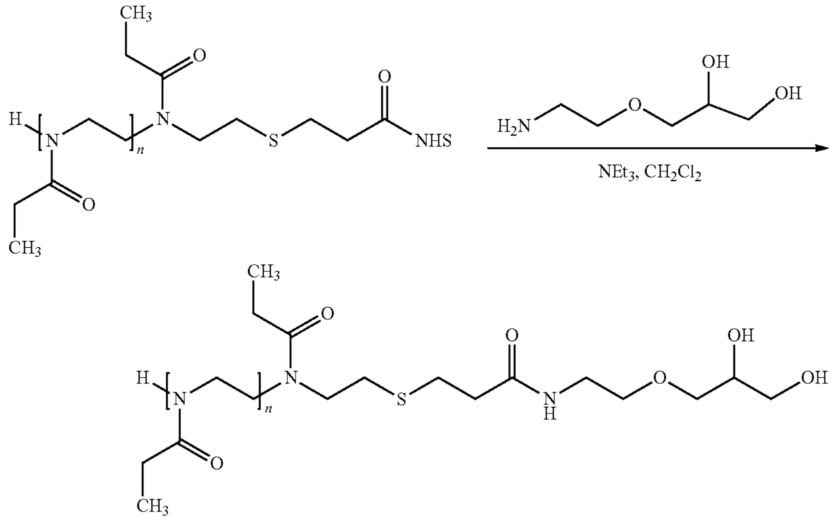

The NHS ester (2.6 grams, 0.49 mmol, 1.00 equiv, synthesized as in U.S. Pat. No. 7,943,141) was taken up into DCM (30 mL) in a dry 250 mL round bottomed flask equipped with a stir bar under an atmosphere of Argon. The reaction mixture was then charged with a solution of the 3-(2-aminoethoxy)propane-1,2-diol (0.200 grams, 1.48 mmol, 3.00 equiv) and $NEt_3$ (0.68 mL, 4.9 mmol, 10 equiv) in 3 mL DMF, and the reaction mixture was allowed to stir for at least 12 hours at room temperature. After this time period had passed, the reaction mixture was precipitated into a beaker containing a stirred solution of 2000 mL diethyl ether. The solids were collected via vacuum filtration and dried under vacuum. 2.3 grams of material was isolated.

$^1H$ NMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). Additional signals were present for the bis-hydroxyamide moiety at δ 4.59 (OH) and 4.46 (OH).

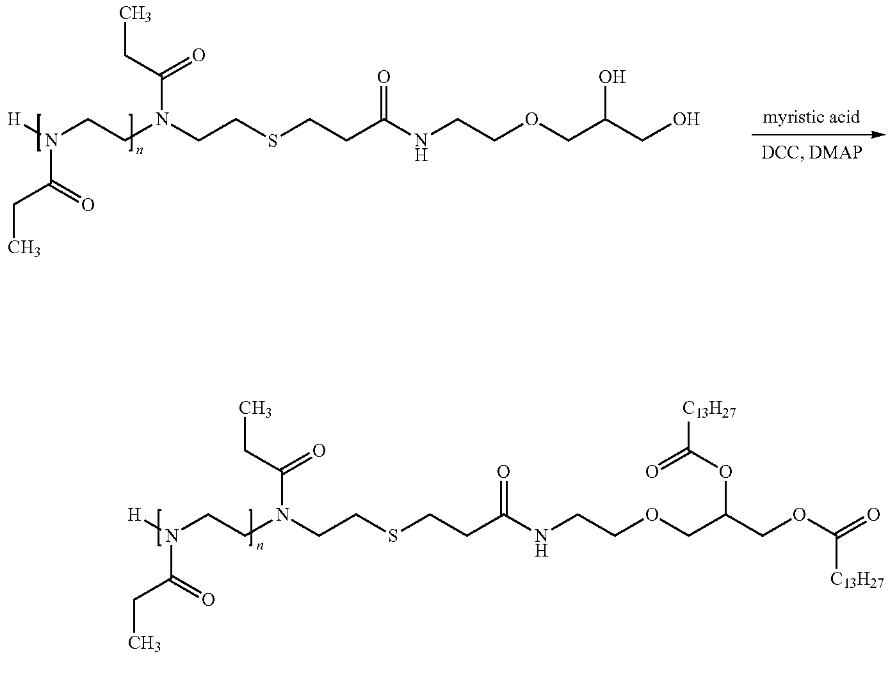

17b

The amide described above (2.3 grams, 0.43 mmol, 1.00 equiv) was charged to a 100 mL round bottomed flask under an atmosphere of argon. The material was dissolved in 30 mL DCM. Myristic acid (0.49 grams, 2.123 mmol, 5.00 equiv) was added followed by DMAP (0.01 g, 0.09 mmol, 0.2 equiv) and lastly DCC (0.44 grams, 2.13 mmol, 5.00 equiv), and the reaction mixture was allowed to stir overnight under an atmosphere of argon. The next morning, the reaction mixture was filtered and precipitated into a beaker containing 1600 mL Diethyl Ether. The solids were collected via vacuum filtration. The product was purified via reverse phase C18 chromatography using acetonitrile and methanol as the eluents to afford the title compound (1.2 grams). 1H NMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). Additional signals were present for the lipid derivative moiety at δ 5.10 (CH); 4.25 ($CH_2$); 4.08 ($CH_2$); 1.48 (C(O)$CH_2$); 1.22 ($CH_2$); 0.84 ($CH_3$)

Example 6. Synthesis of Compound 15b

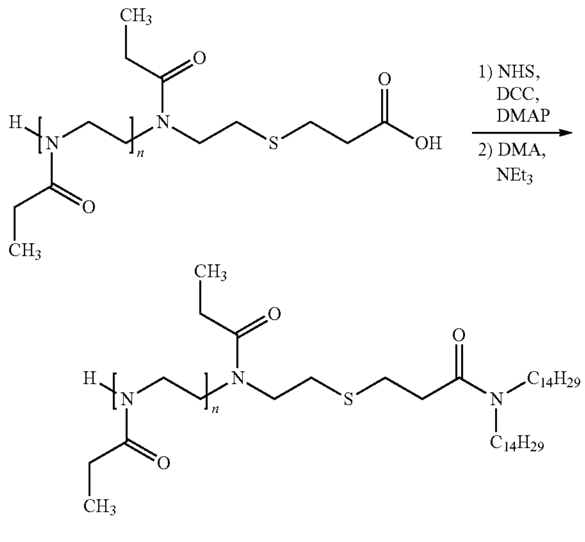

15b

An oven-dried 250-mL round bottomed flask was charged with PEOZ—COOH (7.00 grams, 3.18 mmol, 1.00 equiv) followed by DCM (50 mL), N-hydroxysuccinimide (0.48 grams, 4.14 mmol, 1.30 equiv), and lastly DMAP (0.04 grams, 0.31 mmol, 0.1 equiv) under an atmosphere of Argon. DCC (0.854 g, 4.14 mmol, 1.30 equiv) was added in one portion, and the resulting solution was allowed to stir for at least 12 hours at room temperature. Following this time period, the reaction mixture was filtered through a coarse sintered glass frit, followed by rinsing the frit with additional DCM. The resulting solution was then slowly transferred to a beaker containing a stirred solution of $Et_2O$ (2000 mL). The precipitate was collecting via vacuum filtration, and the solids were dried under vacuum. The solids were then taken up into DCM (50 mL) in a dry 250 mL round bottomed flask equipped with a stir bar under an atmosphere of Argon. The reaction mixture was then charged with dimyristylamine (2.6 g, 6.36 mmol, 2.00 equiv) followed by $NEt_3$ (0.89 mL, 6.36 mmol, 2.00 equiv), and the reaction mixture was allowed to stir for at least 12 hours at room temperature. After this time had passed, the reaction mixture was precipitated into a beaker containing a stirred solution of 2000 mL hexanes. The solids were collected via vacuum filtration and dried under vacuum. The solids were then dissolved in 200 mL deionized water and passed through an amberlite column containing 200 grams Amberlite IR-67 and 200 grams Amberlite IR-120H. The resulting water solution was concentrated to dryness on a rotary evaporator. The residue was taken up into dichloromethane (100 mL), dried with sodium sulfate and concentrated to afford 4.5 grams of the title compound.

$^1H$ NMR analysis showed the standard backbone signals for PEOZ (500 MHz, $CDCl_3$) δ 3.64 ($CH_2CH_2$ backbone); 3.27 (N—$CH_2$); 2.72 (S—$CH_2$); 2.32-2.19 (C(O)—$CH_2$); 1.12 ($CH_3$). Additional signals were present for the lipid moiety at δ 1.49-1.54 (N—$(CH_2)_2$); 1.27 ($CH_2$); 0.87 ($CH_3$)

Example 7. Synthesis of Compound 17a

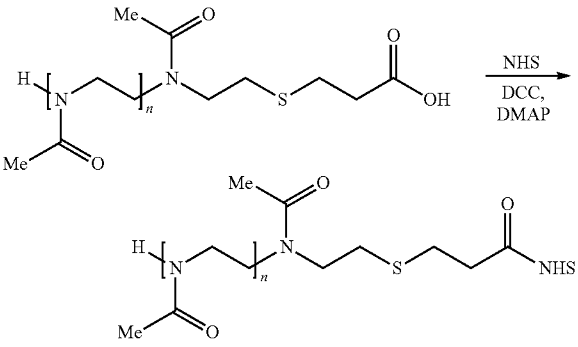

PMOZ 5K NHS ester was prepared in analogous fashion to that described above for PEOZ 5K NHS. 3.0 grams were isolated.

$^1H$ NMR analysis showed the standard backbone signals for PMOZ (500 MHz, DMSO) δ 7.92 (m, NH Terminus signal); 3.34 ($CH_2CH_2$ backbone); 3.21 (N—$CH_2$); 2.75-2.72 (S—$CH_2$); 1.98 (—$CH_3$); 1.80 ($CH_2$—$CO_2R$). Additional signals were present for the NHS moiety at δ 2.81 ($CH_2$).

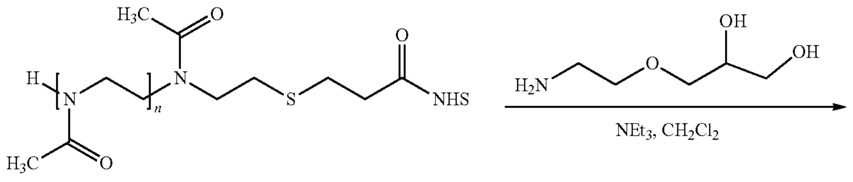

-continued

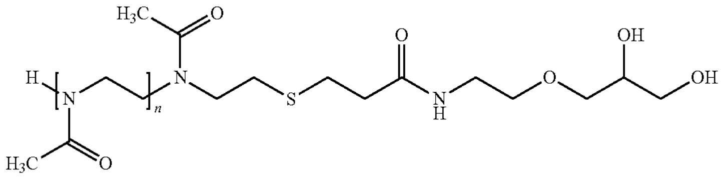

PMOZ 5K amide was prepared in analogous fashion to that described above. HNMR analysis revealed the product material to be an inseparable ~50:50 mixture of the product and the starting NHS ester. This mixture was carried forward to the next step without further purification.

$^{1}H$ NMR analysis showed the standard backbone signals for PMOZ (500 MHz, DMSO) δ 7.92 (m, NH Terminus signal); 3.34 ($CH_2CH_2$ backbone); 3.21 (N—$CH_2$); 2.75-2.72 (S—$CH_2$); 1.98 (—$CH_3$); 1.80 ($CH_2$—$CO_2R$). Additional signals were present for the diol moiety at δ 4.61 (CH) and 4.48 ($CH_2$).

17a

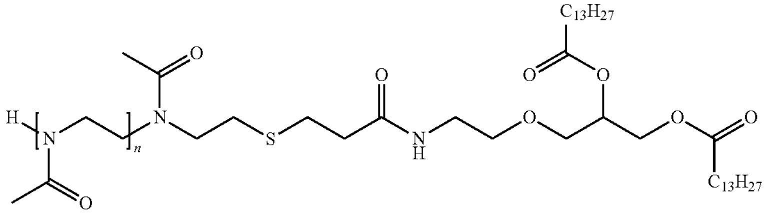

PMOZ 5k Dimyristoyl glycerol ether was prepared in an analogous fashion to that described above. 740 mg were isolated.

$^{1}H$ NMR. HNMR analysis showed the standard backbone signals for PMOZ (500 MHz, DMSO) δ 7.92 (m, NH Terminus signal); 3.34 ($CH_2CH_2$ backbone); 3.21 (N—$CH_2$); 2.75-2.72 (S—$CH_2$); 1.98 (—$CH_3$); 1.80 ($CH_2$—$CO_2R$). Additional signals were present for the lipid derivative moiety at δ 5.10 (CH); 4.26 ($CH_2$); 4.08 ($CH_2$); 1.49 (C(O)$CH_2$); 1.23 ($CH_2$); 0.84 ($CH_3$)

Example 8. Synthesis of Compound 17c

17c

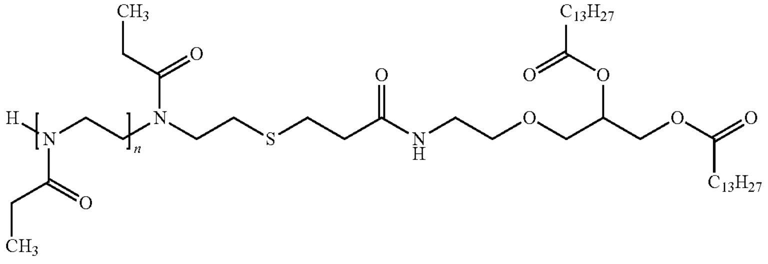

PEOZ 2K Dimyristoyl glycerol ether was prepared in an identical fashion to that described for PEOZ 5K Dimyristoyl glycerol ether.

$^1H$ NMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). Additional signals were present for the lipid derivative moiety at δ 5.10 (CH); 4.25 ($CH_2$); 4.08 ($CH_2$); 1.48 (C(O)$CH_2$); 1.22 ($CH_2$); 0.84 ($CH_3$).

Example 9. Synthesis of Compound 18a

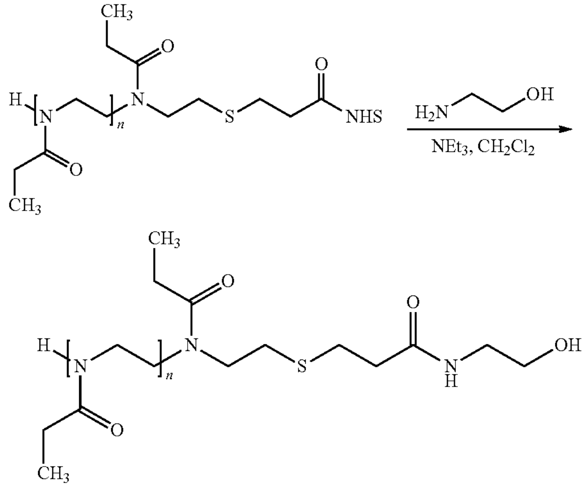

The NHS ester (synthesis previously described, 1.4 grams, 0.67 mmol, 1.00 equiv) was taken up into DCM (30 mL) in a dry 250 mL round bottomed flask equipped with a stir bar under an atmosphere of Argon. The reaction mixture was then charged with ethanolamine (0.15 mL, 2.00 mmol, 3.00 equiv) followed by triethylamine (0.28 mL, 2.00 mmol, 3.00 equiv), and the reaction mixture was allowed to stir for at least 12 hours at room temperature. After this time period had passed, the reaction mixture was precipitated into a beaker containing a stirred solution of 1500 mL diethyl ether. The solids were collected via vacuum filtration and dried under vacuum. 1.1 grams of material was isolated.

$^1H$ NMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). Additional signals were present for the ethanolamine amide at δ 4.63 (OH); 3.08 (N—$CH_2$); 2.69 (HO—$CH_2$).

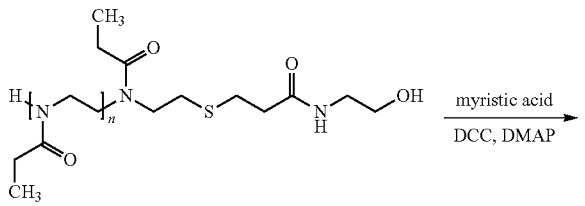

-continued

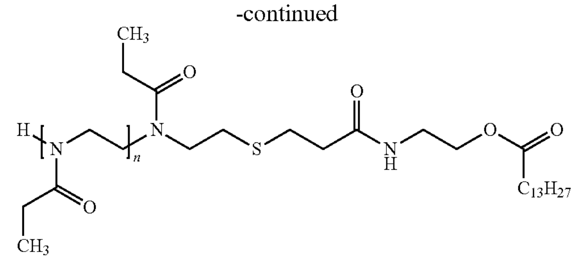

18a

The amide described above (1 gram, 0.45 mmol, 1.00 equiv) was charged to a 100 mL round bottomed flask under an atmosphere of argon. The material was dissolved in 30 mL DCM. Myristic acid (0.52 grams, 2.27 mmol, 5.00 equiv) was added followed by DMAP (0.01 g, 0.09 mmol, 0.2 equiv) and lastly DCC (0.47 grams, 2.27 mmol, 5.00 equiv), and the reaction mixture was allowed to stir overnight under an atmosphere of argon. The next morning, the reaction mixture was filtered and precipitated into a beaker containing 1600 mL diethyl ether. The solids were collected via vacuum filtration. The product was purified via reverse phase C18 chromatography using acetonitrile and methanol as the eluents to afford the title compound (0.740 grams).

$^1H$ NMR analysis showed the standard backbone signals for PEOZ (500 MHz, $CDCl_3$) δ 3.45 ($CH_2CH_2$ backbone); 2.74 (S—$CH_2$); 2.40-2.30 (C(O)—$CH_2$); 1.12 ($CH_3$). Additional signals were present for the lipid moiety at δ 4.10 (O—$CH_2$); 2.85 (N—$CH_2$); 1.99 (lipid $CH_2$); 1.58 (lipid $CH_2$); 1.24 (lipid $CH_2$); 0.87 (lipid $CH_3$).

Example 10. Synthesis of Compound 19a

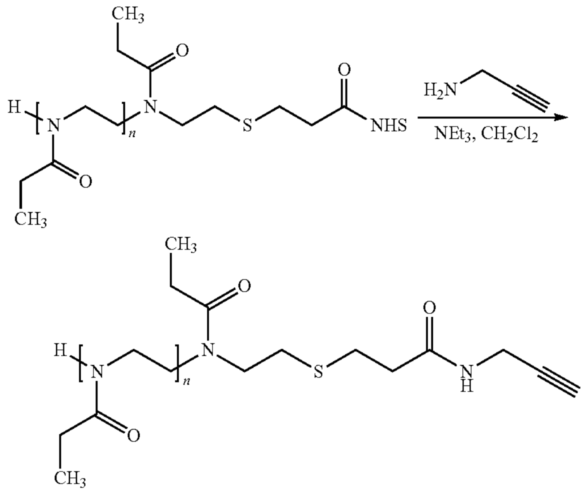

The NHS ester (synthesis previously described, 6.00 grams, 2.86 mmol, 1.00 equiv) was taken up into DCM (100 mL) in a dry 250 mL round bottomed flask equipped with a stir bar under an atmosphere of Argon. The reaction mixture was then charged with propargylamine (0.55 mL, 8.57 mmol, 3.00 equiv) followed by triethylamine (1.19 mL, 8.57 mmol, 3.00 equiv), and the reaction mixture was allowed to stir for at least 12 hours at room temperature. After this time period had passed, the reaction mixture was precipitated into a beaker containing a stirred solution of 2500 mL diethyl ether. The solids were collected via vacuum filtration and dried under vacuum. 1.8 grams of material was isolated.

$^1$H NMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). Additional signals were present for the propargyl amide at δ 3.85 (N—$CH_2$); 3.75 (CCH).

reverse phase C18 chromatography using acetonitrile and methanol as the eluents to afford the title compound (0.540 grams).

$^1$H NMR analysis showed the standard backbone signals for PEOZ (500 MHz, $CDCl_3$) δ 7.71 (NH terminus); 3.45 ($CH_2CH_2$ backbone); 2.72 (S—$CH_2$); 2.40-2.30 (C(O)—$CH_2$); 1.12 ($CH_3$). Additional signals were present for the lipid moiety at δ 5.16 (CH); 4.43 ($CH_2$); 4.11 ($CH_2$); 2.29 (N—$CH_2$); 1.61 (lipid $CH_2$); 1.25 (lipid $CH_2$); 0.88 (lipid

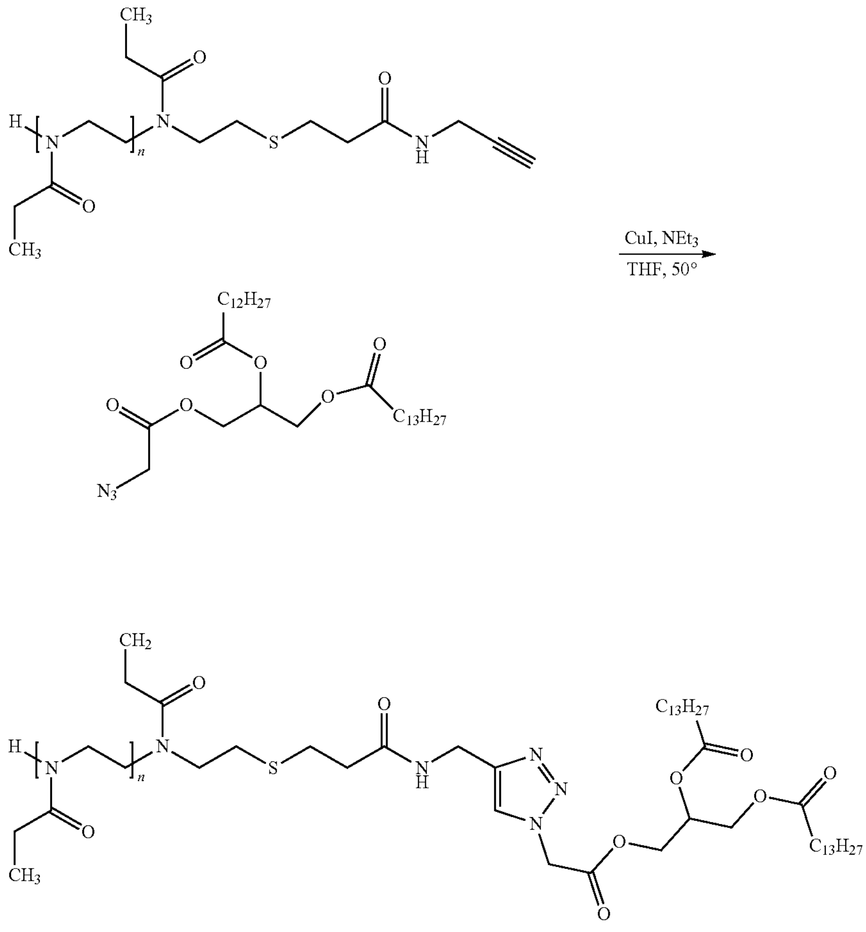

19a

A 100 mL round bottomed flask was charged with the amide described above (0.92 g, 0.44 mmol, 1.00 equiv) followed by the azidoacetate (0.39 g, 0.66 mmol, 1.50 equiv), THE (50 mL), CuI (0.34 g, 1.76 mmol, 4.00 equiv), and lastly triethylamine (0.62 mL, 4.40 mmol, 10.0 equiv). The resulting mixture was heated to 50° C. and stirred overnight. Following this time, the reaction mixture was cooled to room temperature and quenched via addition of 0.1 M HCl (30 mL) and stirred for 10 minutes. The resulting mixture was passed through a pre-prepared 60 mL Dowex column. The resulting solution was concentrated on a rotary evaporator at 35° C. and subsequently transferred to a separatory funnel. Brine (20 mL) was added, and the mixture was extracted 3 times with 20 mL portions of DCM. The combined organic extracts were dried with sodium sulfate and concentrated in vacuo. The product was purified via $CH_3$). Additional signals were present for the triazole moiety at δ 5.29 (triazole CH); 4.53 (ester $CH_2$); 4.23 (HN—$CH_2$).

Example 11. Synthesis of Compound 1b

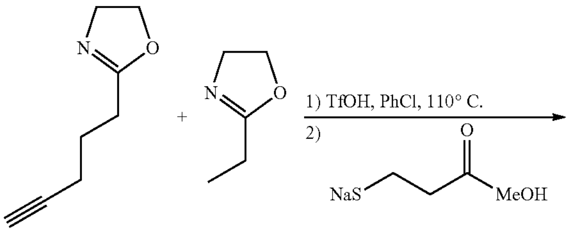

-continued

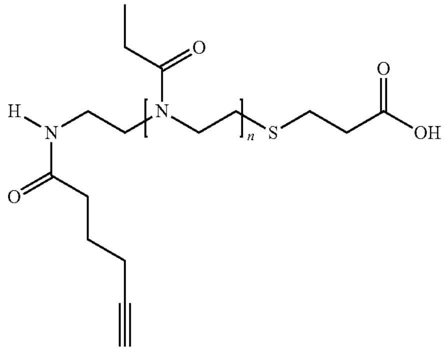

1b

An oven-dried 500 mL round bottomed flask was charged with PhCl (300 mL) followed by a stir bar and 2-(5-pentynyl)-2-oxazoline (5.40 mL, 39.79 mmol, 1.20 equiv) under an atmosphere of Argon. TfOH (2.94 mL, 33.16 mmol, 1.00 equiv) was added dropwise, and the mixture was allowed to stir at room temperature for 10 minutes. Following this time period, 2-ethyl-2-oxazoline (60.15 g, 605.3 mmol, 18.30 equiv) was added, and the resulting mixture was allowed to stir for 10 minutes at room temperature. The reaction was then warmed to 110° C. and stirred for 35 minutes. A separate oven-dried 1000 mL round bottom flask was charged with PhCl (300 mL) followed by NaH (3.97 g, 60% dispersion in oil, 99.22 mmol, 3.00 equiv). Methyl-3-mercaptopropionate (22.00 mL, 198.42 mmol, 6.00 equiv) was then added dropwise, and the mixture was allowed to stir at least 5 hours prior to use. The polymerization mixture was then cooled to room temperature and subsequently transferred to the termination mixture under an atmosphere of Argon over a 10-minute time period. The reaction mixture was allowed to stir for at least 12 hours at room temperature. Following this time, the reaction mixture was concentrated under reduced pressure. 0.1 M $NaOH_{(aq.)}$ (1000 mL) was added, and the mixture was stirred 2 hours. The resulting aqueous solution was passed through a mixed column of Amberlite IRA-67 (200 g) and Amberlite IR120H (200 grams). The product acid was purified via DEAE Sepharose chromatography, and the resulting water solution was acidified to pH=3, extracted with $CH_2C2$ (2×300 mL), and the combined organics were dried with sodium sulfate and concentrated to a volume of 300 mL. The solution was then precipitated into a 4 L beaker containing 3500 mL $Et_2O$, and the solids were collected via vacuum filtration and dried under vacuum to afford 46.2 grams of product. 1H NMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). Signals for the pendant group were present at δ 1.65 ppm ($CH_2$). The number of pendant groups was calculated via comparison of the integrations of the polymer backbone to the signal for the pendant group. In this case, the number of pendant groups was determined to be 1.21.

Example 12. Synthesis of Compound 1a

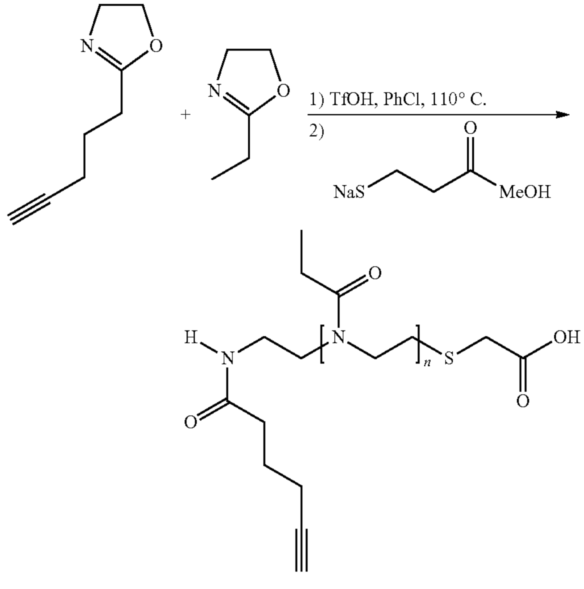

1a

An oven-dried 500 mL round bottomed flask was charged with PhCl (300 mL) followed by a stir bar and 2-(5-pentynyl)-2-oxazoline (2.70 mL, 19.85 mmol, 1.20 equiv) under an atmosphere of Argon. TfOH (1.46 mL, 16.54 mmol, 1.00 equiv) was added dropwise, and the mixture was allowed to stir at room temperature for 10 minutes. Following this time period, 2-ethyl-2-oxazoline (30.0 g, 302.63 mmol, 18.30 equiv) was added, and the resulting mixture was allowed to stir for 10 minutes at room temperature. The reaction was then warmed to 110° C. and stirred for 35 minutes. A separate oven-dried 1000 mL round bottom flask was charged with PhCl (150 mL) followed by NaH (1.98 g, 60% dispersion in oil, 49.61 mmol, 3.00 equiv). Methylthioglycolate (8.86 mL, 99.24 mmol, 6.00 equiv) was then added dropwise, and the mixture was allowed to stir at least 5 hours prior to use. The polymerization mixture was then cooled to room temperature and subsequently transferred to the termination mixture under an atmosphere of Argon over a 10-minute time period. The reaction mixture was allowed to stir for at least 12 hours at room temperature. Following this time, the reaction mixture was concentrated under reduced pressure. 0.1 M $NaOH_{(aq.)}$ (1000 mL) was added, and the mixture was stirred 2 hours. The resulting aqueous solution was passed through a mixed column of Amberlite IRA-67 (200 g) and Amberlite IR120H (200 grams). The product acid was purified via DEAE Sepharose chromatography, and the resulting water solution was acidified to pH=3, extracted with $CH_2Cl_2$ (2×300 mL), and the combined organics were dried with sodium sulfate and concentrated to a volume of 300 mL. The solution was then precipitated into a 4 L beaker containing 3500 mL $Et_2O$, and the solids were collected via vacuum filtration and dried under vacuum to afford 27.6 grams of product.

$^1H$ NMR analysis showed the standard backbone signals for PEOZ (500 MHz, DMSO) δ 7.82 (terminal NH); 3.35 ($CH_2CH_2$ backbone); 3.18 (N—$CH_2$); 2.32-2.27 (C(O)—$CH_2$); 0.96 ($CH_3$). The α-methylene of the terminating group was concluded to lie underneath the signals for the polymer backbone. Signals for the pendant group were present at δ 1.65 ppm ($CH_2$). The number of pendant groups was calculated via comparison of the integrations of the polymer backbone to the signal for the pendant group. In this case, the number of pendant groups was determined to be 1.32.

Example 13. Synthesis of Compound 3a

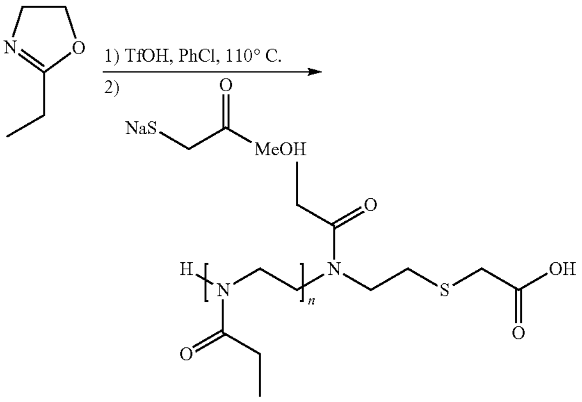

3a

An oven-dried 500 mL round bottomed flask was charged with 2-ethyl-2-oxazoline (32.14 g, 324.22 mmol, 19.00 equiv) followed by PhCl (150 mL) and a stir bar under an atmosphere of argon. TfOH (1.51 mL, 17.06 mmol, 1.00 equiv) was added dropwise, and the mixture was allowed to stir at room temperature for 5 minutes. The reaction was then warmed to 110° C. and stirred for 35 minutes. A separate oven-dried 1000 mL round bottom flask was charged with PhCl (150 mL) followed by NaH (1.91 g, 60% dispersion in oil, 47.8 mmol, 3.00 equiv). Methylthioglycolate (8.55 mL, 95.60 mmol, 6.00 equiv) was then added dropwise, and the mixture was allowed to stir at least 5 hours prior to use. The polymerization mixture was then cooled to room temperature and subsequently transferred to the termination mixture under an atmosphere of argon over a 10-minute time period. The reaction mixture was allowed to stir for at least 12 hours at room temperature. Following this time period, the reaction mixture was concentrated under reduced pressure. 0.1 M $NaOH_{(aq.)}$ (1000 mL) was added, and the mixture was stirred 2 hours. The resulting aqueous solution was passed through a mixed column of Amberlite IRA-67 (200 g) and Amberlite IR120H (200 grams). The product acid was purified via DEAE Sepharose chromatography, and the resulting water solution was acidified to pH=3, extracted with CH2C12 (2×300 mL), and the combined organics were dried with sodium sulfate and concentrated to a volume of 300 mL. The solution was then precipitated into a 4 L beaker containing 3500 mL $Et_2O$, and the solids were collected via vacuum filtration and dried under vacuum to afford 8.0 grams of product.

$^1H$ NMR analysis showed the standard backbone signals for PEOZ (500 MHz, DMSO) δ 7.82 (terminal NH); 3.35 ($CH_2CH_2$ backbone); 3.18 (N—$CH_2$); 2.32-2.27 (C(O)—$CH_2$); 0.96 ($CH_3$). The α-methylene of the terminating group was concluded to lie underneath the signals for the polymer backbone.

Example 14. Synthesis of Compound 4

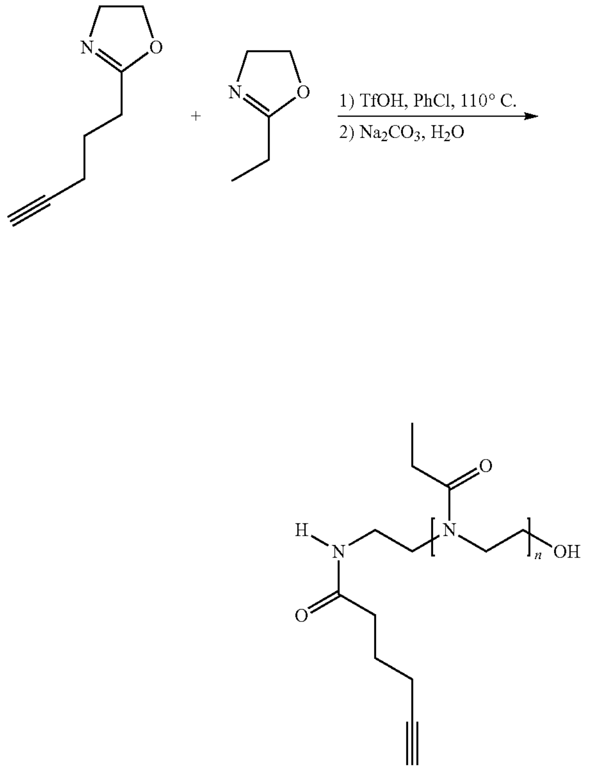

4

An oven-dried 500 mL round bottomed flask was charged with PhCl (300 mL) followed by a stir bar and 2-(5-pentynyl)-2-oxazoline (5.47 mL, 40.27 mmol, 1.20 equiv) under an atmosphere of argon. TfOH (2.97 mL, 33.56 mmol, 1.00 equiv) was added dropwise, and the mixture was allowed to stir at room temperature for 10 minutes. Following this time period, 2-ethyl-2-oxazoline (60.88 g, 614.14 mmol, 18.30 equiv) was added, and the resulting mixture was allowed to stir for 10 minutes at room temperature. The reaction was then warmed to 110° C. and stirred for 35 minutes. The polymerization mixture was then cooled to room temperature and an aqueous solution of $Na_2CO_3$ (22.5 g, 212.3 mmol, 7.00 equiv) in $H_2O$ (400 mL) was added. The reaction mixture was allowed to stir for at least 12 hours. Following this time period, the reaction mixture was transferred to a separatory funnel and diluted with brine (400 mL). The resulting mixture was extracted with $CH_2Cl_2$ (2×300 mL), and the combined organics were concentrated to a volume of 300 mL. The solution was then precipitated into a 4 L beaker containing 3500 mL $Et_2O$, and the solids were collected via vacuum filtration and dried under vacuum to afford 57 grams of product.

$^1H$ NMR analysis showed the standard backbone signals for PEOZ (500 MHz, DMSO) δ 7.82 (terminal NH); 4.83-4.65 ($CH_2CH_2OH$ terminus); 3.35 ($CH_2CH_2$ backbone); 3.18 (N—$CH_2$); 2.32-2.27 (C(O)—$CH_2$); 0.96 ($CH_3$). Signals for the pendant group were present at δ 1.65 ppm ($CH_2$). The number of pendant groups was previously calculated from the polymer starting material to be 1.13.

Example 15. Synthesis of Compound 5

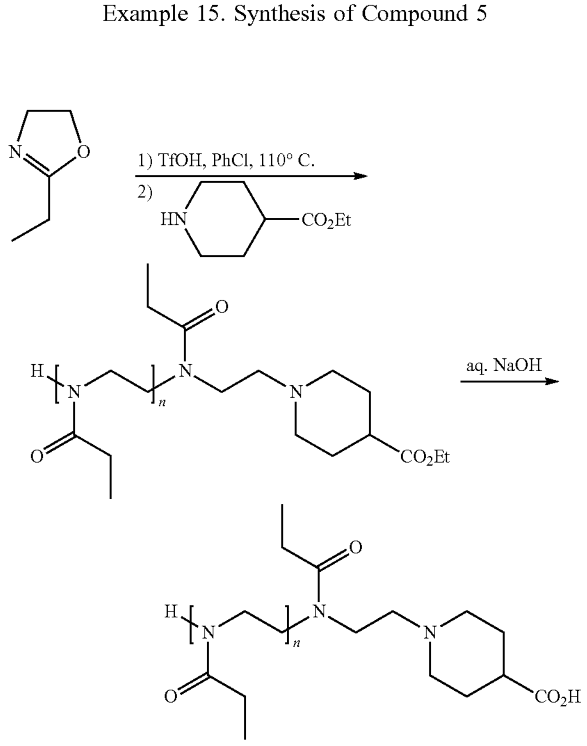

5

An oven-dried 500 mL round bottomed flask was charged with 2-ethyl-2-oxazoline (30.46 g, 307.3 mmol, 19.00 equiv) followed by PhCl (150 mL) and a stir bar under an atmosphere of Argon. TfOH (1.43 mL, 16.17 mmol, 1.00 equiv) was added dropwise, and the mixture was allowed to stir at room temperature for 5 minutes. The reaction was then warmed to 110° C. and stirred for 35 minutes. The polymerization mixture was then cooled to room temperature and Ethyl isonipecotate (4.98 mL, 32.34 mmol, 2.00 equiv) was added. The reaction mixture was allowed to stir for at least 12 hours at room temperature. Following this time period, the reaction mixture was transferred to a separatory funnel and diluted with brine (400 mL). The resulting mixture was extracted with $CH_2Cl_2$ (2×300 mL), and the combined organics were concentrated to a volume of 300 mL. The solution was then precipitated into a 4 L beaker containing 3500 mL of diethyl ether, and the solids were collected via vacuum filtration and dried under vacuum. In this iteration, 25 grams were isolated.

$^1$H NMR analysis showed the standard backbone signals for PEOZ (500 MHz, DMSO) δ 7.82 (terminal NH); 4.05 (ethyl ester $CH_2$); 3.35 ($CH_2CH_2$ backbone); 3.18 (N—$CH_2$); 2.81 ($CH_2$—N); 2.32-2.27 (C(O)—$CH_2$); 2.04 (CH of terminal piperidine); 1.78 ($CH_2$ of terminal piperidine); 1.50 ($CH_2$ of terminal piperidine); 1.16 (ethyl ester $CH_3$); 0.96 ($CH_3$).

From the material collected above, 6.00 grams of the ethyl ester were transferred to a 250 mL round bottomed flask and 1M NaOH$^{(aq.)}$ (30 mL) was added. The reaction mixture was stirred at room temperature for 12 hours, whereupon the mixture was acidified to pH=3. The was removed via rotary evaporation, and the residue was taken up into DMF, filtered, and dried with sodium sulfate, and concentrated in vacuo. The resulting gel was dissolved in $CH_2Cl_2$, dried with sodium sulfate, and concentrated in vacuo. The product was then precipitated into a beaker containing 2000 mL diethyl ether. The solids were collected via vacuum filtration and dried under vacuum. 5.80 grams of material was isolated.

$^1$H NMR analysis showed the standard backbone signals for PEOZ (500 MHz, DMSO) δ 7.82 (terminal NH); 3.35 ($CH_2CH_2$ backbone); 3.18 (N—$CH_2$); 2.96 ($CH_2$—N); 2.32-2.27 (C(O)—$CH_2$); 2.06 (CH of terminal piperidine); 1.86 ($CH_2$ of terminal piperidine); 0.96 ($CH_3$).

Example 16. Synthesis of Compound 7

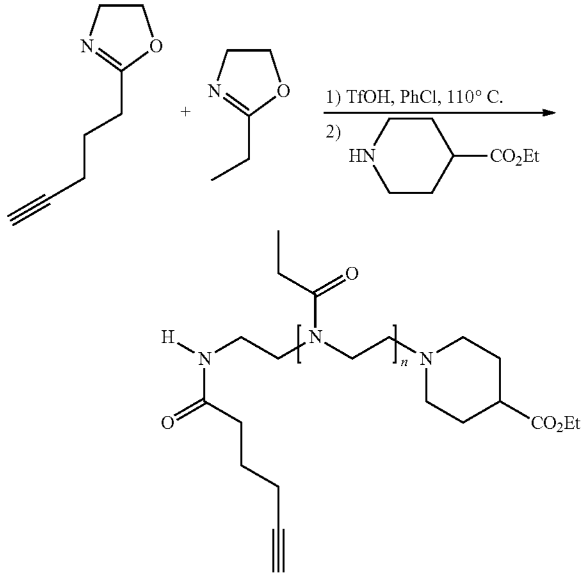

7

An oven-dried 500 mL round bottomed flask was charged with PhCl (150 mL) followed by a stir bar and 2-(5-pentynyl)-2-oxazoline (2.7 mL, 19.85 mmol, 1.20 equiv) under an atmosphere of Argon. TfOH (1.46 mL, 16.54 mmol, 1.00 equiv) was added dropwise, and the mixture was allowed to stir at room temperature for 10 minutes. Following this time period, 2-ethyl-2-oxazoline (30.00 g, 302.6 mmol, 18.30 equiv) was added, and the resulting mixture was allowed to stir for 10 minutes at room temperature. The reaction was then warmed to 110° C. and stirred for 35 minutes. The polymerization mixture was then cooled to room temperature. Ethyl isonipecotate (4.98 mL, 33.08 mmol, 2.00 equiv) was then added. The reaction mixture was allowed to stir for at least 12 hours at room temperature. Following this time period, the reaction mixture was transferred to a separatory funnel and diluted with brine (400 mL). The resulting mixture was extracted with $CH_2Cl_2$ (2×300 mL), and the combined organics were concentrated to a volume of 300 mL. The solution was then precipitated into a 4 L beaker containing 3500 mL Et2O, and the solids were collected via vacuum filtration and dried under vacuum. 25 grams of material was isolated.

$^1$H NMR analysis showed the standard backbone signals for PEOZ (500 MHz, DMSO) δ 7.82 (terminal NH); 4.05 (ethyl ester $CH_2$); 3.35 ($CH_2CH_2$ backbone); 3.18 (N—$CH_2$); 2.81 ($CH_2$—N); 2.32-2.27 (C(O)—$CH_2$); 2.04 (CH of terminal piperidine); 1.78 ($CH_2$ of terminal piperidine); 1.50 ($CH_2$ of terminal piperidine); 1.16 (ethyl ester $CH_3$); 0.96 ($CH_3$). Signals for the pendant group were present at δ 1.65 ppm ($CH_2$). The number of pendant groups was previously calculated from the polymer starting material to be 0.9.

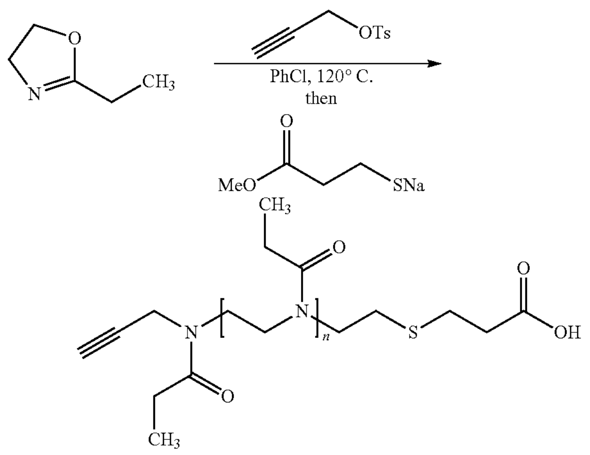

8

Example 17. Synthesis of Compound 8

An oven-dried 500 mL round bottomed flask was charged with chlorobenzene (150 mL) followed by a stir bar and 2-ethyl-2-oxazoline (30 g, 302.63 mmol, 19.00 equiv) under an atmosphere of argon. Propargyl tosylate (2.76 mL, 15.93 mmol, 1.0 equiv) was added, and the reaction mixture was warmed to 110° C. and stirred for 40 minutes. A separate oven-dried 1000 mL round bottom flask was charged with chlorobenzene (150 mL) followed by NaH (1.91 g, 60% dispersion in oil, 47.79 mmol, 3.00 equiv). Methyl-3-mercaptopropionate (10.48 mL, 95.58 mmol, 6.00 equiv) was then added dropwise, and the mixture was allowed to stir for 5 hours. The polymerization mixture was then cooled to room temperature following a 40-minute hold time and subsequently transferred to the termination mixture under an atmosphere of argon over a 10-minute time period. The reaction mixture was allowed to stir for 12 hours at room temperature. Following this time period, the reaction mixture was concentrated under reduced pressure. 0.1 M $NaOH_{(aq.)}$ (1000 mL) was added, and the mixture was stirred 2 hours. The resulting aqueous solution was passed through a mixed column of Amberlite IRA-67 (200 g) and Amberlite IR120H (200 grams). The product acid was purified via DEAE Sepharose chromatography, and the resulting water solution was acidified to pH 3, extracted with $CH_2Cl_2$ (2×300 mL), and the combined organics were dried with sodium sulfate and concentrated to a volume of 300 mL. The solution was then precipitated into a 4 L beaker containing 3500 mL $Et_2O$, and the solids were collected via vacuum filtration and dried under vacuum to afford 15.2 grams of product. An analytical purity of 98% was determined via HPLC analysis.

$^1H$ NMR analysis showed the standard backbone signals for PEOZ (500 MHz, DMSO) δ 3.35 ($CH_2CH_2$ backbone); 3.18 (N—$CH_2$); 3.02 (S—$CH_2$); 2.32-2.27 (C(O)—$CH_2$); 0.96 ($CH_3$). Signals for the alkynyl group were present at δ 4.22-3.82 ppm ($CH_2$ and CH).

Example 18. Synthesis of Compound 9

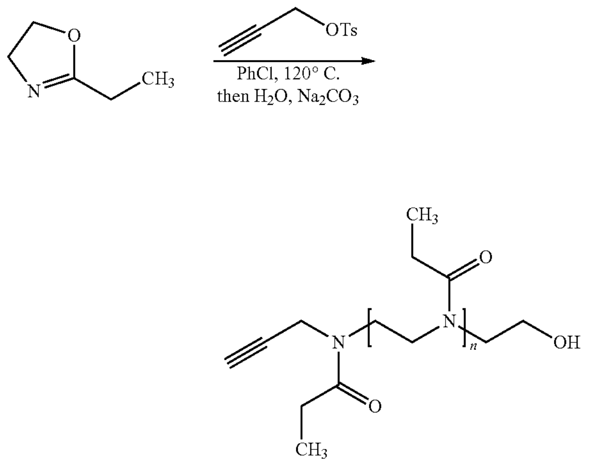

9

An oven-dried 500 mL round bottomed flask was charged with PhCl (75 mL) followed by a stir bar and 2-ethyl-2-oxazoline (15.41 g, 155.47 mmol, 20.00 equiv) under an atmosphere of Argon. Propargyl tosylate (1.34 mL, 7.77 mmol, 1.0 equiv) was added, and the reaction mixture was warmed to 110° C. and stirred for one hour. The reaction mixture was then cooled to room temperature and an aqueous solution of $Na_2CO_3$ (6.00 g, 57.00 mmol, 7.00 equiv) in $H_2O$ (100 mL) was added. The reaction mixture was allowed to stir for at least 12 hours. Following this time period, the reaction mixture was transferred to a separatory funnel and diluted with brine (200 mL). The resulting mixture was extracted with $CH_2Cl_2$ (2×200 mL), and the combined organics were concentrated to a volume of 15000 mL. The solution was then precipitated into a 4 L beaker containing 2000 mL $Et_2O$, and the solids were collected via vacuum filtration and dried under vacuum to afford 6.05 grams of product.

$^1H$ NMR analysis showed the standard backbone signals for PEOZ (500 MHz, DMSO) δ 4.83-4.65 ($CH_2CH_2OH$ terminus); 3.35 ($CH_2CH_2$ backbone); 3.18 (N—$CH_2$); 2.32-2.27 (C(O)—$CH_2$); 0.96 ($CH_3$). Signals for the alkynyl group were present at δ 4.17 ppm ($CH_2$ and CH).

Example 19. Synthesis of Compound 10

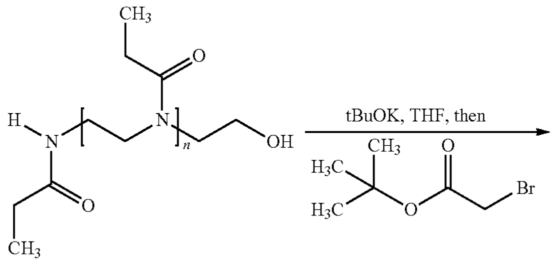

-continued

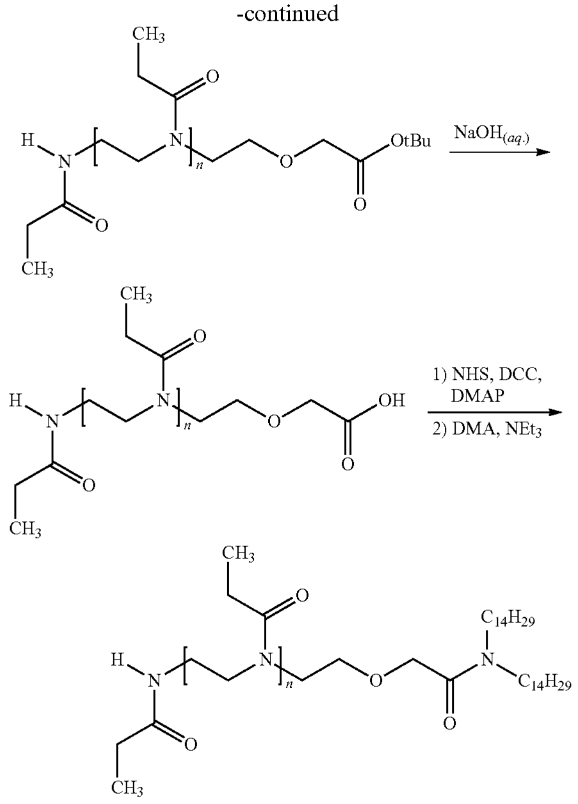

10

Poly(ethyloxazoline) (OH terminated, 0.5 grams, 0.27 mmol, 1.00 equiv) was dissolved in 30 mL THE and transferred to an oven-dried 250 mL round bottomed flask. Potassium tert-butoxide (0.09 g, 0.81 mmoL, 3.00 equiv) was added, and the reaction mixture was allowed to stir for 30 min at room temperature. Following this time period, tert-butyl bromoacetate (0.24 mL, 1.62 mmol, 6.00 equiv) was added, and the reaction mixture was allowed to stir at room temperature for at least 12 hours. Following this time period, the reaction mixture was transferred to a separatory funnel along with brine (50 mL). The mixture was extracted with $CH_2Cl_2$ (2×25 mL), and the combined organics were dried with sodium sulfate and concentrated in vacuo. The resulting solid was dissolved in a 1M aqueous solution of NaOH (20 mL) and stirred for at least 12 hours at room temperature. The solution was then acidified to pH=3, extracted with $CH_2Cl_2$ (2×30 mL), and the combined organics were dried with sodium sulfate and concentrated in vacuo to afford 0.4 grams of the intermediate carboxylic acid, which was used directly without further purification.

A 100 mL round bottomed flask was charged with the carboxylic acid from above (1 g, 0.45 mmol, 1.00 equiv) followed by $CH_2Cl_2$ (30 mL), DMAP (0.01 g), and lastly NHS (0.04 grams, 0.36 mmol, 2.00 equiv). DCC (0.08 g, 036 mmol, 2.00 equiv) was then added, and the reaction mixture was allowed to stir for at least 12 hours at room temperature. The resulting mixture was then filtered and concentrated to afford the intermediate NHS ester, which was used directly without further purification. The NHS ester was then transferred to a 100 mL round bottomed flask, and $CH_2Cl_2$ (30 mL) was added. Dimyristylamine (0.56 grams, 1.36 mmol, 3.00 equiv) was added followed by triethylamine (0.20 mL, 1.36 mmol, 3.00 equiv). The reaction mixture was stirred for at least 12 hours whereupon the mixture was diluted with brine (20 mL) and transferred to a separatory funnel. The mixture was extracted with $CH_2Cl_2$ (2×20 mL), and the combined organics were dried with sodium sulfate and concentrated in vacuo. The product was purified via reverse phase chromatography (C18, acetonitrile:methanol) to afford the 0.27 grams of the title compound.

$^1H$ NMR analysis showed the standard backbone signals for PEOZ (500 MHz, DMSO) δ 4.27-3.93 ($CH_2O$ and O—$CH_2$—N); 3.35 ($CH_2CH_2$ backbone); 2.96 (N—$CH_2$); 2.32-2.27 (C(O)—$CH_2$); 0.96 ($CH_3$). Additional signals were present for the lipid moiety at δ 1.49-1.54 (N—$(CH_2)_2$); 1.27 ($CH_2$); 0.87 ($CH_3$)

Example 20. Synthesis of Compound 11a

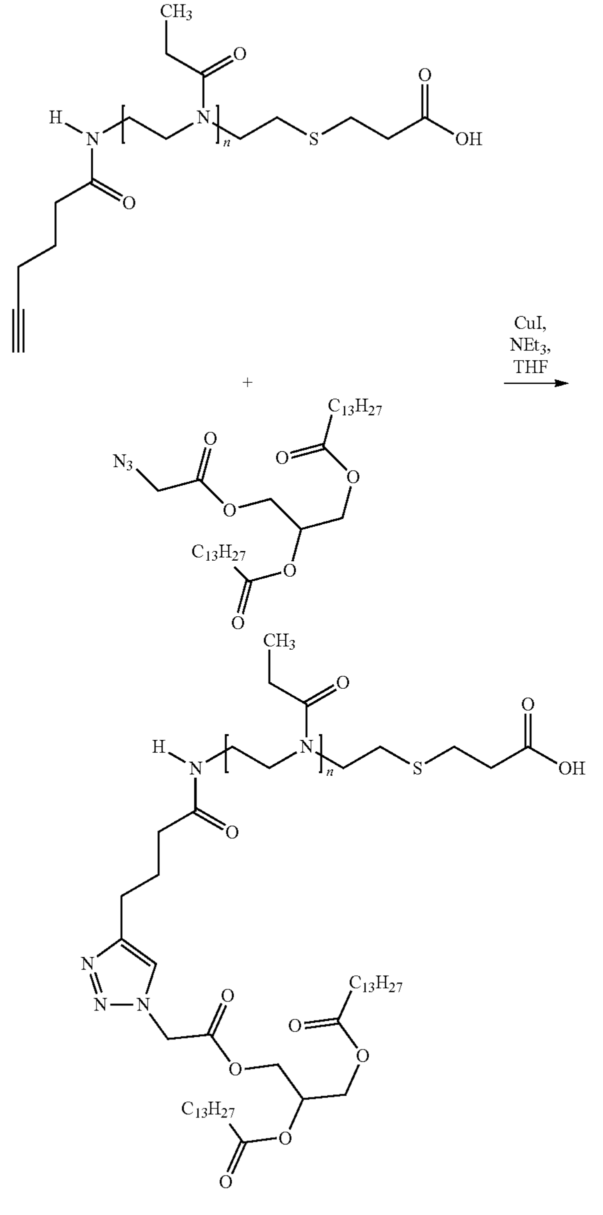

11a

A 100 mL round bottomed flask was charged with the acid described above (0.68 g, 0.31 mmol, 1.00 equiv) followed by the azidoacetate (0.27 g, 0.46 mmol, 1.50 equiv), THF (50 mL), CuI (0.24 g, 1.24 mmol, 4.00 equiv), and lastly triethylamine (0.64 mL, 4.60 mmol, 10.0 equiv). The resulting mixture was heated to 50° C. and stirred overnight. Following this time period, the reaction mixture was cooled to room temperature and quenched via addition of 0.1 M HCl (30 mL) and stirred for 10 minutes. The resulting mixture was passed through a pre-prepared 60 mL Dowex column. The resulting solution was concentrated on a rotary evaporator at 35° C. and subsequently transferred to a separatory funnel. Brine (20 mL) was added, and the mixture was extracted 3 times with 20 mL portions of DCM. The combined organic extracts were dried with sodium sulfate and concentrated in vacuo. The product was purified via reverse phase C18 chromatography using acetonitrile and methanol as the eluents to afford the title compound (0.18 grams).

$^1H$ NMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). Additional signals were present for the lipid derivative moiety at (5.10 (CH); 4.26 ($CH_2$); 4.08 ($CH_2$); 1.49 (C(O)$CH_2$); 1.23 ($CH_2$); 0.84 ($CH_3$). Additional signals were present for the triazole moiety at s 5.34 (triazole CH); 4.35 (ester $CH_2$); 4.11 (HN—$CH_2$).

Example 21. Synthesis of Compound 11b

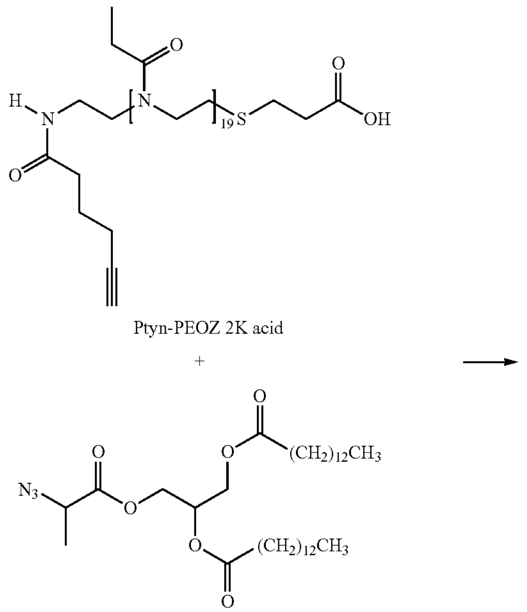

Ptyn-PEOZ 2K acid

+

DMG-(2-azidopropionate)

-continued

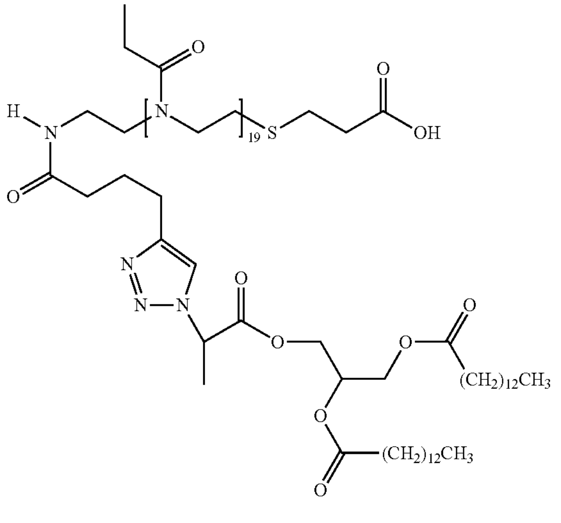

11b

To a solution of Ptyn-PEOZ 2K acid (0.500 g, 0.227 mmol, 1.0 eq, Mn 2199 Da) and DMG-(2-azidopropionate (0.166 g, 0.273 mmol, 1.2 eq) in THE (10 mL) were added CuI (0.0217 g, 0.114 mmol, 0.5 eq) and TEA (0.0634 mL, 0.455 mmol, 2.0 eq). The resulting mixture was stirred for 5 minutes at room temperature and then allowed to stir for 18 hours at 50° C. to give a cloudy yellow solution. After the cooling down to room temperature, the reaction mixture was quenched by adding 0.1N aqueous HCl (6 mL) followed by stirring for 5 minutes. The mixture was passed through the Dowex© M4195 column and then THF was removed from the filtrate using a rotary evaporator. The resulting aqueous solution was stirred with 20 mL of dichloromethane using 0.5 g of NaCl (5 w/v % of water volume). The organic phase was collected, dried over $Na_2SO_4$, filtered, and concentrated. The residue was dissolved in 5 mL of DCM and precipitated by adding into diethyl ether (60 mL), filtered, and dried in vacuo. The resulting pale yellow crystalline was further purified using a Biotage (SNAP ultra C-18 column, MeCN/MeOH) to remove polymer impurities. Fractions 5-21 were collected and concentrated to give the desired product (0.20 g, 31.3% yield with 99.8% purity) as a white crystalline.

The attachment of DMG-(2-azidopropionate) was proved by $^1H$ NMR (Varian, 500 MHz, 10 mg/mL DMSO-d6) spectra that show the DMG protons at 0.84 ppm (t, 6H, J=6.5 Hz, —$(CH_2)_{10}CH_3$), 1.23 ppm (m, 40H, —$(CH_2)_{10}CH_3$), 1.49 ppm (m, 4H, —$CH_2(CH_2)_{10}CH_3$), 1.81 ppm (d, 3H, J=5.0 Hz, triazole-CH($CH_3$)C(═O)O—), 2.28 ppm (m, 4H, —$CH_2CH_2(CH_2)_{10}CH_3$), 3.07 ppm, 4.23 ppm and 4.33 ppm (m, 4H, —$OCH_2CH(O—)CH_2O$—), 5.18 ppm (m, 1H, —$OCH_2CH(O—)CH_2O$—), 5.59 ppm (m, 1H, triazole-CH ($CH_3$)C(═O)O—), and 8.09 ppm (s, 1H, triazole ring, resulted from the 'Click' reaction), besides the usual polymer backbone peaks.

Example 22. Synthesis of Compound 11c

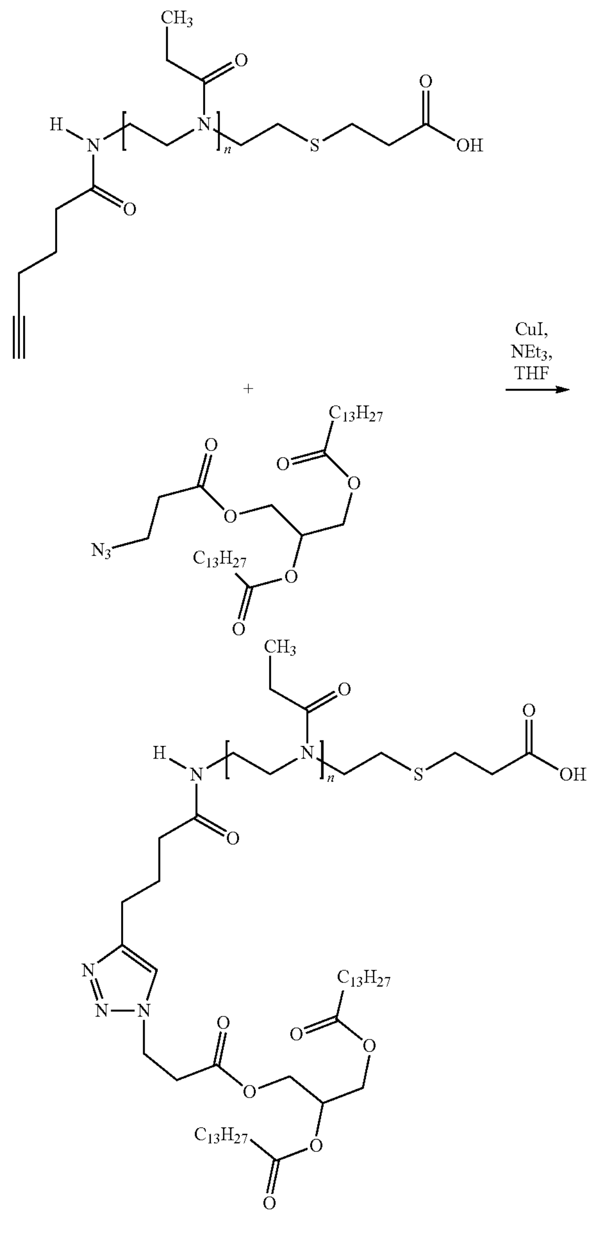

11c

A 100 mL round bottomed flask was charged with the acid described above (1.42 g, 0.65 mmol, 1.00 equiv) followed by the azidopropionate (0.59 g, 0.97 mmol, 1.50 equiv), THE (50 mL), CuI (0.5 g, 2.6 mmol, 4.00 equiv), and lastly triethylamine (0.91 mL, 6.50 mmol, 10.0 equiv). The resulting mixture was heated to 50° C. and stirred overnight. Following this time period, the reaction mixture was cooled to room temperature and quenched via addition of 0.1 M HCl (30 mL) and stirred for 10 minutes. The resulting mixture was passed through a pre-prepared 60 mL Dowex column. The resulting solution was concentrated on a rotary evaporator at 35° C. and subsequently transferred to a separatory funnel. Brine (20 mL) was added, and the mixture was extracted 3 times with 20 mL portions of DCM. The combined organic extracts were dried with sodium sulfate and concentrated in vacuo. The product was purified via reverse phase C18 chromatography using acetonitrile and methanol as the eluents to afford the title compound (0.34 grams).

$^1$H NMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). Additional signals were present for the lipid derivative moiety at δ 5.10 (CH); 4.51 ($CH_2$); 4.26 ($CH_2$); 4.08 ($CH_2$); 1.49 (C(O)$CH_2$); 1.23 ($CH_2$); 0.84 ($CH_3$). Additional signals were present for the triazole moiety at δ 4.35 (ester $CH_2$); 4.11 (HN—$CH_2$).

Example 23. Synthesis of Compound 12a

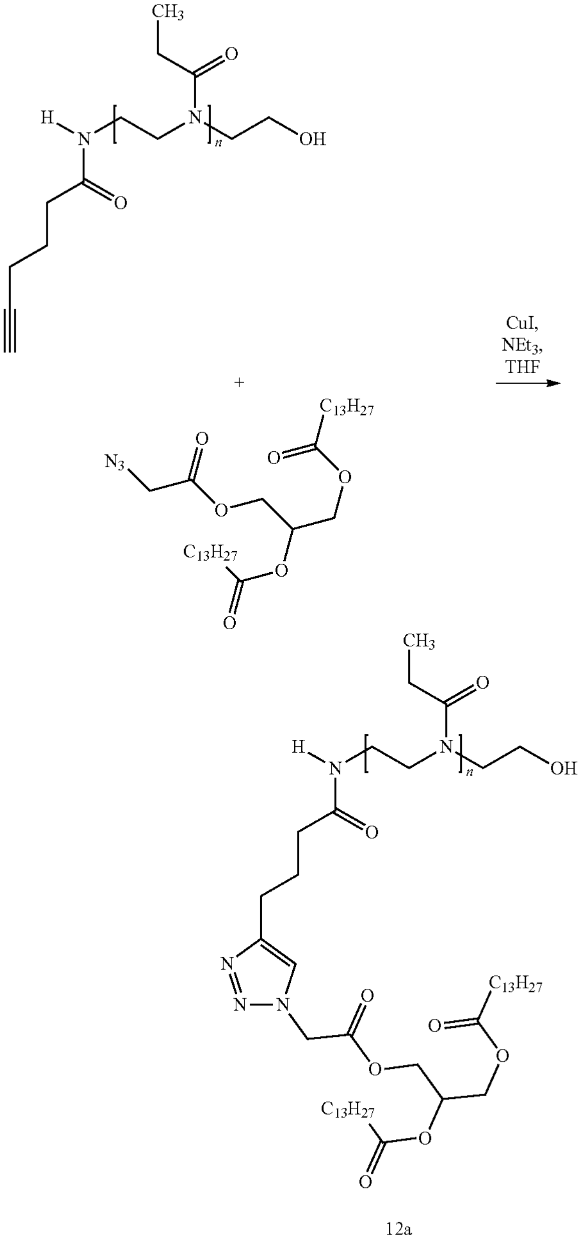

12a

A 100 mL round bottomed flask was charged with the acid described above (0.82 g, 0.37 mmol, 1.00 equiv) followed by the azidoacetate (0.40 g, 0.67 mmol, 1.80 equiv), THE (50 mL), CuI (0.28 g, 1.48 mmol, 4.00 equiv), and lastly triethylamine (0.52 mL, 3.70 mmol, 10.0 equiv). The resulting mixture was heated to 50° C. and stirred overnight. Following this time period, the reaction mixture was cooled to room temperature and quenched via addition of 0.1 M HCl (30 mL) and stirred for 10 minutes. The resulting mixture was passed through a pre-prepared 60 mL Dowex column. The resulting solution was concentrated on a rotary evaporator at 35° C. and subsequently transferred to a separatory funnel. Brine (20 mL) was added, and the mixture was extracted 3 times with 20 mL portions of DCM. The combined organic extracts were dried with sodium sulfate and concentrated in vacuo. The product was purified via reverse phase C18 chromatography using acetonitrile and methanol as the eluents to afford the title compound (0.22 grams).

$^1$H NMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). Additional signals were present for the lipid derivative moiety at δ 5.20 (CH); 4.26 ($CH_2$); 1.49 (C(O)$CH_2$); 1.23 ($CH_2$); 0.84 ($CH_3$). Additional signals were present for the triazole moiety at δ 5.35 (ester $CH_2$); 4.11 (HN—$CH_2$).

Example 24. Synthesis of Compound 19b

A. Synthesis of DMG-(2-azidopropionate)

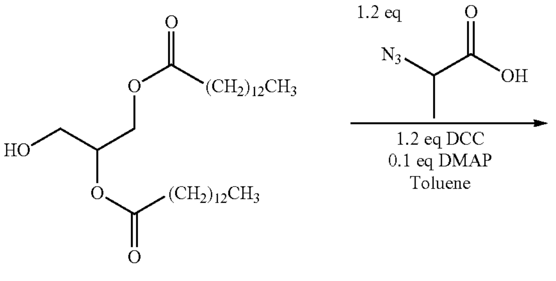

DMG
(1,2-Dimyristoyl-rac-glycerol)

-continued

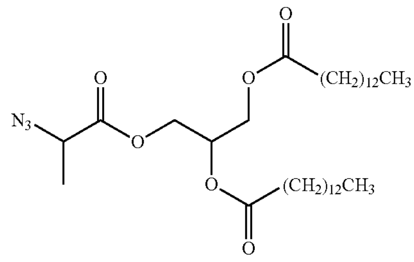

DMG-(2-azidopropionate)

To a solution of DMG (1.02 g, 1.900 mmol, 1.0 eq) in toluene (20 mL) were added 2-azidopropionic acid (0.289 g, 2.280 mmol, 1.2 eq, 90.8 wt %) and DMAP (0.0232 g, 0.019 mmol, 0.1 eq). After the addition of DCC (0.470 g, 2.280 mmol, 1.2 eq), and the resulting mixture was allowed to stir for 2 hours at room temperature. The resulting mixture was filtered using a syringe filter and concentrated down using a rotary evaporator. The residue was purified using a Biotage (SNAP ultra-silica-gel column, EtOAc/Hex) to give the desired product (1.09 g, 93.9% yield, 99.9% purity).

The attachment of 2-azidopropionic acid was proved by $^1$H NMR (Varian, 500 MHz, 10 mg/mL DMSO-d6) spectra that show the protons at 0.85 ppm (t, 6H, J=6.5 Hz, —$(CH_2)_{10}$CH3), 1.23 ppm (m, 40H, —$(CH_2)_{10}CH_3$), 1.32 ppm (m, 3H, $N_3CH(CH_3)C(=O)O$—), 1.50 ppm (m, 4H, —$CH_2(CH_2)_{10}CH_3$), 2.28 ppm (m, 4H, —$CH_2CH_2(CH_2)_{10}CH_3$), 4.15 ppm and 4.35 ppm (m, 4H, —$OCH_2CH(O—)CH_2O$—), 4.29 ppm (m, 1H, $N_3CH(CH_3)C(=O)O$—), and 5.24 ppm (m, 1H, —$OCH_2CH(O—)CH_2O$—).

B. Synthesis of PEOZ 2K DMG-(triazole-2-propionate)

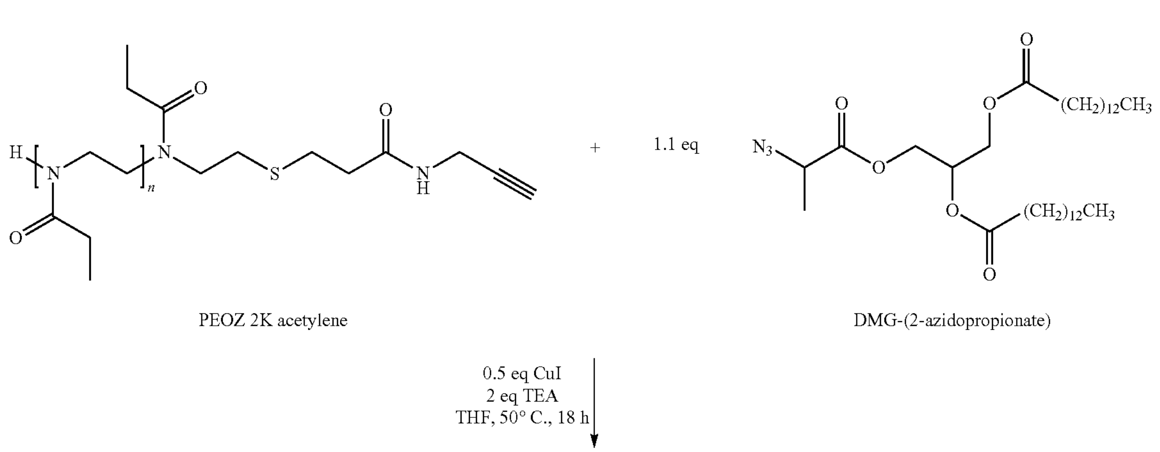

PEOZ 2K acetylene

DMG-(2-azidopropionate)

-continued

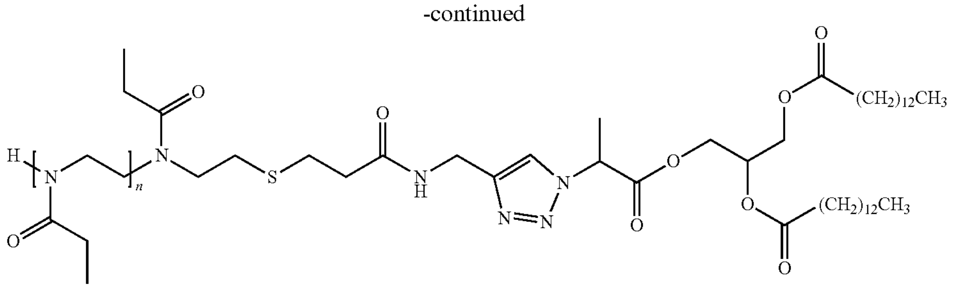

19b

To a solution of PEOZ 2K acetylene (1.01 g, 0.450 mmol, 1.0 eq, Mn 2249 Da) and DMG-(2-azidopropionate (0.302 g, 0.495 mmol, 1.1 eq) in THF (10 mL) were added CuI (0.0429 g, 0.225 mmol, 0.5 eq) and TEA (0.125 mL, 0.900 mmol, 2 eq). The resulting mixture was stirred for 4 minutes at room temperature and then allowed to stir for 18 hours at 50° C. After cooling to room temperature, the reaction mixture was quenched by adding 0.1N aqueous HCl (12 mL) followed by stirring for 5 minutes. The mixture was passed through the Dowex© M4195 column and THF was removed from the filtrate using a rotary evaporator. The resulting aqueous solution was stirred with 30 mL of dichloromethane using 2 g of NaCl (10 w/v % of water volume). The organic phase was collected, dried over $Na_2SO_4$, filtered, and concentrated. The residue was dissolved in 6 mL of DCM and precipitated by adding into diethyl ether (70 mL), filtered, and dried in vacuo. The resulting pale yellow crystalline was further purified using a Biotage (SNAP ultra C-18 column, MeCN/MeOH) to remove polymer impurities followed by lyophilization to give the desired product (0.560 g, 43.8% yield with 99.8% purity) as a white crystalline.

The attachment of DMG-(2-azidopropionate) was proved by $^1H$ NMR (Varian, 500 MHz, 10 mg/mL DMSO-d6) spectra that show the DMG protons at 0.84 ppm (t, 6H, J=6.5 Hz, $-(CH_2)_{10}CH_3$), 1.23 ppm (m, 40H, $-(CH_2)_{10}CH_3$), 1.49 ppm (m, 4H, $-CH_2(CH_2)_{10}CH_3$), 1.71 ppm (d, 3H, J=7.5 Hz, triazole-$CH(CH_3)C(=O)O-$), 2.28 ppm (m, 4H, $-CH_2CH_2(CH_2)_{10}CH_3$), 4.06 ppm and 4.28 ppm (m, 4H, $-OCH_2CH(O-)CH_2O-$), 5.18 ppm (m, 1H, $-OCH_2CH(O-)CH_2O-$), 5.64 ppm (m, 1H, triazole-$CH(CH_3)C(=O)O-$), and 8.00 ppm (s, 1H, triazole ring, resulted by 'Click' reaction), besides the usual polymer backbone peaks.

Example 25. Synthesis of Compound 19c

Step 1—Synthesis of 1,2-Dimyristoyl-3-azidopropionyl-rac-glycerol (DMG-3-azidopropionate)

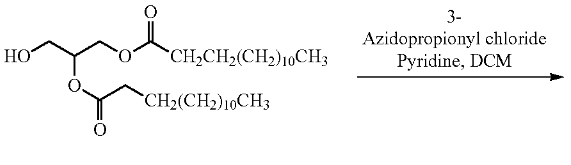

-continued

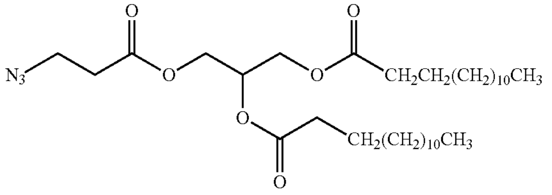

1,2-Dimyristoyl-rac-glycerol (DMG, 1.00 gm, 1.95 mmol, 1.0 eq.) was dissolved in anhydrous DCM (50 mL). Under argon, anhydrous pyridine (632 μL, 7.80 mmol, 4.0 eq.) was added, followed by addition of 3-azidopropionyl chloride (521 mg, 3.90 mmol, 2.0 eq.). The reaction mixture was allowed to stir under argon at room temperature. Following one hour of reaction, the solution was evaporated to dryness. The residual was dissolved in DCM (100 mL), which was washed by 0.05 M HCl (2×40 mL). The DCM phase was dried over anhydrous MgSO4 (4 gm). The mixture was filtered. The clear filtrate was evaporated to dryness, which afforded 1.228 gm of crude product (yellow colored liquid). The crude product was purified by flash chromatography with a Biotage SNAP Ultra 25 g column on a Biotage Isolera System using hexanes and ethyl acetate as mobile phases. Following column purification, mobile phases in the product fraction was evaporated, and the residual was further dried in vacuum overnight, which afforded 0.72 gm of colorless liquid/white wax. TLC (silica gel 60) shows one spot. $^1H$ NMR (Varian, 500 MHZ, 4 mg/mL DMSO-d6, δ, ppm, TMS): 0.85 (t, 2×3H, $-CH_3$), 1.23 (m, ill resolved, 2×20H, $-(CH_2)_{10}-$), 1.50 (m, 2×2H, $-(C=O)CH_2CH_2-$), 2.28 (t, 2×2H, $-(C=O)CH_2-$), 2.61 (t, 2H, $N_3CH_2CH_2-$), 3.54 (t, 2H, $N_3CH_2-$), 4.14, 4.20 (qq, 2H, $-CH_2O(C=O)C_{13}H_{27}$), 4.28 (d, 2H, $-CH_2O(C=O)C_2H_4N_3$), 5.20 (m, 1H, $-(OCH_2)_2CH-O-$).

Step 2—Synthesis of PEOZ-(triazole-3-propionyl-DMG) 2K, 19c, by Click Reaction

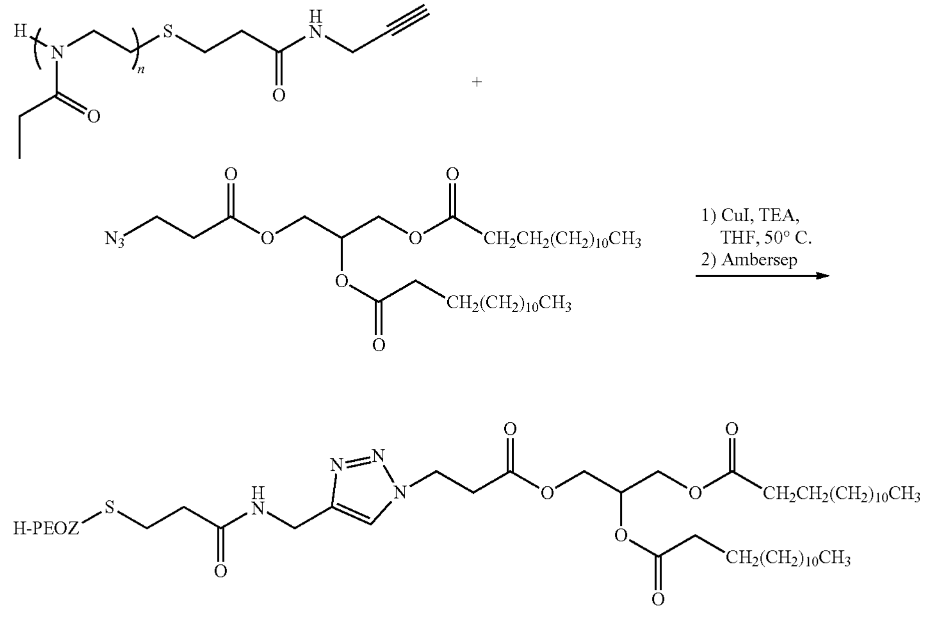

19c

H-PEOZ-propargyl amide 2K (1.0 gm, 0.67 mmol, 1 eq.) was dissolved in 25 mL of THF in a 50 mL round bottom flask with DMG-3-azidopropionate (0.464 gm, 0.76 mmol, 1.1 eq.). The solution was stirred under a slow argon flow. CuI (72.4 mg, 0.38 mmol, 0.5 eq.) was then added to the flask, followed by addition of TEA (185.4 μL, 1.33 mmol, 1.9 eq.). The greenish colored solution was allowed to stir at 50° C. in an oil bath for overnight under argon atmosphere. The reaction went completion as indicated by reversed phase HPLC analysis of the reaction mixture. The solution was mixed with 26.6 mL of 50 mM HCl (1.33 mmole) and THF (25 mL). Copper in the solution was removed by passing the solution through Ambersep M4195 media packed in a glass column. The column was eluted with THF-2 mM HCl (2:1 v/v). The eluent (150 mL) was evaporated until THE was removed. NaCl (5 gm) was added to the remaining white cloudy aqueous solution, which was extracted by DCM (4×50 mL). DCM phase was dried over anhydrous magnesium sulfate (3 gm) and anhydrous sodium sulfate (20 gm). Following filtration to remove magnesium sulfate and sodium sulfate, the filtrate was concentrated to near dryness, and then redissolved in 4 mL of DCM, followed by precipitation in diethylether (160 mL). The precipitate was collected after filtration, and dried in vacuum, which afforded 0.87 gm of amber colored powder (PEOZ-(triazole-3-propionyl-DMG) 2K). Purity by reversed phase HPLC is 99.7%. $^1$H NMR (Varian, 500 MHZ, 10 mg/mL DMSO-d6, δ, ppm, TMS): 0.85 (t, 2×3H, —$C_{13}H_{24}CH_3$), 1.23 (m, ill resolved, 2×20H, —$(CH_2)_{10}$—), 1.49 (m, 2×2H, —(C═O)$CH_2CH_2$—), 2.04 (t, 2×2H, —(C═O)$CH_2$—), 2.97 (t, 2H, -triazole-$CH_2CH_2$—), 4.10, 4.16 (mm, 2H, —$CH_2O$(C═O)$C_{13}H_{27}$), 4.28 (d, 2H, —$CH_2O$(C═O)$C_2H_4$-triazole), 4.54 (t, 2H, -triazole-$CH_2$—), 5.17 (m, 1H, —$(OCH_2)_2CH$—O—), 7.90 (s, 1H, —CH— on triazole ring), 8.51 (t, ill resolved, 1H, —(C═O)NH—$CH_2$-triazole-) PEOZ backbone peaks are at 0.95 (medium) (s, 3nH, $CH_3CH_2$(C═O)NH—), 2.27 (small) (s, 2nH, —$CH_2$(C═O)NH—), and 3.35 (large) (s, 4nH, —$NCH_2CH_2N$—).

Example 26. Synthesis of Compound 20a

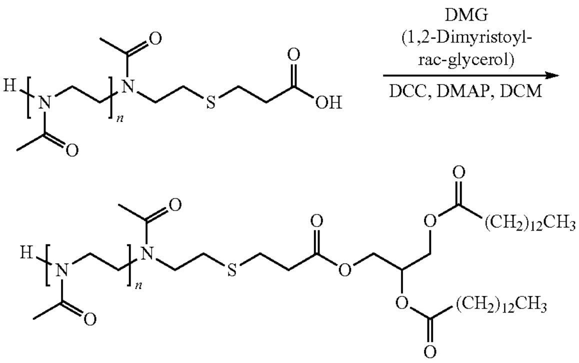

20a

Synthesis of PMOZ 2K DMG ester

To a solution of PMOZ 2K acid (1.08 g, 0.500 mmol, 1.0 eq, Mn 2166 Da) in DCM (12 mL) were added 1,2-Dimyristoyl-rac-glycerol (0.283 g, 0.525 mmol, 1.05 eq, 95%) and DMAP (0.0062 g, 0.050 mmol, 0.1 eq). At 45° C., DCC (0.108 g, 0.525 mmol, 1.05 eq) was added and the resulting mixture was allowed to stir for 1 hour. Additional DMG (0.283 g, 0.525 mmol, 1.05 eq, 95%) and DCC (0.108 g, 0.525 mmol, 1.05 eq) were freshly added into the mixture. After the stirring for 16 hours at 45° C., the reaction mixture was cooled down to room temperature, filtered using a syringe filter, and concentrated down using a rotary evaporator. The residue was purified using a Biotage (SNAP ultra C18 column, MeCN/MeOH) to give the desired product (0.40 g, 30% yield, 99.8% purity)

The attachment of DMG was proved by $^1H$ NMR (Varian, 500 MHz, 10 mg/mL DMSO-d6) spectra that shows the DMG protons at 0.85 ppm (t, 6H, J=6.5 Hz, $—(CH_2)_{10}CH_3$), 1.23 ppm (m, 40H, $—(CH_2)_{10}CH_3$), 1.50 ppm (m, 4H, $—CH_2(CH_2)_{10}CH_3$), 2.72 ppm (t, 4H, J=6.5 Hz, $—CH_2CH_2(CH_2)_{10}CH_3$), 4.15 ppm and 4.27 ppm (m, 2H each, $—OCH_2CH(O—)CH_2O—$), and 5.19 ppm (m, 1H, $—OCH_2CH(O—)CH_2O—$), besides the usual polymer backbone peaks.

Example 27. Synthesis of Compound 20b

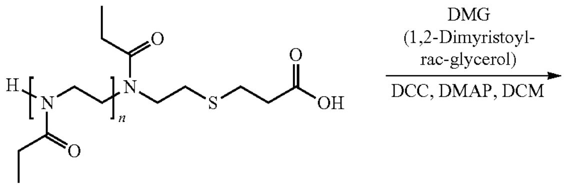

-continued

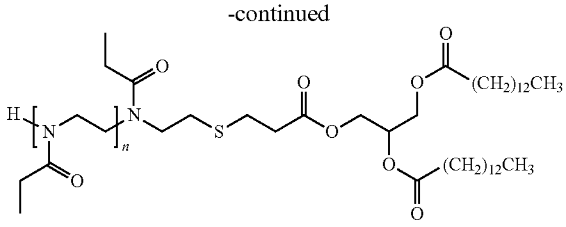

20b

Synthesis of PEOZ 2K DMG Ester

To a solution of PEOZ 2K acid (0.660 g, 0.300 mmol, 1.0 eq, Mn 2200 Da) in DCM (12 mL) were added 1,2-Dimyristoyl-rac-glycerol (0.170 g, 0.315 mmol, 1.05 eq, 95%) and DMAP (0.0037 g, 0.030 mmol, 0.1 eq). After the addition of DCC (0.065 g, 0.315 mmol, 1.05 eq), the resulting mixture was allowed to stir for 18 hours. The mixture was filtered using a syringe filter, and concentrated down using a rotary evaporator. The residue was purified using a Biotage (SNAP ultra C18 column, MeCN/MeOH) to give the desired product (0.624 g, 78% yield, >99.9% purity) The attachment of DMG was proved by $^1H$ NMR (Varian, 500 MHz, 10 mg/mL DMSO-d6) spectra that shows the DMG protons at 0.85 ppm (t, 6H, J=6.5 Hz, $—(CH_2)_{10}CH_3$), 1.23 ppm (m, 40H, $—(CH_2)_{10}CH_3$), 1.50 ppm (m, 4H, $—CH_2(CH_2)_{10}CH_3$), 2.70 ppm (t, 4H, J=6.5 Hz, $—CH_2CH_2(CH_2)_{10}CH_3$), 4.15 ppm and 4.26 ppm (m, 2H each, $—OCH_2CH(O—)CH_2O—$), and 5.19 ppm (m, 1H, $—OCH_2CH(O—)CH_2O—$), besides the usual polymer backbone peaks.

Example 28. Synthesis of Compound 21

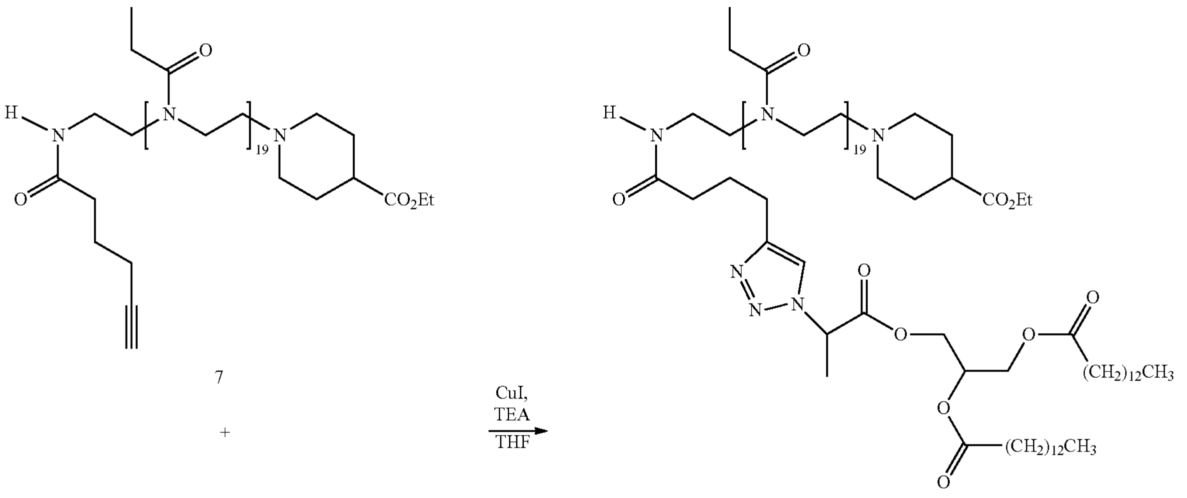

7

+

21

-continued

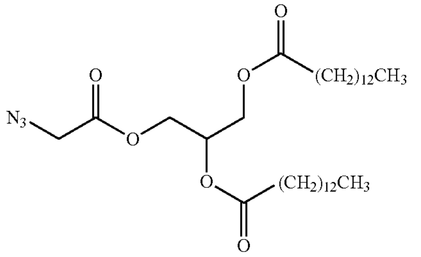

To a solution of Ptyn-PEOZ 2K isonipecotate (Compound 7, 0.500 g, 0.274 mmol, 1.0 eq, Mn 1823 Da) and DMG-(2-azidopropionate (0.277 g, 0.455 mmol, 1.6 eq) in THE (15 mL) were added CuI (0.0433 g, 0.227 mmol, 0.83 eq) and TEA (0.095 mL, 0.682 mmol, 2.5 eq). The resulting mixture was stirred for 5 minutes at room temperature and then allowed to stir for 18 hours at 50° C. to give a cloudy yellow solution. After the cooling down to room temperature, the reaction mixture was quenched by adding 0.1N aqueous HCl (8 mL) followed by stirring for 5 minutes. The mixture was passed through the Dowex© M4195 column and then THE was removed from the filtrate using a rotary evaporator. The resulting aqueous solution was stirred with 20 mL of dichloromethane using 0.5 g of NaCl (5 w/v % of water volume). The organic phase was collected, dried over $Na_2SO_4$, filtered, and concentrated. The residue was dissolved in 5 mL of DCM and precipitated by adding into diethyl ether (60 mL), filtered, and dried in vacuo. The resulting pale yellow crystalline was further purified using a Biotage (SNAP ultra C-18 column, acetonitrile/methanol) to remove polymer impurities. Fractions 5-21 were collected and concentrated to give the desired product (0.140 g, 21% yield with 99.8% purity) as a yellow crystalline solid.

The attachment of DMG-(2-azidopropionate) was proved by $^1H$ NMR (Varian, 500 MHz, 10 mg/mL DMSO-d6) that showed the DMG protons at 0.84 ppm (t, 6H, J=6.5 Hz, $—(CH_2)_{10}CH_3$), 1.23 ppm (m, 40H, $—(CH_2)_{10}CH_3$), 1.49 ppm (m, 4H, $—CH_2(CH_2)_{10}CH_3$), 1.72 ppm (d, 3H, J=7.0 Hz, triazole-$CH(CH_3)C(═O)O—$), 2.28 ppm (m, 4H, $—CH_2CH_2(CH_2)_{10}CH_3$), 4.08 ppm, 4.23 ppm and 4.33 ppm (m, 4H, $—OCH_2CH(O—)CH_2O—$), 5.18 ppm (m, 1H, $—OCH_2CH(O—)CH_2O—$), 5.59 ppm (m, 1H, triazole-CH $(CH_3)C(═O)O—$), and 8.00 ppm (s, 1H, triazole ring, resulted by 'click' reaction), besides the usual polymer backbone peaks.

Example 29. Synthesis of Compound 22

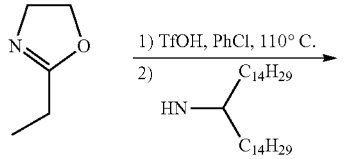

-continued

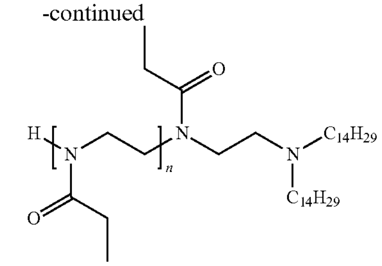

22

An oven-dried 500 mL round bottomed flask was charged with 2-ethyl-2-oxazoline (30 g, 302.63 mmol, 19.00 equiv) followed by PhCl (150 mL) and a stir bar under an atmosphere of Argon. TfOH (1.41 mL, 15.93 mmol, 1.00 equiv) was added dropwise, and the mixture was allowed to stir at room temperature for 5 minutes. The reaction was then warmed to 110° C. and stirred for 35 minutes. The polymerization mixture was then cooled to room temperature and dimyristylamine (13.00 grams, 31.86 mmol, 2.00 equiv) was added. The reaction mixture was allowed to stir for at least 12 hours at room temperature. When this time period was completed, the reaction mixture was diluted with brine (300 mL) and transferred to a separatory funnel. The mixture was extracted with $CH_2Cl_2$ (2×150 mL), dried with sodium sulfate, and concentrated in vacuo to afford 25.6 grams of crude material. A 2 gram sample of crude material was purified via reverse phase C18 chromatography using acetonitrile and methanol as the eluents to afford the title compound (0.55 grams).

$^1H$ NMR. $^1H$ NMR analysis showed the standard backbone signals for PEOZ (500 MHz, $CDCl_3$) δ 3.42 ($CH_2CH_2$ backbone); 3.27 ($N—CH_2$); 2.37-2.25 ($C(O)—CH_2$); 1.11 ($CH_3$). Additional signals were present for the lipid moiety at δ 2.74 ($N—(CH_2)_2$); 2.50 ($N—CH_2$); 1.66 ($CH_2$); 1.35 ($CH_2$); 1.22 (lipid alkyl chain); 0.85 ($CH_3$).

Example 30. Synthesis of Compound 13

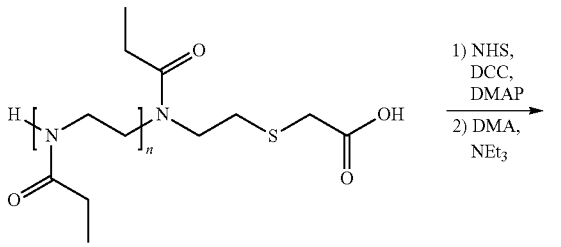

-continued

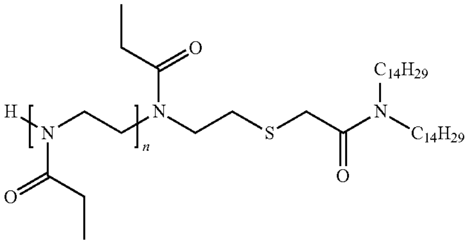

13

-continued

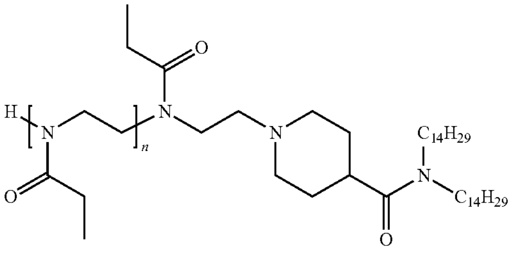

14

Compound 13 was prepared in an analogous fashion to compound 15B. 1.4 grams were isolated.

$^1$H NMR. $^1$H NMR analysis showed the standard backbone signals for PEOZ (500 MHz, $CDCl_3$) δ 3.43 ($CH_2CH_2$ backbone); 3.24 (N—$CH_2$); 2.8 (S—$CH_2$); 2.32-2.19 (C(O)—$CH_2$); 1.12 ($CH_3$). Additional signals were present for the lipid moiety at δ 1.49-1.65 (N—$(CH_2)_2$); 1.27 ($CH_2$); 0.87 ($CH_3$).

Example 31. Synthesis of Compound 14

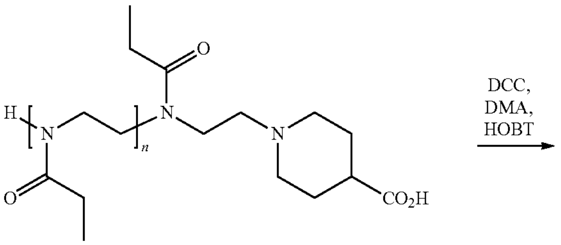

The carboxylic acid (2.00 grams, 0.91 mmol, 1.00 equiv) was transferred to a 250 mL round bottomed flask and azeotroped with acetonitrile. This process was repeated, and the residue was dried under vacuum for 1 hour. The residue was dissolved in $CH_2Cl_2$ (30 mL), and HOBT (0.05 g, 0.36 mmol, 0.4 equiv) was added followed by dimyristylamine (1.12 grams, 2.73 mmol, 3.00 equiv) and lastly DCC (0.6 grams, 2.73 mmol, 3.00 equiv). The reaction mixture was allowed to stir for at least 12 hours whereupon the mixture was filtered and precipitated into a beaker containing 1600 mL hexanes. The solids were collected by vacuum filtration and dried under vacuum. The product was purified via reverse phase C18 chromatography using acetonitrile and methanol as the eluents to afford the title compound (0.47 grams).

$^1$H NMR. $^1$H NMR analysis showed the standard backbone signals for PEOZ (500 MHz, $CDCl_3$) δ 3.42 ($CH_2CH_2$ backbone); 2.93 (N—$CH_2$); 2.39-2.27 (C(O)—$CH_2$); 1.11 ($CH_3$). Additional signals were present for the piperidine moiety at δ 2.92 (N—CH); 1.83 ($CH_2$); 1.76 ($CH_2$); 1.74 ($CH_2$); 1.63 ($CH_2$). Additional signals were present for the lipid moiety at δ 3.25 (N—$CH_2$); 3.19 (N—$CH_2$); 2.05 ($CH_2$); 1.52-1.46 ($CH_2$); 1.25 (lipid alkyl chain); 0.86 ($CH_3$).

Example 32. Synthesis of Compound 23

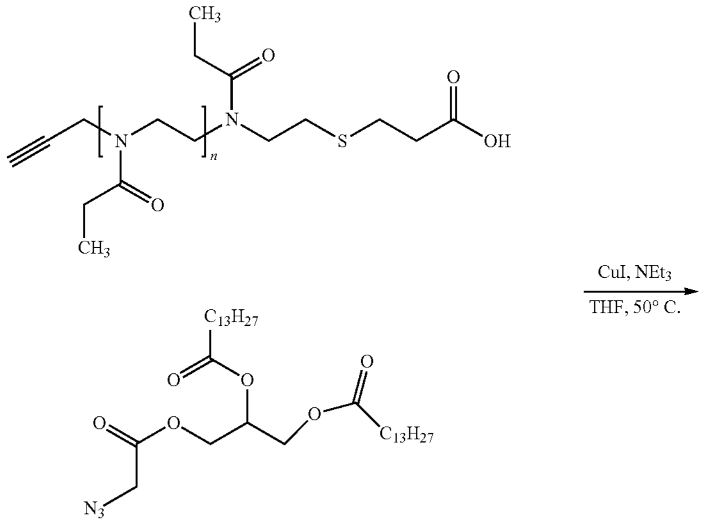

-continued

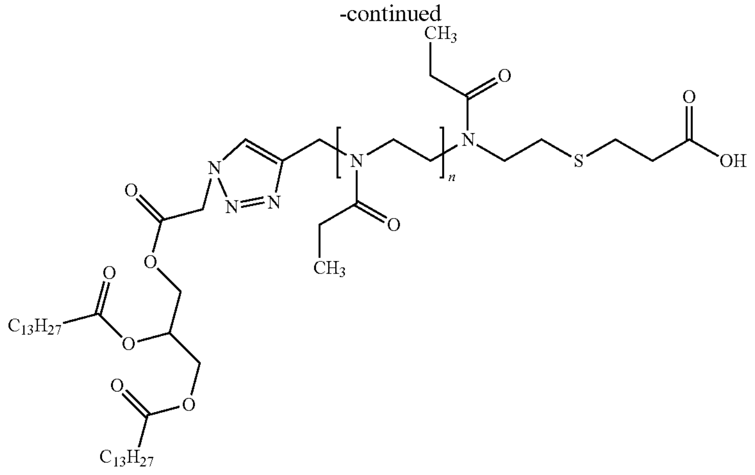

23

Compound 23 was prepared in an analogous fashion to compound 12A. In this instance, 0.19 g was isolated. An analytical purity of 93% was determined via HPLC analysis.

$^1$HNMR analysis showed the standard backbone signals for PEOZ (500 MHz, DMSO) δ 3.35 ($CH_2CH_2$ backbone); 2.71 (S—$CH_2$); 2.32-2.27 (C(O)—$CH_2$); 0.96 ($CH_3$). Additional signals were present for the lipid derivative moiety at δ 5.19 (CH); 4.26 ($CH_2$); 1.49 (C(O)$CH_2$); 1.23 ($CH_2$); 0.84 ($CH_3$). Additional signals were present for the triazole moiety at δ 5.46 (ester $CH_2$); 4.07 (HN—$CH_2$).

Example 33—Preparation of Lipid Nanoparticles Containing N,N-Dimethyltetradecylamine (DMA)

Fresh lipid stock solutions of 1,2-Dioleoyloxy-3-(trimethylammonium)propane [DOTAP](Sigma D6182), 1,2-distearoyl-snglycero-3-phosphocholine [DSPC] (Bachem 4005619), Cholesterol ultrapure (VWR 0433) and 2K polymer (PEG, PMOZ or PEOZ) conjugated DMA (as described in examples above) were prepared in ethanol as stock solutions. The stock solutions were mixed so that the final lipid mixture stock contained 1.30 mg/mL of DOTAP, 0.28 mg/mL of DSPC, 0.59 mg/mL of cholesterol and 0.19 mg/mL of polymer DMA. The solution contained 2.38 mg/mL of total lipid. Then 70 μL of the stock solution was pipetted into 1.5 mL LoBind centrifuge tubes (Eppendorf 022431081) and the ethanol solution was evaporated using a speed vacuum system (GeneVac EZ-2). The dried samples were allowed to dry for an additional 10 minutes under a vent snorkel. The dried lipid mix was hydrated with 250 μL citrate buffer (pH 4.0) and mixed and sonicated for about 10 minutes to prepare lipid nanoparticles (LNPs).

The plasmid DNA (phMGFP, Promega E6421) stock solution was mixed with citrate buffer (pH 4.0) in a ratio of 100 μL of a 0.34 μg/μL concentration with 66.7 μL of citrate buffer so that the total volume was 166.7 μL. An aliquot of 50 μL of plasmid solution containing 10 μg DNA was added to the 250 μL of lipid nanoparticle mixture and pipette mixed and sonicated for less than 1 minute to give a translucent like suspension. The tubes were centrifuged at 14,000 rpm for 30 minutes (Eppendorf microcentrifuge). The supernatant ~300 μL was separated from the LNP pellet and assayed for any residual DNA using a 1.2% agarose gel and Qubit quantification. Results showed the absence of DNA in the supernatant, suggesting complete encapsulation.

The pellets were resuspended in 300 μL of 5 mM HEPES buffer (pH 7.40) and mixed well with the pipette tip for 2 minutes. In order to verify DNA encapsulation of each polymer DMA formulation, an aliquot of the LNP suspension was lysed with Triton X-100. First a 10% Triton stock solution was made in in HEPES buffer. Added 3 μL of this solution to 27 μL if LNP suspension so that final volume was 30 μL and the concentration of triton X-100 surfactant was 1%. The suspension was vortex mixed for 2 minutes and left to stand overnight at 4° C. The mixture was assayed for any residual DNA using a 1.2% agarose gel and Qubit quantification. Results showed a high concentration of DNA in the mixture, suggesting a >90% encapsulation efficiency of each LNP formulation. The suspension easily filters through a 0.22 and 0.1 m PVDF low protein binding 33-mm syringe filters (Millex-W and Millex-GV, Millipore).

Example 34—Preparation of Lipid Nanoparticles containing 1,2-Dimyristoyl-sn-glycerol (DMG)

Fresh lipid stock solutions of 1,2-Dioleoyloxy-3-(trimethyilarnmonium)propane [DOTAP](Sigma D6182), 1,2-distearoyl-snglycero-3-phosphocholine [DSPC] (Bachem 4005619), Cholesterol ultrapure (VWR 0433) and 2K and 5K polymer (PEG, PMOZ or PEOZ) conjugated DMG (as described in examples above) were prepared in ethanol as stock solutions. The stock solutions were mixed so that the final lipid mixture stock contained 1.48 mg/mL of DOTAP, 0.28 mg/mL of DSPC, 0.57 mg/mL of cholesterol and 0.15 mg/mL of 2K polymer DMG. The solution contained 2.49 mg/mL of total lipid. When the 5K polymer DMG conjugates were selected the concentration was 0.32 mg/mL and the solution contained 2.67 mg/mL of total lipid. Then 62 μL of the stock solution was pipetted into 1.5 mL LoBind centrifuge tubes (Eppendorf 022431081) and the ethanol solution was evaporated using a speed vacuum system (GeneVac EZ-2). The dried samples were allowed to dry for an additional 10 minutes under a vent snorkel. The dried lipid mix was hydrated with 275 μL citrate buffer (pH 4.0) and mixed and sonicated for about 10 minutes to prepare lipid nanoparticles (LNPs).

The plasmid DNA (phMGFP, Promega E6421) stock solution was mixed with citrate buffer (pH 4.0) in a ratio of 80 μL of a 2.7 μg/μL concentration with 190 μL of citrate buffer so that the total volume was 270 μL. An aliquot of 25 μL of plasmid solution containing 20 μg DNA was added to the 275 μL of lipid nanoparticle mixture and pipette mixed and sonicated for less than 1 minute to give a translucent like suspension. The tubes were centrifuged at 14,000 rpm for 30 minutes (Eppendorf microcentrifuge). The supernatant ~300 μL was separated from the LNP pellet and assayed for any residual DNA using a 1.2% agarose gel and Qubit quantification. Results showed the absence of DNA in the supernatant, suggesting complete encapsulation.

The pellets were resuspended in 300 μL of 5 mM HEPES buffer (pH 7.40) and mixed well with the pipette tip for 2 minutes. In order to verify DNA encapsulation of each polymer DMA formulation, an aliquot of the LNP suspension was lysed with Triton X-100. First a 10% Triton stock solution was made in in HEPES buffer. Added 3 μL of this solution to 27 μL if LNP suspension so that final volume was 30 μL and the concentration of triton X-100 surfactant was 1%. The suspension was vortex mixed for 2 minutes and left to stand overnight at 4° C. The mixture was assayed for any residual DNA using a 1.2% agarose gel and Qubit quantification. Results showed a high concentration of DNA in the mixture, suggesting a >90% encapsulation efficiency of each LNP formulation. The suspension easily filters through a 0.22 and 0.1 m PVDF low protein binding 33-mm syringe filters (Millex-W and Millex-GV, Millipore) In another experiment, the centrifuged pellets were resuspended in a buffer solution (pH 7.4) containing sodium phosphate monobasic, sodium phosphate dibasic and sucrose. The suspension was lyophilized to give a uniform and stable dry cake that was easily reconstituted in water for injection.

Example 35. Transfection of DNA from LNPs and with HEK-293 Cells

HEK-293 is a human embryonic kidney cell line commonly used in cell biology for transfection studies. The cells are sourced from ATCC (CRL-1573) and have been demonstrated to have transfection efficiency of >85%. In the study protocol, low passage (<5) cells are seeded on assay plates at a density of 20,000 cells in 100 μL antibiotic-free media (EMEM+10% FBS) per well, 24 hours prior to transfection. Immediately prior to transfection, complete media swap is performed and fresh 100 μL of antibiotic-free media (EMEM+10% FBS) is added to each well.

The prepared LNP containing polymer DMA lipids and encapsulated plasmid DNA were added to each well in volumes of 2.6 to 20.8 μL to deliver between 50 to 450 ng of DNA phMGFP per well.

The positive control is FuGENE-HD (Promega E3211) and DNA in a ratio of 3:1. The DNA solution is diluted in serum free medium (Opti-MEM). Both solutions are mixed in a 96-well PCR plate in triplicates in a ratio of 3:1 (0.3 μL reagent to 100 ng plasmid DNA per well) and Opti-MEM is added to 7.33 μL volume. The plates are incubated at room temperature for 25 minutes. The 7.33 μL DNA/transfection mixture is added to the cells in each well.

The plates are covered with supplied lids and placed in the 37° C., 5% $CO_2$, 95% RH incubator. They are incubated for 24-48 hours. At each of the time points, the plates are read on the Evos microscope. All GFP filter photos are read at 4× and all transmitted light photos are read at 10×. The number of GFP fluoresced cells are shown in Table 1 below. Transmitted light photographs showed some unhealthy cells at the highest concentration tested for all polymer DMA lipid formulations particularly that for the PEG DMA lipid which had the highest number of GFP fluoresced cells.

TABLE 1

| Sample | Amount Transfected | Number of Fluoresced Cells T = 24 h |
|---|---|---|
| PEOZ 2K | 58 ng | 1 |
| | 116 ng | 3 |
| | 233 ng | 18 |
| | 466 ng | 50 |
| PMOZ 2K | 44 ng | 1 |
| | 88 ng | 3 |
| | 175 ng | 14 |
| | 350 ng | 25 |
| PEG 2K | 56 ng | 20 |
| | 112 ng | 40 |
| | 225 ng | 80 |
| | 450 ng | 100 |
| Positive Control | 100 ng | 200 |

At the 48 h time point, the fluorescence was high and the observations were 30-35% of cells fluoresced (positive control); 10% (466 ng DNA with PMOZ DMA lipid); 10% (350 ng DNA with PEOZ DMA lipid); and 5% (450 ng DNA with PEG DMA lipid) with highest number of cell deaths.

Example 36. Transfection of DNA from LNPs and with HepG2 Cells

HepG2 is a human hepatocellular carcinoma cell line commonly used in transfection studies. The cells are sourced from ATCC (HB-8065) and have been demonstrated to have transfection efficiencies as high as 95%. In the study protocol, low passage (<5) cells are seeded on assay plates at a density of 40,000 cells in 100 μL antibiotic-free media (DMEM+10% FBS) per well, 24 hours prior to transfection. Immediately prior to transfection, complete media swap is performed and fresh 100 μL of antibiotic-free media (DMEM+10% FBS) is added to each well.

The prepared LNP containing polymer DMG lipids and encapsulated plasmid DNA were added to each well in volumes of 1.9 to 11.7 μL to deliver between 100 to 1000 ng of DNA phMGFP per well.

The positive control is FuGENE-HID (Promega E3211) and DNA in a ratio of 3:1. The DNA solution is diluted in serum free medium (Opti-MVEM). Both solutions are mixed in a 96-well PCR plate in triplicates in a ratio of 3:1 (0.3 μL reagent to 100 ng plasmid DNA per well) and Opti-MEM is added to 7.33 μL volume. The plates are incubated at room temperature for 25 minutes. The 7.33 μL DNA/transfection mixture is added to the cells in each well.

The plates are covered with supplied lids and placed in the 37° C., 500 $CO_2$, 950% RH incubator. They are incubated for 48-72 hours. At each of the time points, the plates are read on the Evos microscope. All GFP filter photos are read at 4× and all transmitted light photos are read at 10×. The number of GFP fluoresced cells are shown in Table 2 below. Transmitted light photographs showed no signs of cellular toxicity.

TABLE 2

| Sample | Amount Transfected | T = 48 h | T = 72 h |
|---|---|---|---|
| PEOZ 5K | 100 ng | 5 | 7 |
| | 200 ng | 7 | 17 |
| | 500 ng | 20 | 100 |
| | 1000 ng | 100 | 400 |
| PMOZ 5K | 100 ng | 3 | 4 |
| | 200 ng | 10 | 23 |
| | 500 ng | 10 | 40 |
| | 1000 ng | 40 | 100 |
| PEOZ 2K | 100 ng | 3 | 5 |
| | 200 ng | 7 | 25 |
| | 500 ng | 40 | 200 |
| | 1000 ng | 100 | 400 |
| PMOZ 2K | 100 ng | 3 | 4 |
| | 200 ng | 4 | 14 |
| | 500 ng | 20 | 40 |
| | 1000 ng | 40 | 80 |
| PEG 2K | 100 ng | 3 | 9 |
| | 200 ng | 20 | 45 |
| | 500 ng | 15 | 45 |
| | 1000 ng | 100 | 300 |
| Positive Control | 100 ng | 200 | 400 |

Example 37. Hydrolysis Kinetics of POZ-Lipid Conjugates

The hydrolysis rates of several POZ-lipid conjugates of the present disclosure were determined in phosphate saline buffer, pH 7.4 (PBS) and biological media containing either 100% or 50% rat and human plasma diluted in PBS. POZ-lipid samples were accurately weighed and dissolved in PBS to prepare stock solutions. These solutions were spiked into the PBS or rat or human plasma media and allowed to incubate at 37° C. Samples were removed from hydrolysis media at different time intervals and quenched by addition of chilled 0.2% formic acid in methanol. Samples were centrifuged, the supernatant transferred into 0.1% formic acid in water, and the samples were then analyzed by high performance liquid chromatography (HPLC) using a reverse phase column (300SB C3) and a gradient flow of 0.1% ammonium formate in water and 0.1% ammonium formate in methanol as the mobile phases. The POZ-lipid conjugates were detected by UV absorption at 210 nm, and its breakdown and degradation metabolites were detected followed by mass spectrometry. The time for 50% of the POZ-lipid to degrade was extrapolated from the concentration-time curves and are reported in Table 3 below.

TABLE 3

| Sample | Half-Life, hour# 1X PBS | 50% Rat Plasma | 50% Human Plasma |
|---|---|---|---|
| PMOZ2kDMA 15a | NRx | NRx* | NRx* |
| PEOZ2kDMA 15b | NRx | NRx* | NRx* |
| PEOZ2kDMG-triazole-acetate 19a | 106 | 1 | 3 |
| PEOZ2kDMG-2'-propionate 19b | 168** | 1 | 5 |
| PEOZ2kDMG-3'-propionate 19c | NRx | <1 | 7 |

TABLE 3-continued

| Sample | Half-Life, hour# 1X PBS | 50% Rat Plasma | 50% Human Plasma |
|---|---|---|---|
| PMOZ2k DMG Ester 20a | NRx | 1 | 7 |
| PEOZ2k DMG Ester 20b | NRx | <1 | 10 |
| PEOZ2k DMG Ether 17c | NRx | 1 | 180** |
| PMOZ5k DMG Ether 17a | NRx | <1 | 258** |
| PEOZ5k DMG Ether 17b | NRx | <1 | 166** |

NRx = No apparent reaction (hydrolysis) after 120 h
*Experiment conducted with 100% Plasma
**Extrapolated from a plot using Microsoft Excel™ software The results show that compounds with the ester linkages (Compounds 19a, 19b, 19c, 20a and 20b) hydrolyzed in plasma at a faster rate than the ones with ether linkages (Compounds 17a, 17b and 17c).

Example 38. Amidase Hydrolysis of Polymer Lipid Conjugates

The purpose of this experiment was to determine whether various polymer lipid conjugates which showed no apparent reaction (hydrolysis) in PBS, rat plasma, or human plasma (above example) would react in presence of a lipo-amidase enzyme. Compounds 13, 15a, and 15b have amide linkages between POZ and lipid. Compound 22 has an amine linkage. POZ-lipid samples were accurately weighed and dissolved in PBS to prepare stock solutions. The amidase chosen was "fatty acid amide hydrolase 1, active human recombinant (FAAH1)" sourced from Bio-Vision with specific activity of ≥9 mU/mg. The amidase was activated by adding PBS pH 8.0 to each vial of amidase, gently mixing and placing in a water bath at 37° C. for two hours. The concentration of the amidase solution was ~2 μg/μL. An aliquot of the POZ-lipid stock solution was added to the activated lipo-amidase solution, gently mixed and allowed to incubate overnight at 37° C. After overnight hydrolysis, methanol was added, the samples were centrifuged, and the supernatants were transferred to HPLC vials. The samples were analyzed by high performance liquid chromatography (HPLC) using a reverse phase column (300SB C3) and a gradient flow of 0.1% ammonium formate in water and 0.1% ammonium formate in methanol as the mobile phases. The peak area of the polymer lipid conjugates was measured by UV absorption at 210 nm. The peak areas at initial and overnight amidase incubation were compared and the results shown in Table 4 below.

TABLE 4

Overnight Hydrolysis of POZ-lipids in Presence of Lipo-amidase Enzyme.

| Compound # | Peak Area of POZ-DMA Analyte |
|---|---|
| 15a time zero | 1139 |
| 15a With Amidase | 771 |
| 15b time zero | 1329 |
| 15b With Amidase | 808 |
| 13 time zero | 1720 |
| 13 With Amidase | 820 |
| 22 time zero | 1015 |
| 22 With Amidase | 894 |

The results show that compounds with amide linkages (Compounds 15a, 15b, and 13) were affected by the lipo-amidase enzyme, as observed with the drop in POZ-DMA peak area after overnight hydrolysis, i.e., 30-50% change. In contrast, Compound 22, with an amine linkage, showed a small decrease in peak area which was not significant and within the error of the experimental conditions, i.e., ±10%.

Example 39. Synthesis of Compound 24

Step 1.

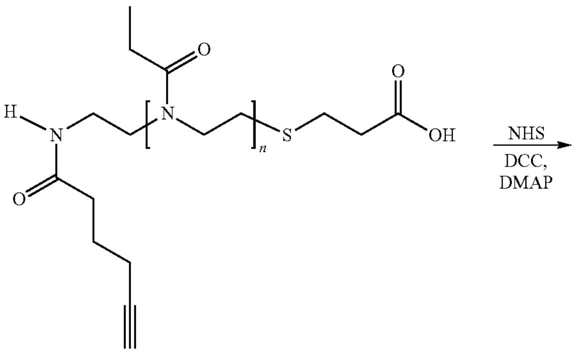

-continued

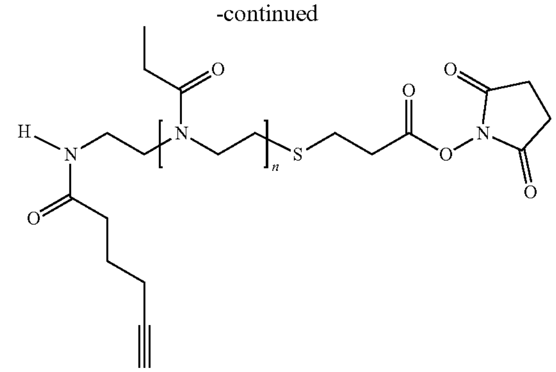

PEOZ 2K (1.21p) NHS ester was prepared in an analogous fashion to that previously described.

$^1$H NMR. HNMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). Additional signals were present for the NHS moiety at δ 2.81 ($(CH_2)_2$). The $CH_2$ signal for the alkyne moiety was detected at δ 1.63 ppm.

Step 2.

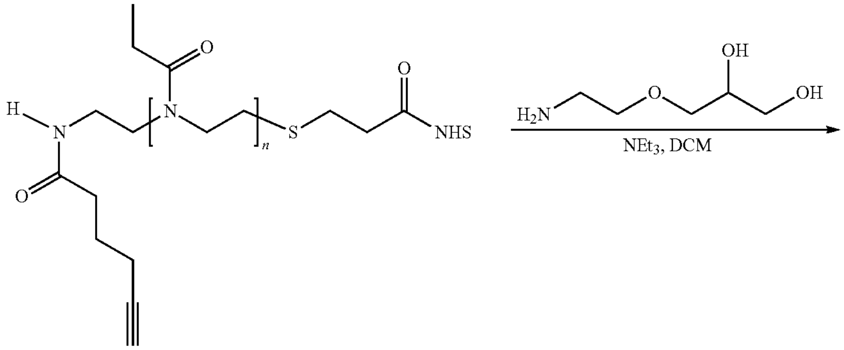

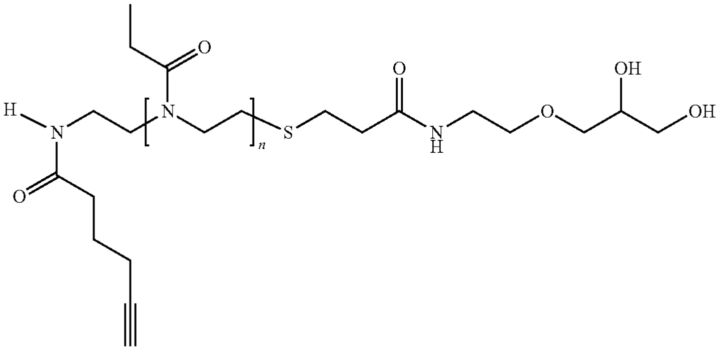

PEOZ 2K (1.21p) ethanolamine glycerol amide was prepared in an analogous fashion to that previously described.

$^1$H NMR. HNMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). The $CH_2$ signal for the alkyne moiety was detected at δ 1.63 ppm. Additional signals for the diol moiety were present at δ 4.56 ($CH_2$); 4.53 (CH).

Step 3.

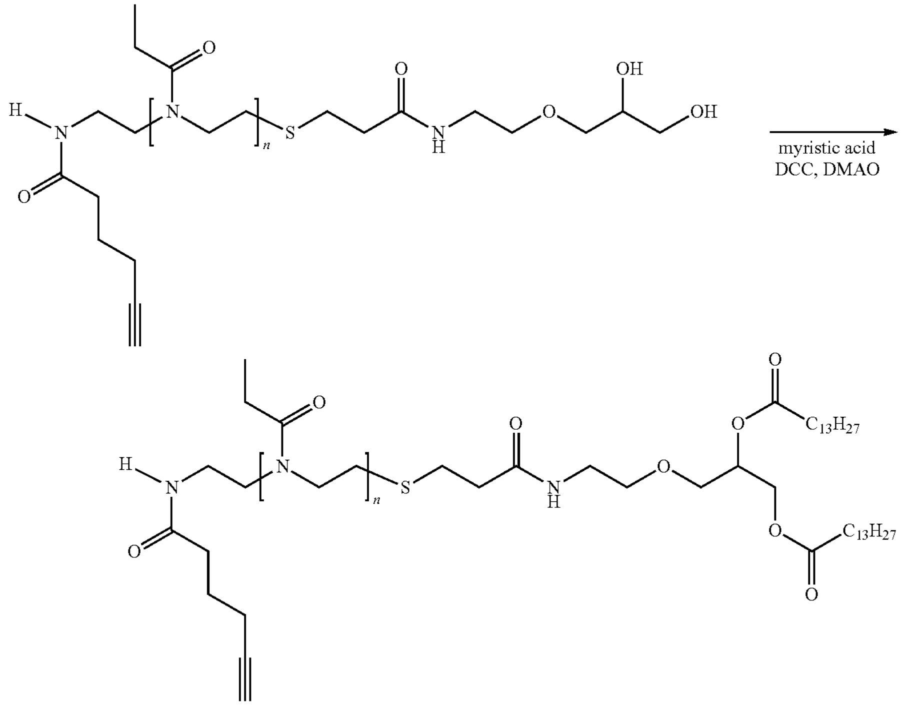

PEOZ 2K (1.21p) DMG was prepared in an analogous fashion to that previously described.

$^1$H NMR. HNMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). Additional signals were present for the lipid derivative moiety at δ 5.20 (CH); 4.26 ($CH_2$); 1.49 (C(O)$CH_2$); 1.23 ($CH_2$); 0.84 ($CH_3$). The $CH_2$ signal for the alkyne moiety was detected at δ 1.63 ppm.

Step 4.

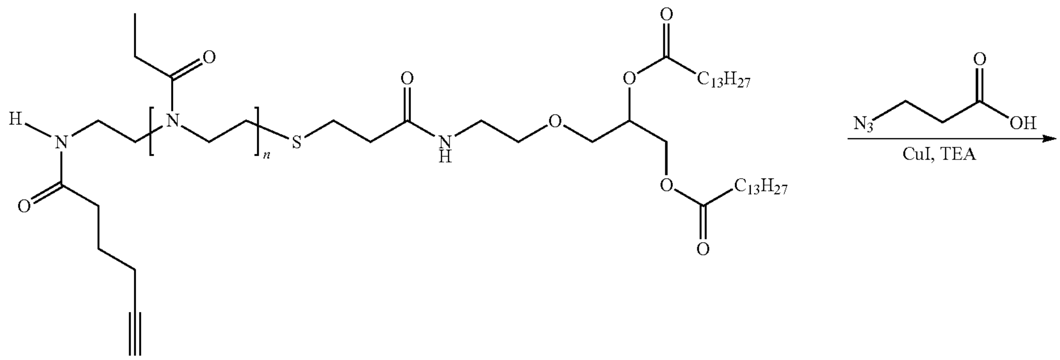

-continued

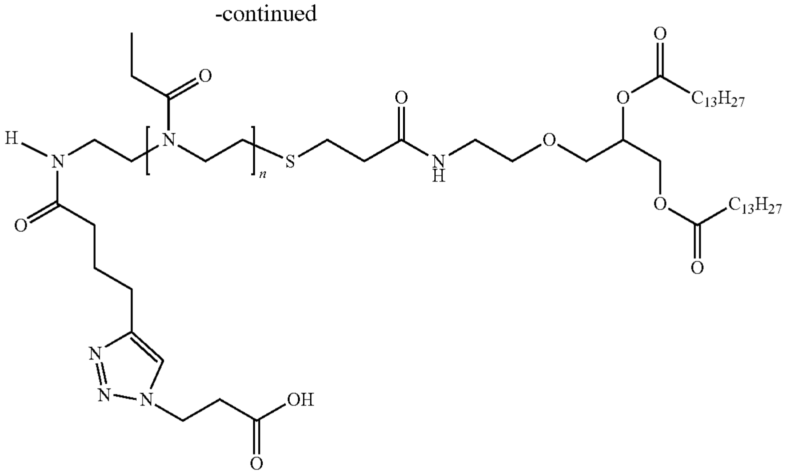

24

PEOZ 2K (1.21p) DMG (3-azidopropionate), Compound 24, was prepared in an analogous fashion to that previously described.

$^1$H NMR. HNMR analysis showed the standard backbone signals for PEOZ (500 MHz, DMSO) δ 7.82 (terminal NH); 3.35 ($CH_2CH_2$ backbone); 3.18 (N—$CH_2$); 3.02 (S—$CH_2$); 2.32-2.27 (C(O)—$CH_2$); 0.96 ($CH_3$). Additional signals were present for the lipid derivative moiety at δ 5.20 (CH); 4.26 ($CH_2$); 1.49 (C(O)$CH_2$); 1.23 ($CH_2$); 0.84 ($CH_3$). Additional signals were present for the triazole moiety at δ 7.78 (triazole CH); 4.54 (ester $CH_2$).

The POZ-lipids, LNPs, and pharmaceutical compositions described and claimed herein are not to be limited in scope by the specific embodiments herein disclosed, since these embodiments are intended as illustrations of several aspects of the disclosure. Any equivalent embodiments are intended to be within the scope of this disclosure. Indeed, various modifications of the formulas and structures in addition to those shown and described herein will become apparent to those skilled in the art from the foregoing description. Such modifications are also intended to fall within the scope of the appended claims. All patents and patent applications cited in the foregoing text are expressly incorporated herein by reference in their entirety. Any section headings herein are provided only for consistency with the suggestions of 37 C.F.R. § 1.77 or otherwise to provide organizational queues. These headings shall not limit or characterize the invention (s) set forth herein.

What is claimed:

1. A compound of Formula III $$R\text{-}(POZ)_n^a\text{-}Z\text{-}L\text{-}Lipid \quad (III)$$

wherein

R comprises an initiating group,

POZ comprises a polyoxazoline polymer of the structure $[N(COX)CH_2CH_2]$, wherein X is independently selected for each repeating unit of the polyoxazoline polymer from an unsubstituted or substituted alkyl, alkenyl, aralkyl, heterocycylalkyl group, alkyne-substituted alkyl, or an active functional group, n ranges from 1 to 1,001, a indicates a random copolymer or a block copolymer, Z comprises S, O, or N, and L-Lipid has the structure —$CH_2CH_2$—C(O)—N—$(R1)_x$, where R1 is an alkyl and x is at least 2.

2. The compound of claim 1, wherein R comprises a hydrogen, or a substituted or unsubstituted alkyl, and wherein n ranges from 15 to 35.

3. The compound of claim 1, having a rate of hydrolysis that is determined at least in part by L.

4. The compound of claim 1, having a hydrolysis half-life in 50 percent human plasma of about 10 minutes or less.

5. The compound of claim 1, having a hydrolysis half-life in 50 percent human plasma of about 120 hours or more.

6. The compound of claim 1, wherein Formula III is one of the following:

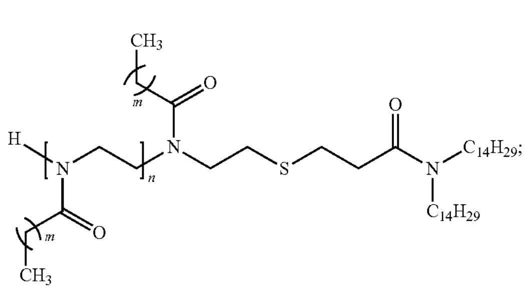

and

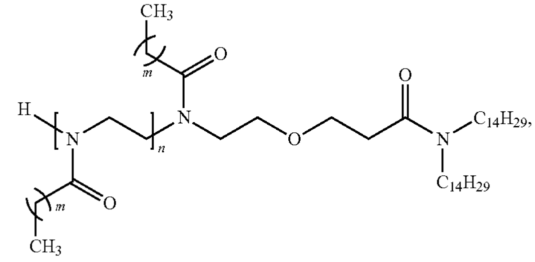

wherein m ranges from 0 to 2, o ranges from 1 to 5, and p ranges from 1 to 10.

7. A composition comprising the compound of claim 1, further comprising a cationic or ionizable lipid.

8. The compound of claim 1, exhibiting a change of about 30 percent to about 50 percent in peak area as measured by UV absorption at 210 nm after overnight exposure to lipo-amidase at 37° C.

9. The compound of claim 1, exhibiting about 10 percent or less change in peak area measured by UV absorption at 210 nm after overnight exposure to lipo-amidase at 37° C.

10. A compound of Formula III $$R\text{-}(POZ)_n^a\text{-}Z\text{-}L\text{-}Lipid \quad (III)$$

wherein

R comprises a substituted or unsubstituted alkyl,

POZ comprises a polyoxazoline polymer of the structure [N (COX) $CH_2CH_2$], wherein X is independently selected for each repeating unit of the polyoxazoline polymer from an unsubstituted or substituted alkyl, alkenyl, aralkyl, heterocycylalkyl group, alkyne-substituted alkyl, or an active functional group, n ranges from 15 to 35, a indicates a random copolymer or a block copolymer, Z comprises S, O, or N, L comprises an amidase-cleavable amide having the structure —$CH_2CH_2$—C(O)—N, and Lipid comprises a lipid consisting essentially of two alkyl chains.

11. A composition comprising the compound of claim 10, further comprising a cationic or ionizable lipid.

12. The compound of claim 10, having a rate of hydrolysis that is determined at least in part by L.

13. The compound of claim 10, having a hydrolysis half-life in 50 percent human plasma of about 10 minutes or less.

14. The compound of claim 10, having a hydrolysis half-life in 50 percent human plasma of about 120 hours or more.

15. The compound of claim 10, exhibiting a change of about 30 percent to about 50 percent in peak area as measured by UV absorption at 210 nm after overnight exposure to lipo-amidase at 37° C.

16. The compound of claim 10, exhibiting about 10 percent or less change in peak area measured by UV absorption at 210 nm after overnight exposure to lipo-amidase at 37° C.

17. A lipid nanoparticle comprising:

a compound of Formula III $$R\text{-}(POZ)_n^a\text{-}Z\text{-}L\text{-}Lipid \quad III$$

wherein R comprises an initiating group;

POZ comprises a polyoxazoline polymer of the structure [N (COX) $CH_2CH_2$]

wherein X is independently selected for each repeating unit of the polyoxazoline polymer from an unsubstituted or substituted alkyl, alkenyl, aralkyl, heterocycylalkyl group, alkyne-substituted alkyl, or an active functional group;

n ranges from 1 to 1,000, a indicates a random copolymer or a block copolymer,

Z comprises S, O, or N, and

L-Lipid has the structure —$CH_2CH_2$—C(O)—N—(R1) x, where R1 is an alkyl and x is at least 2;

an ionizable or cationic lipid;

a helper lipid; and a sterol lipid.

18. The lipid nanoparticle of claim 17, wherein Lipid comprises two hydrophobic moieties.

19. The lipid nanoparticle of claim 17, wherein R comprises a hydrogen, or a substituted or unsubstituted alkyl, and wherein n ranges from 15 to 35.

20. The lipid nanoparticle of claim 17, wherein R is a substituted or unsubstituted alkyl.

21. The lipid nanoparticle of claim 20, wherein n ranges from 15 to 35.

22. The compound of claim 1, wherein Z=N or O.

23. The compound of claim 10, wherein Z=N or O.

* * * * *